(12) United States Patent
Bashir et al.

(10) Patent No.: US 10,156,560 B1
(45) Date of Patent: Dec. 18, 2018

(54) LOCOMOTIVE BIOLOGICAL MACHINES

(71) Applicant: The Board of Trustees of the University of Illinois, Urbana, IL (US)

(72) Inventors: Rashid Bashir, Champaign, IL (US); Vincent Chan, Somerville, MA (US); Ritu Raman, Champaign, IL (US); Caroline Cvetkovic, Darien, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/486,375

(22) Filed: Sep. 15, 2014

Related U.S. Application Data

(60) Provisional application No. 61/877,676, filed on Sep. 13, 2013.

(51) Int. Cl.
| | |
|---|---|
| *G01N 33/50* | (2006.01) |
| *C12N 11/04* | (2006.01) |
| *C12N 13/00* | (2006.01) |

(52) U.S. Cl.
CPC ......... *G01N 33/5029* (2013.01); *C12N 11/04* (2013.01); *C12N 13/00* (2013.01); *G01N 2500/04* (2013.01)

(58) Field of Classification Search
None
See application file for complete search history.

(56) References Cited

U.S. PATENT DOCUMENTS

| | | | | |
|---|---|---|---|---|
| 6,488,872 | B1 * | 12/2002 | Beebe ................. | B01J 19/0093 264/139 |
| 2002/0022884 | A1 * | 2/2002 | Mansmann ........... | A61F 2/3872 623/14.12 |
| 2007/0141647 | A1 * | 6/2007 | Park ..................... | B29C 33/303 435/7.21 |

OTHER PUBLICATIONS

Wing et al., Plasma and cellular fibronectin: distinct and independent functions during tissue repair, Fibrinogenesis & Tissue Repair, 2011, 4:21, pp. 1-17.*
Cap, Definition by Merriam-Webster, retieved from the internet Feb. 20, 2017: https://www.merriam-webster.com/dictionary/cap.*
Surround, Definition by Merriam-Webster, retrieved from the internet Feb. 20, 2017: https://www.merriam-webster.com/dictionary/surround.*
Ikonen et al., Journal of Clinical & Experimental Cardiology, 2011, S:4, pp. 1-7.*
Arcaute et al., "Stereolithography of spatially controlled multimaterial bioactive poly(ethylene glycol) scaffolds," Acta Biomater. 6:1047-54 (2010).
Arcaute et al., "Stereolithography of three-dimensional bioactive poly(ethylene glycol) constructs with encapsulated cells" Ann Biomed Eng., 34(9), 1429-41 (2006).
Aubin et al., "Directed 3D cell alignment and elongation in microengineered hydrogels," Biomaterials 31:6941-51 (2010).
Bajaj et al., "3-D biofabrication using stereolithography for biology and medicine," Conf Proc IEEE Eng Med Biol Soc. 2012:6805-8 (2012) .
Chan et al., "3D fabrication of biological machines," Conf Proc IEEE Eng Med Biol Soc. 2013:314-7 (2013).
Chan et al., "Development of miniaturized wlaking biological machines," Sci Rep. 2:857 (2012).
Chan et al., "Directed cell growth and alignment on proteinpatterned 3D hydrogels with stereolithography," Virtual Phys Prototyp. 7:219-28 (2012).
Chan et al., "Enabling microscale and nanoscale approaches for bioengineered cardiac tissue," ACS Nano 7(3):1830-7 (2013) .
Chan et al., "Multi-material bio-fabrication of hydrogel cantilevers and actuators with stereolithography," Lab Chip 12(1):88-98 (2012) .
Chan et al., "Three-dimensional photopatterning of hydrogels using sterolithography for long-term cell encapsulation," Lab Chip 10(16):2062-70 (2010).
Chan et al., "Utilization and control of bioactuators across multiple length scales," Lab Chip 14(4):653-70 (2014).
Cooke et al., "Use of stereolithography to manufacture critical-sized 3D biodegradable scaffolds for bone ingrowth," J Biomed Mater Res. 64b(2), 65-9 (2003).
Cvetkovic et al., "Three-dimensionally printed biological machines powered by skeletal muscle", Proc Natl Acad Sci USA, 111(28):10125-30 (2014).
Dennis & Kosnik, "Excitability and isometric contractile properties of mammalian skeletal muscle constructs engineered in vitro," In Vitro Cell Dev Biol Anim. 36:327-35 (2000).
Feinberg et al., "Muscular thin films for building actuators and powering devices," Science 317:1366-70 (2007).
Hahn et al., "Three-dimensional biochemical and biomechanical patterning of hydrogels for guiding cell behavior," Adv Mater. 18:2679-84 (2006).
Herr & Dennis, "A swimming robot actuated by living muscle tissue", J Neuroeng Rehabil. 1(1):6 (2004).
Hosseini et al., "Engineered contractile skeletal muscle tissue on a microgrooved methacrylated glatin substrate," Tissue Eng Part A, 18(23-24)"2453-65 (2012).
Kim et al., "Establishment of a fabrication method for a long-term actuated hybrid cell robot," Lab Chip 7:1504 (2007).
Kim et al., "Quantitative evaluation of cardiomyocyte contractility in a 3D micro-environment," J Biomech. 41:2396-401 (2008).
Jeong et al., ""Living" microvascular stamp for patterning of functional neovessels; orchestrated control of matrix property and geometry," Adv Mater 24(1):58-63 (2012).
Lam et al., "Microfeature guided skeletal muscle tissue engineering for highly organized 3-dimensional free-standing constructs," Biomaterials 30:1150-5 (2009).

(Continued)

*Primary Examiner* — Thomas J. Visone
*Assistant Examiner* — Evelyn Y Pyla
(74) *Attorney, Agent, or Firm* — McDonnell Boehnen Hulbert & Berghoff LLP

(57) ABSTRACT

The invention provides locomotive biological machines comprised of hydrogel structures and one or more types of cells. The locomotive biological machines are capable of controlled directional movement and can be used for sensing, information processing, actuation, protein expression, and transportation.

20 Claims, 35 Drawing Sheets

(56) References Cited

OTHER PUBLICATIONS

Magdanz et al., "Development of a sperm-flagella driven micro-bio-robot," Adv Mater. 25(45):6581-8 (2013).

Mann et al., "Smooth muscle cell growth in photopolymerized hydrogels with cell adhesive and proteolytically degradable domains: synthetic ECM analogs for tissue engineering," Biomaterials 22:3045-51 (2001).

Mechels et al., "A review on stereolithography and its applications in biomedical engineering," Biomaterials 31:6121-30 (2010).

Metters et al., "Fundamental studies of a novel, biodegradable PEG-b-PLA hydrogel," Polymer 41:3993-4004 (2000).

Nawroth et al., "A tissue-engineered jellyfish with biomimetic propulsion", Nat Biotech. 30:792-7 (2012).

Park et al., "Fabrication of complex 3D polymer structures for cell—polymer hybrid systems," J Micromech Microeng. 16:1614-9 (2006).

Park et al., "Real-time measurement of the contractile forces of self-organized cardiomyocytes on hybrid biopolymer microcantilevers," Anal Chem. 77:6571-80 (2005).

Peyton et al., "The use of poly(ethylene glycol) hydrogels to investigate the impact of ECM chemistry and mechanics on smooth muscle cells," Biomaterials 27(28):4881-93 (2006).

Sakar et al., "Formation and optgenetic control of engineered 3D skeletal muscle bioactuators", Lab Chip 12:4976-85 (2012).

Schmidt et al., "Tailoring the dependency between rigidity and water uptake of a microfabricated hydrogel with the conformational rigidity of a polymer cross-linker," Biomacromolecules 14(5):1361-9 (2013).

Shapira-Schweitzer et al., "A photopolymerizable hydrogel for 3-D culture of human embryonic stem cell-derived cardiomyocytes and rat neonatal cardiac cells," J Mol Cell Cardiol. 46:213-24 (2009).

Tsang et al., "Fabtrication of 3D hepatic tissues by additive photopatterning of cellular hydrogels", FASEB J., 21 (3):790-801 (2007).

Williams et al., "A self-propelled biohybrid swimmer at low Reynolds number," Nat Commun 5:3081 (2014).

Xi et al., "Self-assembled microdevices driven by muscle," Nat Mater. 4:180-4 (2005).

Zorlutuna et al., "Stereolithography-based hydrogel microenvironments to examine cellular interactions," Adv Func Mater. 21:3642-51 (2011).

\* cited by examiner

FIG. 1E
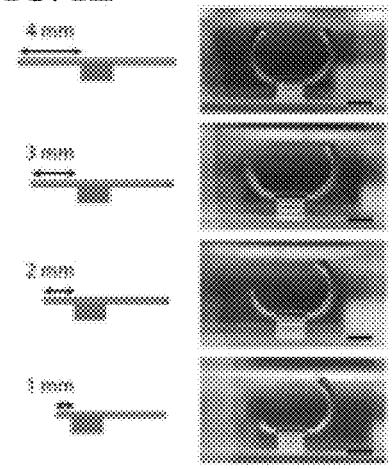
FIG. 1F "Bio-Bot"
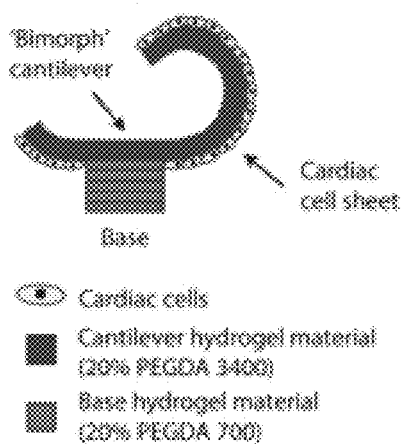

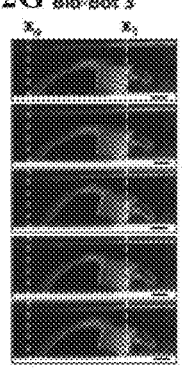
FIG. 2G Bio-Bot 3
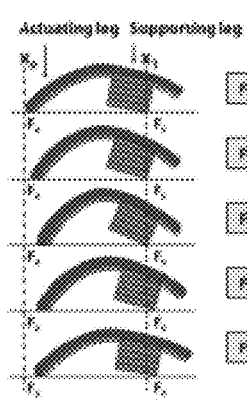
FIG. 2H
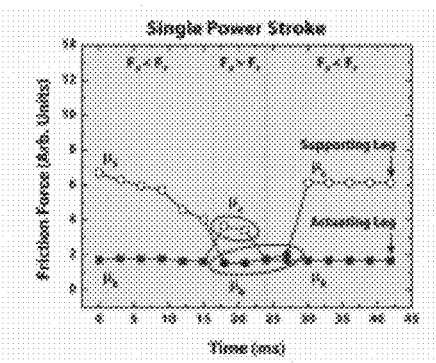
FIG. 2I

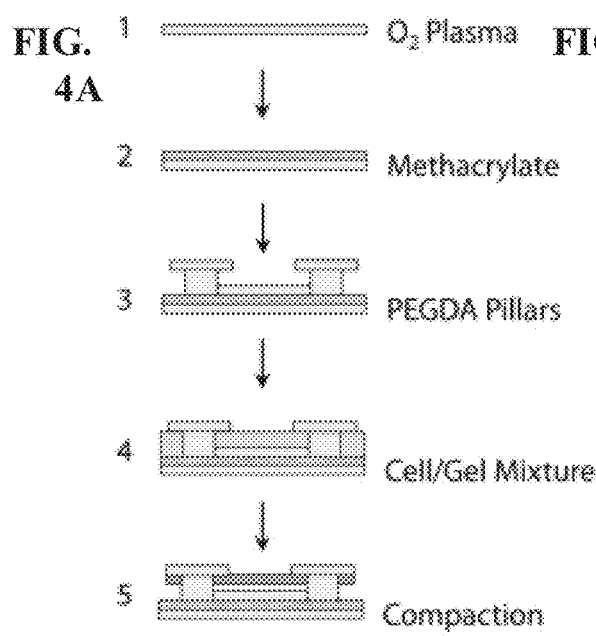
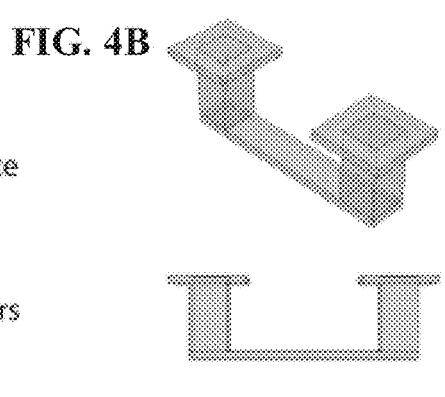
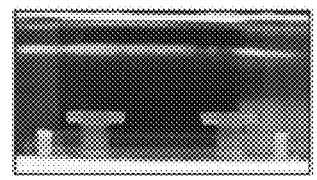
FIG. 4A
FIG. 4B
FIG. 4C

FIG. 8A
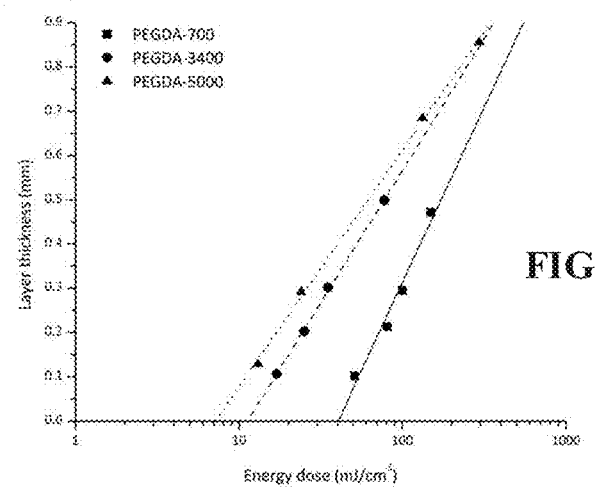
FIG. 8B
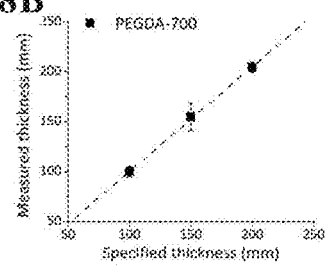
FIG. 8C FIG. 8D
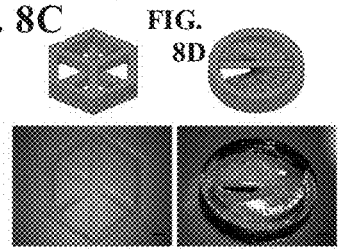

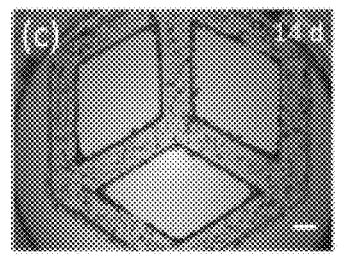
FIG. 14C
FIG. 14A
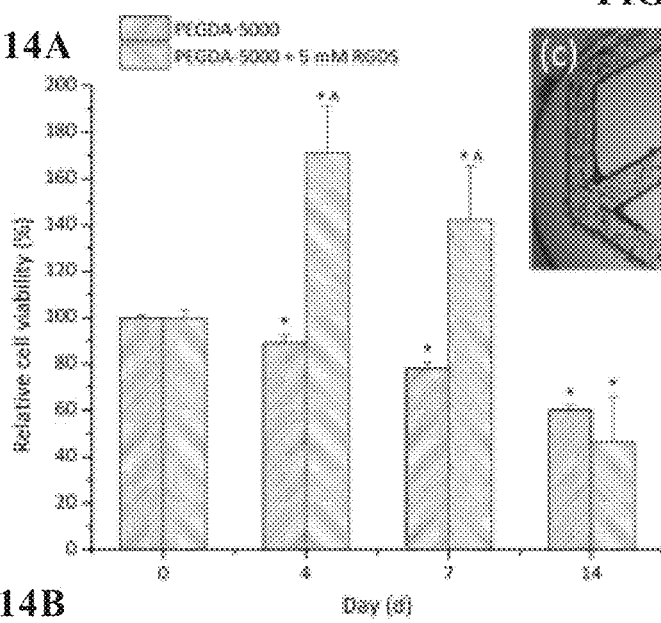
FIG. 14B
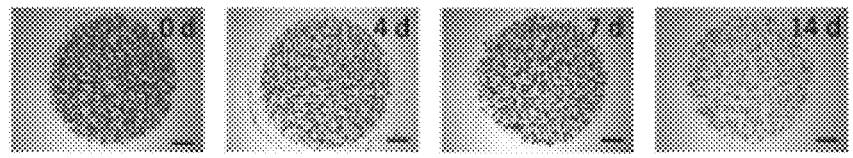

CMTMR

Cell Tracker

Cell Tracker

CMTMR

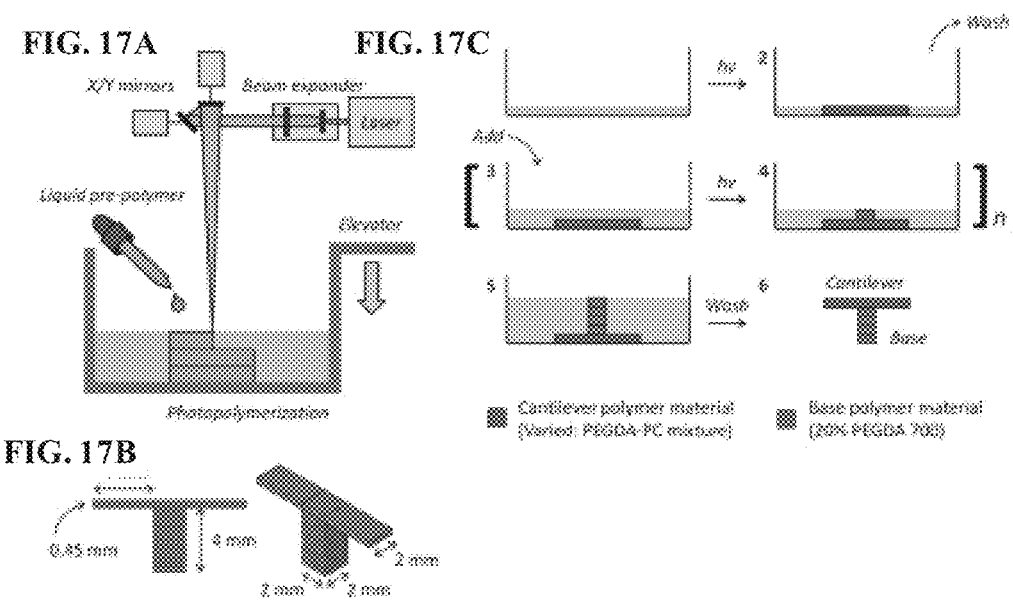

450 μm

300 μm

FIG. 21A
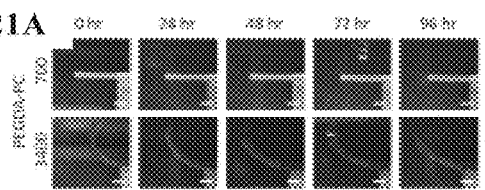
FIG. 21B
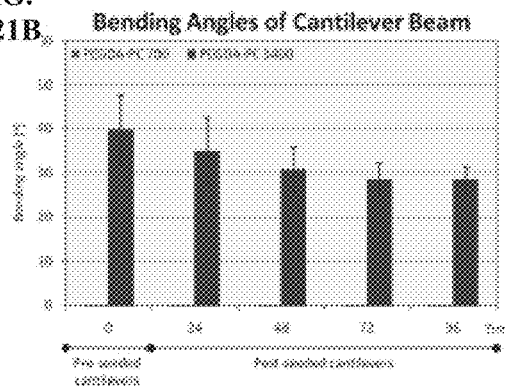
Bending Angles of Cantilever Beam
FIG. 21C Cell Sheet Stress on Cantilever Beam
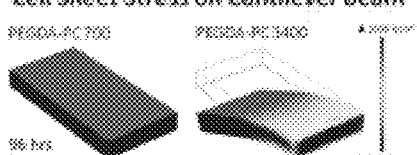
FIG. 21D
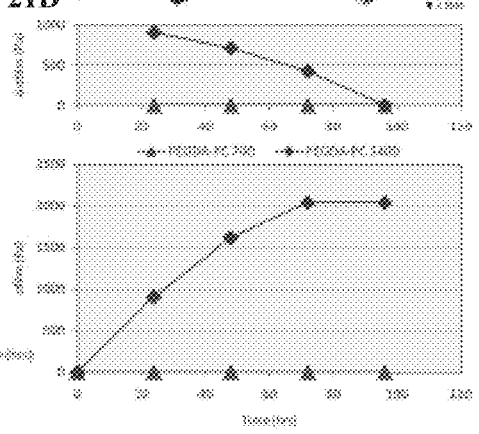

FIG. 27A
(+) Blebbistatin
(−) IGF
FIG. 27B
(−) Blebbistatin
(−) IGF
FIG. 27C
(−) Blebbistatin
(+) IGF
24 hrs
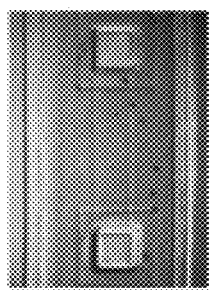 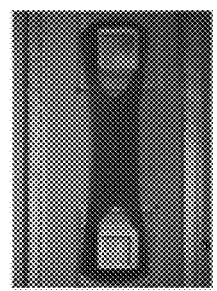 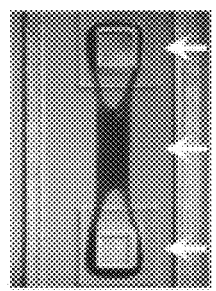
← Pillar
← Muscle
← Pillar
48 hrs
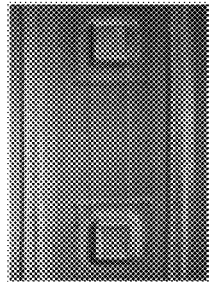 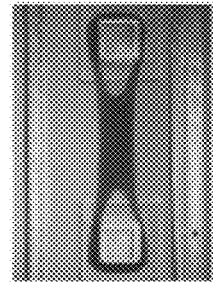 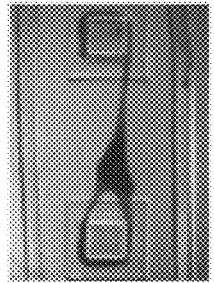

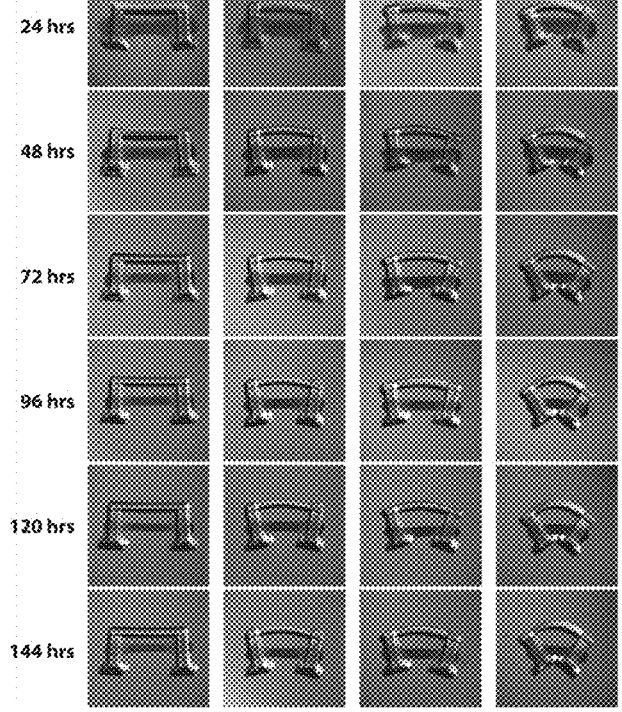

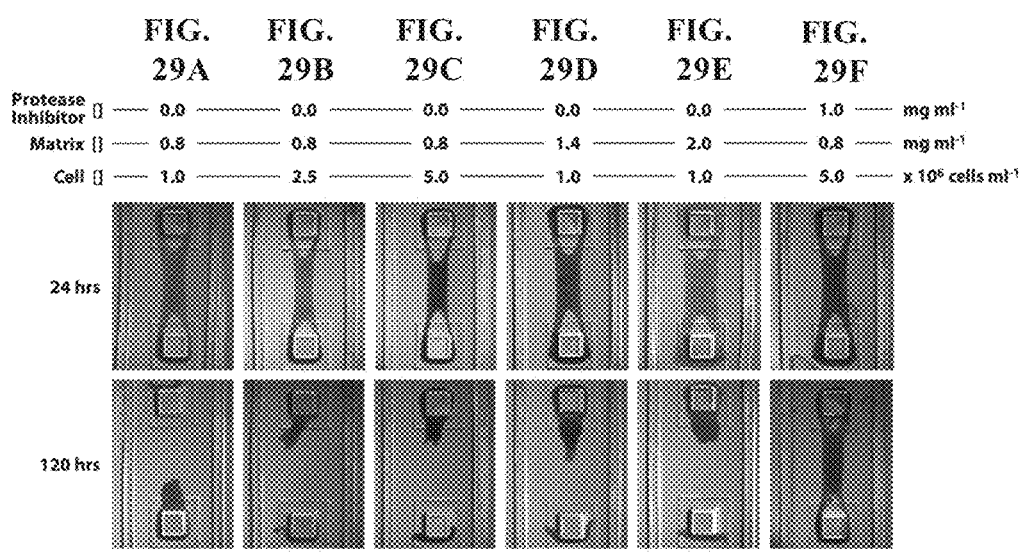

LOCOMOTIVE BIOLOGICAL MACHINES

PRIORITY

This application claims the benefit of U.S. Ser. No. 61/877,676, filed on Sep. 13, 2013, which is incorporated by reference herein in its entirety.

STATEMENT REGARDING FEDERALLY SPONSORED RESEARCH OR DEVELOPMENT

This invention was made with U.S. Government support under contract number CBET-0939511 awarded by the National Science Foundation, and contract number W81 XWH081 0701 awarded by the United States Army. The U.S. Government has certain rights in the invention.

BACKGROUND

Biomolecular motors are considered promising materials for constructing biological actuators. In general, biomolecular actuators are driven by the conversion of adenosine triphosphate (ATP) to drive their movement. These actuators can be used in nanoscale mechanical devices to pump fluids, open and close valves, and provide translational movement of cargo. The difficulty lies in how to integrate these sophisticated functions to do specific tasks. A cell-based biological machine is a set of sub-components comprising living cells and cell-instructive micro-environments that interact to perform a prescribed task. Functions of biological machines include sensing, information processing, actuation, protein expression, and transportation.

There has been substantial interest in the fabrication of biological machines. Most cell-based biohybrid actuators have been limited to rigid materials such as silicon and polydimethylsiloxane (Kim et al., 2007, *Lap Chip* 7:1504-8; Feinberg et al., 2007, *Science* 317: 1366-70.) Hydrogels, which are cross-linked polymer networks that are hydrated and possess tissue-like elasticity, are a useful class of compounds for biological applications (Drury & Mooney, 2003, *Biomaterials*, 24:4337-51; Slaughter et al., 2009, *Adv. Mater.* 21:3307-29). Many biocompatible hydrogels with varying structures and properties have been identified in nature or developed in the lab.

There remains a need to develop controllable, soft robotic devices with bidirectional locomotive capabilities that can dynamically sense and respond to a range of complex environmental signals. There also remains the need to develop methods for fabricating such robotic devices with short fabrication time, the potential for scalability, and spatial control.

SUMMARY OF THE INVENTION

One embodiment of the invention provides a composition (e.g., a bio-bot or locomotive biological machine) comprising a hydrogel strip having an upper surface and an opposing lower surface and having a length, a width, and a thickness. The composition also comprises a hydrogel base having a length and a width, wherein the hydrogel base is coupled to the lower surface of the hydrogel strip, and wherein the length of the hydrogel base is shorter than the length of the hydrogel strip. One or more cell types are immobilized to the lower surface of the hydrogel strip. The hydrogel base can be offset from a lateral axis of the hydrogel strip. The one or more cell types can be neurons, cardiac muscle cells, skeletal muscle cells, progenitor muscle cells, endothelial cells, fibroblasts or combinations thereof. The one or more cell types can be cardiac muscle cells and optionally, one or more other cell types. The one or more cell types can be immobilized to the lower surface of the hydrogel strip by one or more cell-binding proteins. The composition can be capable of locomotion. The hydrogel strip and hydrogel base can comprise a photopolymerizable hydrogel. The one or more cell types can be immobilized at one or more distinct locations on the hydrogel strip. The lower surface of the hydrogel strip can further comprise one or more types of proteins coupled to hydrogel. The hydrogel base of the composition can be placed on a substrate providing friction between the substrate and the hydrogel base. The hydrogel strip can have a kPa of about 10 to about 75 and the hydrogel base can have a kPa of about 200 to about 2,000.

Another embodiment of the invention provides a method of making a bio-bot comprising making the hydrogel strip and the hydrogel base coupled to the lower surface of the hydrogel strip with a stereo-lithographic apparatus and polymerizable liquid materials and immobilizing one or more cell types to the lower surface of the hydrogel strip.

Still another embodiment of the invention provides a method of making a bio-bot comprising making the hydrogel strip and the hydrogel base coupled to the lower surface of the hydrogel strip with a micromold and polymerizable liquid materials and immobilizing one or more cell types to the lower surface of the hydrogel strip.

Yet another embodiment of the invention provides a method of controlling the directional locomotion of the bio-bot described above comprising exposing the entire composition or a selected portion of the composition to light, an electrical pulse, or a chemical. Controlling the directional locomotion of the composition can include starting locomotion, stopping locomotion, slowing locomotion, accelerating locomotion, changing the direction of locomotion or combinations thereof.

Another embodiment of the invention provides a method of detecting the response of the bio-bot above or the one or more types of cells of bio-bot to one or more test agents. The method comprises contacting the bio-bot with the one or more test agents and monitoring one or more of the following parameters: cell death, cell viability, number of cells, apoptosis, cell proliferation, contractile responses of the cells, angiogenesis, movement of the composition, or directional locomotion of the bio-bot, wherein the response of the composition or the one or more types of cells of the bio-bot to the test agents are detected.

Yet another embodiment of the invention provides a composition (e.g., a bio-bot or a biological machine) comprising two or more hydrogel pillars having top and bottom base end surfaces, wherein the two or more hydrogel pillars are coupled to a hydrogel beam at their top base end surfaces, and wherein the hydrogel beam extends between the two or more hydrogel pillars. A gel comprising one or more types of cells surrounds the two or more pillars, wherein the bottom base end surfaces of the pillars are not covered by the gel. The two or more hydrogel pillars can have caps on their bottom base end surfaces that are not covered by the gel. The one or more of the hydrogel pillars can have a different height than one or more of the other hydrogel pillars. The one or more caps can have a different thickness than one or more of the other caps. The one or more cell types can be neurons, cardiac muscle cells, skeletal muscle cells, progenitor muscle cells, endothelial cells, fibroblasts or combinations thereof. The one or more cell types can comprise neurons and muscle cells, wherein the muscle cells form one or more muscle fibers and wherein the neurons and muscle fibers comprise one or more neuromuscular junctions. The one or more cell types can include muscle cells and the gel can comprise the one or more types of cells and can be polymerized and condensed around the pillars to form a solid muscle strip. The one or more cell types can be activated by light, an electric current, or a chemical compound. The gel can comprise one or more extracellular matrix proteins. In one or more embodiments of the invention, the 3 or more hydrogel pillars can be arranged in a row and can all be coupled to a hydrogel beam at the top base end surfaces of the hydrogel pillars, wherein one or more of the hydrogel pillars are further connected via an additional hydrogel beam in one or both perpendicular directions from the row to an additional one or more pillars, wherein the additional hydrogel beam connects the top base end surfaces of the hydrogel pillars. In one embodiment of the invention the hydrogel pillars can be arranged in rows and columns within a grid-like array with one or more rows of hydrogel pillars and one or more columns of hydrogel pillars, wherein each row of hydrogel pillars can be connected at the top base end surfaces of the hydrogel pillars by a hydrogel beam and wherein each column of hydrogel pillars can be connected at the top base end surfaces of the hydrogel pillars by a hydrogel beam.

Still another embodiment of the invention provides a composition comprising a multitude of hydrogel pillars having top and bottom base end surfaces arranged in rows and columns within a grid-like array with one or more rows of hydrogel pillars and one or more columns of hydrogel pillars, wherein each row of hydrogel pillars is connected at the top base end surfaces of the hydrogel pillars by a hydrogel base, wherein the hydrogel base connects all the hydrogel pillars. A gel comprising one or more types of cells can surround the two or more pillars, wherein the bottom base end surfaces of the pillars are not covered by the gel.

Even another embodiment of the invention provides a method of making the compositions described above by making the two or more hydrogel pillars coupled to a hydrogel beam with a stereo-lithographic apparatus and polymerizable liquid materials and surrounding the two or more pillars with the gel and one or more types of cells.

Another embodiment of the invention provides a method of making the composition described above. The method comprises making the two or more hydrogel pillars coupled to a hydrogel beam with a micromold and polymerizable liquid materials and surrounding the two or more pillars with the gel and one or more types of cells.

Yet another embodiment of the invention provides a method of controlling the directional locomotion of the composition described above comprising exposing the entire composition or a selected portion of the composition to light, an electrical pulse, or a chemical. Controlling the directional locomotion of the composition can include starting locomotion, stopping locomotion, slowing locomotion, accelerating locomotion, or changing the direction of locomotion.

Still another embodiment of the invention provides a method of detecting the response of the composition described above or the one or more types of cells of the composition to one or more test agents. The method comprises contacting the composition with the one or more test agents and monitoring one or more of the following parameters: cell death, cell viability, number of cells, apoptosis, cell proliferation, contractile responses of the cells, angiogenesis, movement of the composition, or directional locomotion of the composition, wherein the response of the composition or the one or more types of cells of the composition to the test agents are detected.

Therefore, the invention provides unique biological locomotive machines, methods of making the machines, and methods of using the machines.

BRIEF DESCRIPTION OF THE DRAWINGS

FIG. 1A shows a diagram of 3D stereo-lithographic printer consisting of a HeCd laser at 325 nm and galvanometer scanning mirrors. The mirrors are computer controlled, and a stage lowers the part a specified distance after each layer. FIG. 1B shows a process flow diagram for high-throughput array of bio-bots. FIG. 1D shows a process flow diagram for functionalization of the cantilevers with collagen and seeding of cardiac cells. FIG. 1E shows symmetrical and asymmetrical bio-bots. FIG. 1F is a schematic of a bio-bot design comprising a biological biomorph cantilever with a cardiac cell sheet. All scale bars are 1 mm.

FIG. 4A is a schematic of a fabrication process flow of hydrogel constructs method of fabrication of muscle strip bio-bots, as described in Example 15: (1) Glass substrates were cleaned with oxygen-plasma treatment, (2) Dilute 3-(trimethoxysilyl)propyl methacrylate (TPM, 2% v/v) in 100% ethanol was added to methacrylate the glass substrate, (3) Poly(ethylene glycol) diacrylate (PEGDA, 20% v/v $M_w$ 700) was layered and photopolymerized with the SLA to fabricate pillar/beam hydrogel constructs, (4) Mixtures of cell-embedded type I collagen and Matrigel™ were casted around the pillars and set in the incubator, (5) Cell attachment and traction forces pulled on and compacted the gels to form 3D muscle strip. FIG. 4B is a computer-aided design (CAD) drawing of a pillar/beam of a muscle strip bio-bot, and FIG. 4C is an actual image of the pillar/beam of the muscle strip bio-bots.

FIG. 5A shows CAD images of hydrogel structures with varying numbers and arrangements of beams and pillars. FIGS. 5B and 5C show top and side views, respectively, of hydrogel structures fabricated according to the designs in FIG. 5A. Scale bars are 2 mm.

FIG. 8A-D shows the relationship between laser energy dose and cured thickness of PEGDA hydrogels. FIG. 8A shows characterization of the laser energy dose required to cure 20% PEGDA hydrogels with $M_w$ 700, 3,400, and 5,000 Da. FIG. 8B shows that the specified and measured thicknesses for $M_w$ 700 Da were relatively equal. FIGS. 8C and 8D show CAD drawings and images of 3D hydrogels ($M_w$ 700 Da) fabricated by the "bottom-up" approach. All experiments used 0.5% photoinitiator concentration. Scale bars are 1 mm.

FIGS. 14A and 14B show viability of NIH/3T3 cells encapsulated in multiple-layer hydrogels of 5,000 Da PEGDA with or without RGDS peptides. The $M_w$ of PEGDA hydrogels were varied using $M_w$ 5,000. (a) OD (490 nm) values quantified with MTS assay were normalized to Day 0. All values are mean±standard deviation of n=3. (*) denotes statistical difference compared to 0 day of same approach. (^) denotes statistical difference compared to different approach of same day. FIG. 14B: MTT staining that shows living cells in a patterned multi-layer PEGDA hydrogel with $M_w$ 5,000 Da after 14 days. FIG. 14C shows MTT staining of living cells in a single-layer PEGDA hydrogel with $M_w$ 5,000 Da after 0, 4, 7, and 14 days. There is a noticeable difference in intensity after 14 days. Scale bars are 1 mm.

FIG. 17A-C show multi-material cantilever fabrication. (A) The cantilevers were fabricated with a 3D stereolithographic printer, which uses a UV laser to construct layer-by-layer patterns. (B) Two separate cantilevers (2 mm wide×4 mm long×0.45 mm thick) were built on opposite ends of one base (2 mm wide×2 mm long×4 mm thick). The molecular weight of the PEGDA-PC cantilever beam was varied using either PEGDA-PC 700 or 3400, while the base was kept constant using PEGDA-PC 700. (C) A simplified fabrication process flow is shown, which begins with the formation of the cantilever beam before the base.

FIG. 21A-D shows cell sheet stress calculations. Cells from the ventricles of neonatal rat hearts were seeded on the backside of the cantilever beams. (A) The traction forces of these cells, which are responsible for migration, proliferation, and differentiation, caused the PEGDA-PC 3400 cantilever beams to deflect downward in the Z-direction over time. (B) The average bending angles of the cantilevers were measured over a 96 hour period, which was used to calculate the deflection at the tip of the beams. (C) These deflections were simulated using finite element analysis to calculate the stresses exerted by the cell sheets due to traction forces. (D) These stresses exerted by the cell sheet and modeled as a thin film were plotted over time. The change in stress over 24 hour time points decreased and reached 0 by 96 hours. Scale bars are 1 mm. Statistics by one-way ANOVA, Tukey's test, *p<0.05 for n=8 and SD.

FIG. 27 A-C shows formation of 3D skeletal muscle strips. (A) The traction forces of skeletal myoblasts ($C_2C_{12}$) embedded in and attached to type I collagen and Matrigel™ caused compaction of the solidified gels around pillar/beam hydrogel constructs. This was verified by independently adding (B) insulin-like growth factor 1 (IGF-1, 50 ng ml$^{-1}$) and (C) blebbistatin (50 μM) to the medium. Since IGF-1 is a potent mitogen, there were increased traction forces on the muscle strip, which caused it to break within 48 hours of culture. In contrast, blebbistatin is a myosin ATPase inhibitor that reduced cell contraction on the muscle strip and prevented its compaction after 48 hours of culture.

FIG. 28A-D shows optimization of beam stiffness with passive tension parameters. The beam stiffness between the pillars was varied as a function of exposure energy for (A) 500, (B) 150, (C) 125, and (D) 100 mJ cm$^{-1}$. The passive tensions generated by the muscle strips were applied to the beam, causing it to flex. The degree of flexure was dependent on the stiffness of the beam.

FIG. 29A-F shows optimization of passive tension parameters. 3D skeletal muscle strips consistently snapped after 5 days in culture, which led us to vary a number of parameters, such as cell ($C_2C_{12}$ myoblast) concentration, matrix (type I collagen) concentration, and the presence of protease inhibitors (ε-aminocaproic acid). Despite variation of cell concentrations at (A) 1.0, (B) 2.5, and (C) 5.0 cells ml$^{-1}$ in 0.8 mg ml$^{-1}$ type I collagen, all the muscle strips continued to snap within 5 days. This was the also the case with increasing the matrix concentration at 0.8, (D) 1.4, and (E) 2.0 mg ml$^{-1}$. It is noteworthy to mention that the area of the muscle strips decreases with cell concentration, but increases with matrix concentration. (F) Finally, ε-aminocaproic acid (EAC) inhibits protease activity that degrades proteins, such as collagen. Addition of EAC (1 mg ml$^{-1}$) prevented the muscle strip from snapping (stable even after 14 days).

DETAILED DESCRIPTION OF THE INVENTION

Figure 1A:
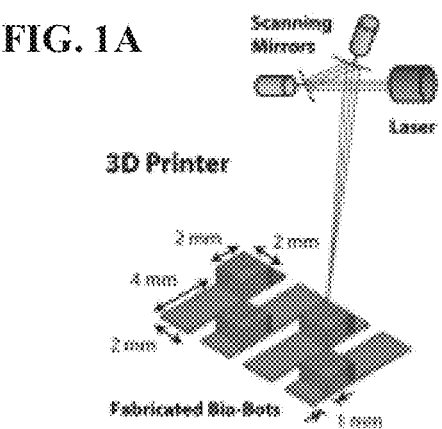
FIGS. 1A, 1B, and 1D are schematics of bio-bot fabrication.
Figure 1B:
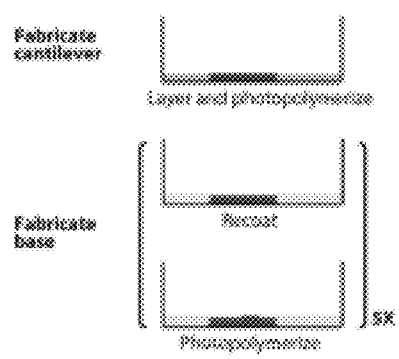
Figure 1C:
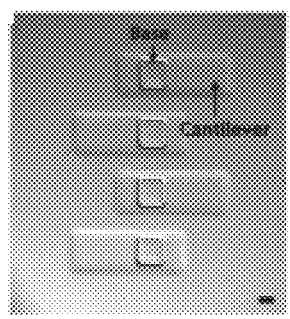
FIG. 1C shows representative top-down images depicting fabricated bio-bots with cantilever and base structures.

As used herein, the singular forms "a," "an," and "the" include plural referents unless the context clearly dictates otherwise. The term "about" in association with a numerical value means that the numerical value can vary plus or minus by 5% or less of the numerical value.

Locomotive Biological Machines

A 'biological machine' or cellular system can be defined as a set of sub-components consisting of living cells and cell-instructive micro-environments that interact to perform a range of prescribed tasks. Examples of prescribed tasks include sensing, information processing, transport, protein expression, and actuation. By combining clusters of different cell types, such as neurons, muscle cells, and endothelial cells, complex biological machines can be created for specific applications in health, security, and the environment. Exemplary biological machines include organ mimics for drug testing, biological robots for replication and repair, and implantable systems for drug sensing, synthesis, and release.

The biological machines of the invention can have an actuation module for locomotion including controlled directional movement, referred to as an autonomous "bio-bot". Actuation produced by a cluster of muscle cells can be used to power the bio-bot. 3D lithographic technology can be integrated with appropriate biomaterials to spatially organize, for example, contractile cardiac cells or skeletal muscle cells on a bio-bot with desired geometry, mechanics, and cell adhesion molecules for optimal and robust locomotion.

Hydrogel Strip and Base (Cantilever) Bio-Bots

In one embodiment of the invention a biological machine or bio-bot comprises a hydrogel strip having an upper surface and an opposing lower surface and having a length, a width, and a thickness. A hydrogel base having a length and a width is coupled to the lower surface of the hydrogel strip. The length of the hydrogel base is shorter than the length of the hydrogel strip. The hydrogel base can be offset from a lateral axis of the hydrogel strip. One or more cell types can be immobilized to the lower surface of the hydrogel strip.

The initial shape and degree of curvature of the bio-bot cantilever (i.e., the hydrogel strip of the bio-bot) can be precisely defined by adjusting its thickness during fabrication. See FIG. 1A-D. The tension generated by self-organizing cardiomyocytes into cell sheets on the cantilever results in final curvature of the hydrogel strip (cantilever). By harnessing an asymmetric design and the synchronous contraction of the muscle cell sheet, a walking motion of the bio-bot is demonstrated. See FIG. 2. Locomotion can be predicated on varying friction between the bio-bot legs and the substrate during the course of contraction. Altering the cantilever curvatures can change the surface area of contact, and hence, the friction, and its effect on net forward movement of the bio-bot.

Hydrogel Strip (Cantilever)

Hydrogel strips of the hydrogel strip and base bio-bot (also called a cantilever bio-bot herein) and other hydrogel structures of the invention (e.g., three dimensional muscle powered bio-bots) are made of a hydrogel, such as a photopolymerizable hydrogel. Hydrogels can be made up of natural materials or synthetic materials or combinations thereof. Suitable hydrogels can be made up of, for example, collagen, fibrin, chitosan, hyaluronic acid, chondroitin sulfate, alginate, agar/agarose polyethylene (PE), polyethylene glycol (PEG), polyethylene oxide (PEO), polyethylene glycol diacrylate (PEGDA), poly(ethylene glycol)-dimethacrylate (PEGDMA), polyacrylamide, polylysine, oligo(poly (ethylene glycol) fumarate) (OPF), polydimethylsiloxane (PDMS), polypropylene (PP), poly(propylene fumarate) (PPF), poly(N-isopropylacrylamide) (PNIPA, PNIPAAm, NIPA, PNIPAA or PNIPAm), poly(lactic) acid (PLA), poly-L-lactide (PLLA), polyvinyl acetate (PVA), polysulfone, polyvinylchloride (PVC), polytetrafluoroethylene (PTFE), polyetheretherketone (PEEK), poly(lactic-co-glycolic acid) (PLGA), poly(propylene fumarate) (PPF), poly(aldehyde guluronate), Polycaprolactone (PCL), polyphenylene oxide (PPO), PEO-PPO-PEO, PLGA-PEG, PLGA, PEG-PLLA-PEG, PCL-PEG-PCL, PCLA-PEG-PCLA, PEG-PCL-PEG, acrylated forms of polyethylene glycol, acrylated forms of polydimethylsiloxane, acrylated forms of polyacrylamide, or combinations thereof.

In one embodiment the hydrogel strip (or any other hydrogel structure of the invention) is made of a biocompatible hydrogel that can break down over time within for example, a mammalian body. For example, a hydrogel structure of the invention can comprise a PEG hydrogel with degradable units. PEG can be rendered degradable by short peptides in its backbone for enzymatic cleavage by cells on or with the hydrogel (Adelöw et al., *Biomaterials*, 2008, 29(3), 314-326) or by making a copolymer with a hydrolytically degradable polymer like PLA (Metters et al., *Polymer*, 2000, 41, 3993-4004). In another embodiment the hydrogel is a mixture of PEG diacrylate (PEGDA) and acrylic-PEG-collagen (PC). Collagen I can be modified on the lysine groups with acrylic groups to UV cross-link to the PEG backbone in the presence of a photoinitiator.

A hydrogel strip (also called a cantilever herein) can be made of a hydrogel, such as a photopolymerizable hydrogel (e.g. PEGDA) of weight average molecular weight ($M_w$) of about 500, 1,000, 1,250, 1,500, 1,750, 2,000, 2,225, 2,500, 2,750, 3,000, 3,250, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000 $M_w$ or more (or any range between about 500 and about 8,000 $M_w$) or 8,000, 7,750, 7,500, 7,250, 7,000, 6,750, 6,500, 6,250, 6,000, 5,750, 5,500, 5,250, 5,000, 4,750, 4,500, 4,250, 4,000, 3,750, 3,500, 3,400, 3,250, 3,000, 2,750, 2,500, 2,225, 2,000, 1,750, 1,500, 1,250, 1,000, 500 $M_w$ or less (or any range between about 8,000 or about 500 $M_w$).

A hydrogel strip can be any shape or size, including for example, rectangular, ovoid, triangular, or circular. The hydrogel strip can be, in general, an elongated shape. The hydrogel strip has an upper and lower surface. The upper and lower surfaces (or any hydrogel surface of the invention) can be generally smooth or can be textured or nanotextured. Examples of surface textures include ridges, hills, grooves, mesas/plateaus, terraces, trenches, surface pores, and so forth. Nanotextures have at least one dimension that is less than 100 nm in length. For example, a ridge or trench that is 10 nm wide by 50 microns long is a nanostructure, because it is has at least one dimension (e.g., its width), which is less than 100 nm in length.

In one embodiment the hydrogel strip is an elongated shape such as rectangular shape with a length, width, and a thickness. The length of the strip is greater than the width. The length of the hydrogel strip can be about 0.075, 0.1, 0.5, 1, 2, 3, 4, 5, 6, 7, 8, 9, 10, 11, 12, 13, 14, 15, 20, 30, 40, 50 or more mm (or any range between about 0.075 and about 50 mm) or about 50, 40, 30, 20, 15, 14, 13, 12, 11, 10, 9, 8, 7, 6, 5, 4, 3, 2, 1, 0.5, 0.1, 0.075 mm or less (or any range between about 50 mm and about 0.075 mm). The width of the rectangular strip can be about 0.05, 0.1, 0.5, 1, 2, 3, 4, 5, 6, 7, 8, 9, 10, 11, 12, 13, 14, 15, 20, 30, 40 or more mm (or any range between about 0.05 and about 40 mm) or about 40, 30, 20, 15, 14, 13, 12, 11, 10, 9, 8, 7, 6, 5, 4, 3, 2, 1, 0.5, 0.1, 0.05 mm or less (or any range between about 40 mm and about 0.05 mm). The thickness of the hydrogel strip can be about 50, 60, 70, 80, 90, 100, 125, 150, 175, 200, 225, 250, 275, 300, 325, 350, 375, 400, 425, 450, 475, 500, 525, 550, 575, 600, 650, 700, 750 µm or more (or any range between about 50 and about 750 µm) or 750, 700, 650, 600, 575, 550, 525, 500, 475, 450, 425, 400, 375, 350, 325, 300, 275, 250, 225, 200, 175, 150, 125, 100, 90, 80, 70, 60, 50 µm or less (or any range between about 750 and about 50 µm).

The hydrogel strip can have a kPa of about 5, 10, 15, 20, 22, 25, 30, 35, 40, 45, 50, 55, 60, 65, 70, 75, 80, 90, 100, 150, 200, 250 or more (or any range between about 5 and about 250) or about 250, 200, 150, 100, 90, 80, 75, 70, 65, 60, 55, 50, 45, 40, 35, 30, 25, 22, 20, 15, 10, 5 or less (or any range between about 250 and about 5).

Hydrogel Base

The hydrogel base can be made of any hydrogel as described for the hydrogel structures above. The hydrogel base can have a weight average molecular weight of about 50, 100, 200, 300, 400, 500, 600, 700, 800, 1,000, 1,250, 1,500, 1,750, 2,000, 2,225, 2,500, 2,750, 3,000, 3,250, 3,400, 3,500 $M_w$ or more (or any range between about 50 and about 3,500 $M_w$) or about 3,500, 3,400, 3,250, 3,000, 2,750, 2,500, 2,225, 2,000, 1,750, 1,500, 1,250, 1,000, 800, 700, 600, 500, 400, 300, 200, 100, 50 $M_w$ or less (or any range between about 3,500 and about 50). In one embodiment of the invention the $M_w$ of the hydrogel base is less than that of the hydrogel strip.

The hydrogel base can be any shape, for example, square, rectangular or ovoid. The hydrogel base can have a length and width. The length can be about 0.050, 0.075 0.1, 0.5, 1, 2, 3, 4, 5, 6, 7, 8, 9, 10, 11, 12, 13, 14, 15, 20, 30, 40, 49 or more mm (or any range between about 0.05 and about 49 mm) or about 49, 40, 30, 20, 15, 14, 13, 12, 11, 10, 9, 8, 7, 6, 5, 4, 3, 2, 1, 0.5, 0.1, 0.075, 0.05 mm or less (or any range between about 49 mm and about 0.05 mm). The width of the hydrogel base can be about 0.05, 0.1, 0.5, 1, 2, 3, 4, 5, 6, 7, 8, 9, 10, 11, 12, 13, 14, 15, 20, 30, 40 or more mm (or any range between about 0.05 and about 40 mm) or about 40, 30, 20, 15, 14, 13, 12, 11, 10, 9, 8, 7, 6, 5, 4, 3, 2, 1, 0.5, 0.1, 0.05 mm or less (or any range between about 40 mm and about 0.05 mm). The width of the hydrogel strip and the hydrogel base can be same. The width of the hydrogel base can be smaller or larger than the width of the hydrogel strip. The length of the hydrogel base is shorter than the length of the hydrogel strip. The height of the base can be about 0.05, 0.1, 0.5, 1, 2, 3, 4, 5, 6, 7, 8, 9, 10, 11, 12, 13, 14, 15, 20, 30, 40 or more mm (or any range between about 0.05 and about 40 mm) or about 40, 30, 20, 15, 14, 13, 12, 11, 10, 9, 8, 7, 6, 5, 4, 3, 2, 1, 0.5, 0.1, 0.05 mm or less (or any range between about 40 mm and about 0.05 mm).

In one embodiment of the invention, the hydrogel base is coupled to the hydrogel strip in an asymmetrical manner. That is, the hydrogel base is offset from the lateral axis of the hydrogel strip. See FIG. 1F. The hydrogel base can support the hydrogel base and can be offset from the lateral axis of the hydrogel strip by about 0.05, 0.1, 0.5, 1, 2, 3, 4, 5, 6, 7, 8, 9, 10, 11, 12, 13, 14, 15, 20, or more mm (or any range between about 0.05 and about 20 mm) or about 20, 15, 14, 13, 12, 11, 10, 9, 8, 7, 6, 5, 4, 3, 2, 1, 0.5, 0.1, 0.05 mm or less (or any range between about 20 mm and about 0.05 mm). This asymmetry coupled with friction from a substrate can be used to cause movement or locomotion of the bio-bot.

The hydrogel base can have a kPa of about 50, 75, 100, 200, 300, 400, 450, 500, 550, 600, 700, 800, 900, 1,000, 1,250, 1,500, 1,750, 2,000, 2,500, 3,000 or more (or any range between about 50 and about 3,000) or about 3,000, 2,500, 2,000, 1,750, 1,500, 1,250, 1,000, 900, 800, 700, 600, 550, 500, 450, 400, 300, 200, 100, 75, 50 or less (or any range between about 3,000 and about 50). In one embodiment of the invention the kPa of the hydrogel base is greater than the kPa of the hydrogel strip.

The hydrogel strip and hydrogel base can have a swelling ratio (Q) of about 2, 4, 5, 7, 10, 12, 15, 17, 20, 22, 25, 27, 30, 32, 35, 37, 40, 42, 45 or more (or any range between about 2 and about 45) or a swelling ratio of about 45, 42, 40, 37, 35, 32, 30, 27, 25, 22, 20, 17, 15, 12, 10, 7, 5, 4, 2, or less (or any range between about 45 and about 2). The average pore size of the hydrogel strip and hydrogel base can be about 2, 3, 4, 5, 6, 7, 8, 9, 10, 11, 12, 13, 14, 15, 16, 17, 18, 19, 20, 25, 30 or more nm (or any range between about 2 and about 30 nm) or about 30, 25, 20, 19, 18, 17, 16, 15, 14, 13, 12, 11, 10, 9, 8, 7, 6, 5, 4, 3, 2 or less nm (or any range between about 30 and about 2 nm).

Cells

One or more cell types can be immobilized to any surface of a hydrogel structure of the invention (e.g., the lower surface of the hydrogel strip), present (encapsulated) within a hydrogel structure of the invention, or within the gel portion of a 3D muscle-powered bio-bots (see below). Cell types include, for example, neurons, skeletal muscle cells, cardiac muscle cells, endothelial cells, fibroblasts, or combinations thereof. Examples of other cell types that can be used include a human embryonic stem cell, a mesenchymal stem cell, a bone marrow-derived mesenchymal stem cell, a human bone marrow-derived mesenchymal stem cells a hematopoetic stem cell, a blood stem cell, an adult stem cell, an embryonic stem cell, a post-natal stem cell, a fetal cardiomyocyte, an endothelial cell, an endothelial progenitor cell, circulating angiogenic cells, circulating endothelial precursors, endothelial colony-forming cells, early outgrowth endothelial progenitor cells, late outgrowth endothelial progenitor cells, a cord blood stem cell, an autotransplanted expanded cardiomyocyte, a cardiomyocyte, a cardiac myoblast, a myofibroblast, a fibroblast, an adipocyte, a totipotent cell, a pluripotent cell, a multipotent mesenchymal stem cell, a synovial cell, a spinal disc cell, a tenocyte, a myoblast, a muscle cell, a neuron, a bone marrow cell, a mesenchymal cell, a parenchymal cell, an endothelial cell, a mesothelial cell, a fibroblast, a myofibroblast, an osteoblast, a chondrocyte, an exogenous cell, an endogenous cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell (e.g., a multi-potent progenitor cell of neurons, cardiac muscle cells, skeletal muscle cells, endothelial cells, fibroblasts), a unipotent progenitor cell, a monocyte, a skeletal myoblast, a macrophage, a capillary endothelial cell, a xenogenic cell, an allogenic cell or combinations thereof.

Muscle cells are skeletal muscle cells, cardiac muscle cells, autotransplanted expanded cardiomyocytes, cardiomyocytes, cardiac myoblasts, myofibroblasts, myoblasts, myofibroblasts, myocardial cells, multi-potent progenitor cell of muscle cells, skeletal myoblasts and muscle progenitor cells.

The cells can be immobilized onto any hydrogel structure surface of the invention (e.g., the lower surface of the hydrogel strip) in one or more distinct locations or regions. That is, cells can be immobilized in one or more distinct locations on the hydrogel surface and one more distinct locations can have no immobilized cells. In another embodiment one cell type can be present at one or more distinct locations and one or more other cell types can be present at one or more other distinct locations, with optionally one or more distinct locations with no immobilized cells. In another embodiment a mixture of two or more cells can be immobilized to one or more distinct locations and other cells (one cell type or mixture of cells) can be present at one or more other distinct locations, with optionally one or more distinct locations with no immobilized cells. The one or more cell types may also be immobilized to the hydrogel surface in an array. These one or more cell types can also be added to the pre-polymerization solution of any of the hydrogel structures of the invention such that they are present encapsulated within the hydrogel structures themselves.

In one embodiment of the invention, the one or more cell types are cardiac muscle cells and optionally, one or more other cell types such as neurons, fibroblasts, or both neurons and fibroblasts or any other cell type.

In one embodiment of the invention, endothelial cells and/or fibroblast cells can be present on or within a bio-bot along with cardiac muscle cells, skeletal muscle cells or other muscle cells. The endothelial and/or fibroblast cells can form vascular networks for muscle tissue. The endothelial and/or fibroblast cells can be present within the hydrogel structure (i.e., encapsulated with in the hydrogel), on the lower surface of the hydrogel strip or within a hydrogel layer present on the lower surface of the hydrogel surface. In one embodiment the muscle cells can be immobilized to the lower surface of the hydrogel strip and then the hydrogel layer comprising the endothelial and/or fibroblast cells can be added to the lower surface of the hydrogel strip. In another embodiment, the muscle cells and endothelial cells and/or fibroblasts are both present within (i.e., encapsulated within) a hydrogel layer present on the lower surface of the hydrogel strip. Microchannels can be present in the hydrogel strip or the hydrogel layer present on the lower surface of the hydrogel surface. See, Jeong et al., Advanced Materials 24:1 (2012). The microchannels can be about 100 µm to about 2.5 mm in diameter and have on-center spacing between the microchannels that is about 100 µm to about 2.5 mm. The microchannels can encourage neovessel formation. The endothelial and/or fibroblast cells can secrete one or more proangiogenic factors, growth factors, or antiangiogenic factors. Growth factors include, for example, vascular endothelial growth factor (VEGF) (A-F), proliferin, serpin E1, endothelin-1, fibroblast growth factors (acidic and basic FGF 1-10), granulocyte-macrophage colony-stimulating factor (GM-CSF), insulin, insulin growth factor or insulin-like growth factor (IGF), insulin growth factor binding protein (IGFBP), placenta growth factor (PlGF), angiopoietin (Ang1 and Ang2), platelet-derived growth factor (PDGF), hepatocyte growth factor (HGF), transforming growth factor (TGF-α, TGF-β, isoforms 1-3), platelet-endothelial cell adhesion molecule-1 (PECAM-1), vascular endothelial cadherin (VE-cadherin), nitric oxide (NO), chemokine (C--X--C motif) ligand 10 (CXCL10) or IP-10, interleukin-8 (IL-8), hypoxia inducible factor (HIF), monocyte chemotactic protein (MCP), such as MCP-1, vascular cell adhesion molecule (VCAM), ephrin ligands (including Ephrin-B2 and -B4); transcription factors including HIF-1α, HIF-1β and HIF-2α, Ets-1, Hex, Vezf1, Hox, GATA, LKLF, COUP-TFII, Hox, MEF2, Braf, Prx-1, Prx-2, CRP2/SmLIM and GATA family members, basic helix-loop-helix factors and their inhibitors of differentiation; and regulatory molecules including enzymes (matrix metalloproteinase (MMP) such as MMP-9, tissue plasminogen activator (PLAT or tPA), and cyclooxygenase (COX) or angiogenin. Antiangiogenic factors include, for example, endoglin, fms-like tyrosine kinase 1 (sFlt1), NRP-1, IFN-α, IFN-β, IFN-γ, CXCC10, IL-4, IL-12, IL-18, prothrombin, maspin, angiostatin, endostatin, TSP-1, TSP-2, vasostatin, platelet factor 4, or prolactin. In one embodiment of the invention one or more purified proangiogenic factors, growth factors, or antiangiogenic factors are added to the bio-bots, hydrogels, or gels or are immobilized or coupled to the bio-bots, hydrogels, or gels.

The microchannels and endothelial cells and/or fibroblast cells can provide a microvasculature for the muscle cells.

Immobilization of Cells to Hydrogel Strip

The one or more types of cells can be immobilized to a hydrogel surface (e.g., the lower surface of the hydrogel strip) by any method known in the art. In one embodiment of the invention a surface of any hydrogel surface can be coated with, for example, one or more cell-binding proteins (for example, one or more extracellular matrix proteins) to facilitate cell attachment to the hydrogel surface. Extracellular matrix proteins can be, for example types I, II, III, IV, V, VI, VII, VIII, IX, X, XII, or XII collagen, fibronectin, fibrin, fibrillin, elastin, laminin, undulin, nidogen, tenasin, vitronectin, osteonectin (SPARC), thrombospondin, biglycan, decorin, lumican, aggrecan, syndecan, perlecan, Matrigel® matrix protein mixture (Corning), Geltrex® basement membrane matrix (Life Technologies), Cultrex® (Trevingen®) basement membrane extract, Applied Cell Extracellular Matrix (ABM), polylysine and combinations thereof.

One or more cell-binding proteins can be immobilized onto the hydrogel surface (e.g., the lower surface of the hydrogel strip) in one or more distinct locations or regions. By placing the one or more cell-binding proteins in one or more distinct locations or regions, the location of cells on the hydrogel surface can be controlled. That is, the cells can be immobilized to one or more distinct locations through the cell-binding proteins. In one embodiment, cell-binding proteins can be immobilized in one or more distinct locations on the hydrogel strip and one more distinct locations can have no cell-binding proteins. In another embodiment one type of cell-binding protein can be present at one or more distinct locations and one or more other types of cell-binding proteins can be present at one or more other distinct locations, with optionally one or more distinct locations with no cell-binding proteins. In another embodiment a mixture of two or more cell-binding proteins can be immobilized to one or more distinct locations and other cell-binding proteins (one cell-binding protein type or mixture of cell-binding proteins) can be present at one or more other distinct locations, with optionally one or more distinct locations with no cell-binding proteins. The one or more cell-binding proteins types may also be coupled to the hydrogel surface in an array.

Cell binding proteins can be printed onto stamps in patterns that are placed onto a hydrogel structure (e.g., micro-contact printing) in grooves, microchannels, lines that are about 5, 10, 25, 50, 75, 100 or more μm wide, or any other pattern. See Example 10. Cells can then be seeded onto the hydrogel surfaces. The cell binding proteins can be chemically linked to a group for cross-linking to the hydrogel during polymerization. Cells can be aligned on a hydrogel structure using cell binding proteins that are aligned on the hydrogel in specific patterns.

These cell-binding proteins can also be added to the pre-polymerization solution of any of the hydrogel structures of the invention such that they are present within the hydrogel structures themselves.

Additional Proteins Immobilized to Hydrogel Surface

Any hydrogel surface of the invention (e.g., the lower surface of the hydrogel strip) can further comprise proteins or other chemicals or moieties such as cell adhesion domains, growth factors, hydrolytic polypeptides, proteolytic polypeptides including for example, Insulin growth factor type 1 (IGF-1), Nerve growth factor (NGF), basic fibroblast growth factor (b-FGF), acidic fibroblast growth factor (a-FGF), RGD peptides, RGDS peptides, RGDC peptides, KQAGDV peptides, YIGSR peptides, WSPW peptides, aminocaproic acid, aprotinin, leupeptin, pepstatin or combinations thereof. These can be immobilized or coupled to the hydrogel by any means known in the art and can be immobilized or coupled in one or more distinct locations on the hydrogel surface. These proteins can also be added to the pre-polymerization solution of any of the hydrogel structures of the invention such that they are present within the hydrogel structures themselves. Cell adhesion domains, growth factors, hydrolytic polypeptides, proteolytic polypeptides can also be directly cross-linked into the hydrogel (e.g., PEG) backbone.

Three Dimensional Muscle-Powered Bio-Bots

Another embodiment of the invention comprises a 3D muscle-powered bio-bot (also called a muscle strip bio-bot herein). In one embodiment a muscle strip bio-bot comprises two or more hydrogel pillars having top and bottom base end surfaces that are coupled to a hydrogel beam at their top base end surfaces, wherein the hydrogel beam extends between the two or more hydrogel pillars. See FIG. 3. The pillar/beam structure is a hydrogel structure of the invention. A gel comprising one or more types of cells surrounds the two or more pillars, wherein the bottom base end surfaces of the pillars are not covered or surrounded by the gel in one embodiment of the invention. The two or more hydrogel pillars can have caps on their bottom base end surfaces that are not covered or surrounded by the gel. See FIG. 4. That is, the gel extends from the hydrogel beam to within about 0.05, 0.1, 0.5, 1, 2, 3, 4, 5, 6, or more mm or about 6, 5, 4, 3, 2, 1, 0.5, 0.1, 0.05 or less mm from the bottom base surface of the pillars or the caps of the pillars. In one embodiment the gel extends from the hydrogel beam to the surface of the cap coupled to the pillar. In other embodiments the invention the bottom base end surfaces of the pillars or caps are covered by the gel. The depth of the gel from the hydrogel beam up the pillars can be about 0.05, 0.1, 0.5, 1, 2, 3, 4, 5, 6, 7, 8, 9, 10, 11, 12, 13, 14, 15, 20, 30, 40 or more mm (or any range between about 0.05 and about 40 mm) or about 40, 30, 20, 15, 14, 13, 12, 11, 10, 9, 8, 7, 6, 5, 4, 3, 2, 1, 0.5, 0.1, 0.05 mm or less (or any range between about 40 mm and about 0.05 mm). The gel surrounds the pillars and extends between the pillars such that muscle strips can form around the pillars like a rubber band. A casting device can be used to hold the liquid gel/cell/protein mixture in place until gelation occurs. See, e.g., FIG. 4.

Figure 5A:
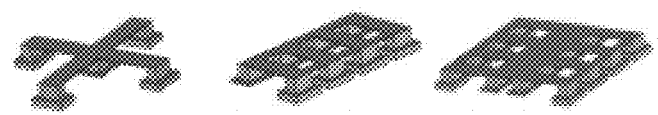
FIG. 5A-C shows design, fabrication, and simulation of multilegged designs. Due to a fabrication technology offering a great deal of flexibility in specifying geometric and design parameters, the designs presented herein demonstrate the ability to build bio-bots with varying number and arrangement of pillars.
Figure 5B:
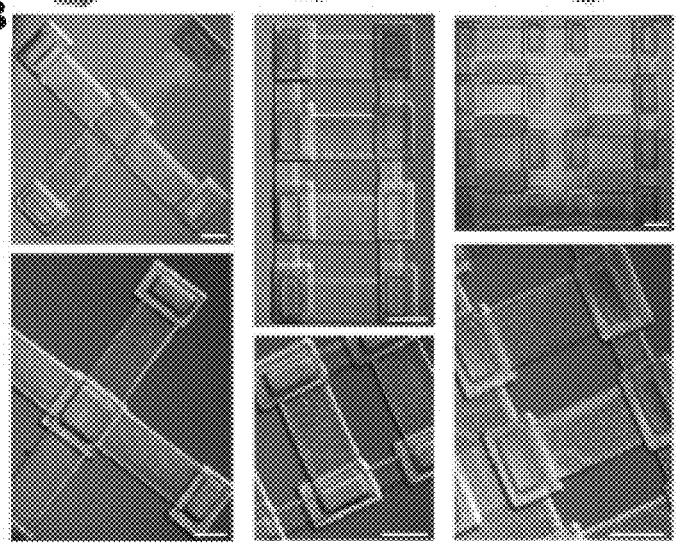
Figure 5C:
Figure 6A:
FIG. 6 shows PDMS molds (black) for micromolding of hydrogel structures (gray) that are symmetrical with one beam and one pillar (A), asymmetrical with one beam and one pillar (B), symmetrical with one beam and two pillars (C), and asymmetrical with one beam and two pillars (D).
Figure 6C:
Figure 6B:
Figure 6D:

In other embodiment of the invention 3 or more hydrogel pillars can be arranged in a row and all 3 pillars can be coupled to a hydrogel beam at the top base end surfaces of the hydrogel pillars, wherein the one or more of the hydrogel pillars are further connected via an additional hydrogel beam in one or both perpendicular directions from the row to an additional one or more pillars. The additional hydrogel beam connects the top base end surfaces of the hydrogel pillars. See, for example, FIG. 5A, first figure.

In an additional embodiment, hydrogel pillars are arranged in rows and columns within a grid-like array with one or more rows of hydrogel pillars and one or more columns of hydrogel pillars. Each row of hydrogel pillars can be connected at the top base end surfaces of the hydrogel pillars by a hydrogel beam and wherein each column of hydrogel pillars is connected at the top base end surfaces of the hydrogel pillars by a hydrogel beam. See, for example, FIG. 5A, second figure. The hydrogel beams intersect at the top base end surfaces of the hydrogel pillars, but are not a "double" thickness at this intersection. That is, the grid of beams connecting the pillars can be of a uniform thickness.

In another embodiment a multitude of hydrogel pillars having top and bottom base end surfaces are arranged in rows and columns within a grid-like array with one or more rows of hydrogel pillars and one or more columns of hydrogel pillars. Each row of hydrogel pillars is connected at the top base end surfaces of the hydrogel pillars by a hydrogel base, wherein the hydrogel base connects all the hydrogel pillars. The rows can have consistent spacing or each row can be a different distance from the next row. Additionally, the columns can have consistent spacing or each column can be a different distance from the next column. Besides connecting each column of pillars the hydrogel base can additionally fully cover the areas between one or more columns. See for example, FIG. 5A, third figure (where the hydrogel beam connects columns 1-4 and also the area between columns 3 and 4). Additionally, besides connecting each row of pillars the hydrogel base can additionally fully cover the areas between one or more rows. A gel comprising one or more types of cells can surround the two or more pillars, wherein the bottom base end surfaces of the pillars are not covered by the gel. The bottom base end surfaces of the pillars can comprise caps that are not covered or surrounded by the gel. In another embodiment, the bottom base end surfaces of the pillars or caps can be covered by the gel.

Pillars and Caps of Three Dimensional Muscle Powered Bio-Bot

The pillars, caps and beams of the 3D muscle-powered bio-bot can be made of a hydrogel as described in detail above for the hydrogel strip and base (cantilever) bio-bots.

One or more of the hydrogel pillars can have a different height than the other hydrogel pillars. Additionally or alternatively, one or more of the caps can have a different thickness than the other caps. These alternative heights and thicknesses will provide asymmetry for one type of locomotion of the bio-bot. In one embodiment of the invention, at least half of the pillars or caps will be higher or thicker than the other half of pillars and caps. The bio-bot will locomote toward the direction of the higher/thicker pillars and caps.

A hydrogel pillar can be any shape, for example, square, rectangular or ovoid. A hydrogel pillar can have a length, width, and height. See FIG. 3. The length and width can be about 0.050, 0.075 0.1, 0.5, 1, 2, 3, 4, 5, 6, 7, 8, 9, 10, 11, 12, 13, 14, 15, 20, 30, 40, 49 or more mm (or any range between about 0.05 and about 49 mm) or about 49, 40, 30, 20, 15, 14, 13, 12, 11, 10, 9, 8, 7, 6, 5, 4, 3, 2, 1, 0.5, 0.1, 0.075, 0.05 mm or less (or any range between about 49 mm and about 0.05 mm). The width of the hydrogel strip and the hydrogel beam can be same or the width of a hydrogel pillar can be smaller or larger than the width of the hydrogel beam. The height of a pillar can be about 0.05, 0.1, 0.5, 1, 2, 3, 4, 5, 6, 7, 8, 9, 10, 11, 12, 13, 14, 15, 20, 30, 40 or more mm (or any range between about 0.05 and about 40 mm) or about 40, 30, 20, 15, 14, 13, 12, 11, 10, 9, 8, 7, 6, 5, 4, 3, 2, 1, 0.5, 0.1, 0.05 mm or less (or any range between about 40 mm and about 0.05 mm).

A cap can be coupled to the bottom base surface of a pillar and can be any shape, for example, square, rectangular or ovoid. The cap has a length, width, and a thickness. The length and the width of the cap are each greater than the length and width of the pillar to which it is coupled. The length and width of the cap can be about 0.060, 0.075 0.1, 0.5, 1, 2, 3, 4, 5, 6, 7, 8, 9, 10, 11, 12, 13, 14, 15, 20, 30, 40, or more mm (or any range between about 0.06 and about 40 mm) or about 40, 30, 20, 15, 14, 13, 12, 11, 10, 9, 8, 7, 6, 5, 4, 3, 2, 1, 0.5, 0.1, 0.075, 0.06 mm or less (or any range between about 40 mm and about 0.06 mm). The thickness of the cap can be about 50, 60, 70, 80, 90, 100, 125, 150, 175, 200, 225, 250, 275, 300, 325, 350, 375, 400, 425, 450, 475, 500, 525, 550, 575, 600, 650, 700, 750 µm or more (or any range between about 50 and about 750 µm) or 750, 700, 650, 600, 575, 550, 525, 500, 475, 450,425, 400, 375, 350, 325, 300, 275, 250, 225, 200, 175, 150, 125, 100, 90, 80, 70, 60, 50 µm or less (or any range between about 750 and about 50 µm). In one embodiment of the invention all pillars have a cap on their bottom base surfaces.

A 3D muscle-powered bio-bot can have two or more pillars (e.g. 2, 3, 4, 5, 6, 7, 8, 9, 10, 15, 20, 26, 30, 36, 40, 46, 50 or more (or any range between about 2 and 50 pillars), which can be separated by about 0.1, 0.5, 1, 2, 3, 4, 5, 6, 7, 8, 9, 10, 15, 20, 25, 30, 40, 45, 50 mm or more (or any range between about 0.1 and about 50 mm) or about 50, 40, 30, 25, 20, 15, 10, 9, 8, 7, 6, 5, 4, 3, 2,1, 0.5, 0.1 mm or less (or any range between about 50 and about 45 mm) as measured between the outer edges of the pillars (see FIG. 3).

Three Dimensional Muscle Powered Bio-Bot Beams

A hydrogel beam can be any shape or size, including for example, rectangular, ovoid, triangular, or circular. The hydrogel beam can be, in general, an elongated shape. The hydrogel beam has an upper and lower surface. The upper and lower surfaces can be generally smooth or can be textured or nanotextured. Examples of surface textures include ridges, hills, grooves, mesas/plateaus, terraces, trenches, surface pores, and so forth. Nanotextures have at least one dimension that is less than 100 nm in length. For example, a ridge or trench that is 10 nm wide by 50 microns long is a nanostructure, because it is has at least one dimension (e.g., its width), which is less than 100 nm in length.

In one embodiment the hydrogel beam is an elongated shape such as rectangular shape with a length, width, and a thickness. The length of the elongated strip is greater than the width. The length of the hydrogel beam can be about 0.075, 0.1, 0.5, 1, 2, 3, 4, 5, 6, 7, 8, 9, 10, 11, 12, 13, 14, 15, 20, 30, 40, 50 or more mm (or any range between about 0.075 and about 50 mm) or about 50, 40, 30, 20, 15, 14, 13, 12, 11, 10, 9, 8, 7, 6, 5, 4, 3, 2, 1, 0.5, 0.075 mm or less (or any range between about 50 mm and about 0.075 mm).

The width of the beam can be about 0.05, 0.1, 0.5, 1, 2, 3, 4, 5, 6, 7, 8, 9, 10, 11, 12, 13, 14, 15, 20, 30, 40 or more mm (or any range between about 0.05 and about 40 mm) or about 40, 30, 20, 15, 14, 13, 12, 11, 10, 9, 8, 7, 6, 5, 4, 3, 2, 1, 0.5, 0.1, 0.05 mm or less (or any range between about 40 mm and about 0.05 mm). The thickness of the beam can be about 50, 60, 70, 80, 90, 100, 125, 150, 175, 200, 225, 250, 275, 300, 325, 350, 375, 400, 425, 450, 475, 500, 525, 550, 575, 600, 650, 700, 750 µm or more (or any range between about 50 and about 750 µm) or 750, 700, 650, 600, 575, 550, 525, 500, 475, 450,425, 400, 375, 350, 325, 300, 275, 250, 225, 200, 175, 150, 125, 100, 90, 80, 70, 60, 50 µm or less (or any range between about 750 and about 50 µm).

The hydrogel pillars, beams and caps can be made of a hydrogel, such as a photopolymerizable hydrogel (e.g. PEGDA) of weight average molecular weight ($M_w$) of about 100, 200, 300, 400, 500, 700, 1,000, 1,250, 1,500, 1,750, 2,000, 2,225, 2,500, 2,750, 3,000, 3,250, 3,400, 3,500, 3,750, 4,000, 4,250, 4,500, 4,750, 5,000, 5,250, 5,500, 5,750, 6,000, 6,250, 6,500, 6,750, 7,000, 7,250, 7,500, 7,750, 8,000 $M_w$ or more (or any range between about 100 and about 8,000 $M_w$) or 8,000, 7,750, 7,500, 7,250, 7,000, 6,750, 6,500, 6,250, 6,000, 5,750, 5,500, 5,250, 5,000, 4,750, 4,500, 4,250, 4,000, 3,750, 3,500, 3,400, 3,250, 3,000, 2,750, 2,500, 2,225, 2,000, 1,750, 1,500, 1,250, 1,000, 700, 500, 400, 300, 200, 100 $M_w$ or less (or any range between about 8,000 or about 100 $M_w$). The weight average molecular weight of the pillars, beams and caps of a hydrogel structure can all be the same or they can be different for each of the pillars, beams and caps.

The elastic moduli of the pillars, beams and caps can be about 100, 200, 300, 400, 500, 600, 700, 800, 900, 1,000 kPa or more (or any range between about 100 and about 1,000 kPa) or about 1,000, 900, 800, 700, 600, 500, 400, 300, 200, 100 kPa or less (or any range between about 1,000 and about 100 kPa).

Cells and Gel of Three Dimensional Muscle Cell Powered Bio-Bot

One or more types of cells and a solution capable of forming a gel are added to the hydrogel pillar and beam structure (see in one example, FIG. 4). The gel solution can comprise one or more extracellular matrix proteins, for example, Extracellular matrix proteins can be, for example types I, II, III, IV, V, VI, VII, VIII, IX, X, XII, or XII collagen, fibronectin, fibrin, fibrillin, elastin, laminin, undulin, nidogen, tenasin, vitronectin, osteonectin (SPARC), thrombospondin, biglycan, decorin, lumican, aggrecan, syndecan, perlecan, Matrigel® matrix protein mixture (Corning), Geltrex® basement membrane matrix (Life Technologies), Cultrex® (Trevingen®) basement membrane extract, Applied Cell Extracellular Matrix (ABM), polylysine or combinations thereof. In one embodiment of the invention the gel comprises Collagen I, collagen IV, laminin, and entacin. The concentration of collagen can be about 0.2, 0.5, 0.8, 1.0, 1.2, 1.4, 1.8, 2.0, 2.5, 3.0, 3.5, 4.0 or mg/ml$^{-1}$.

In one embodiment of the invention, the gel can further comprise proteins or other chemicals or moieties such as cell adhesion domains, growth factors, hydrolytic polypeptides, proteolytic polypeptides including for example, Insulin growth factor type 1 (IGF-1), Nerve growth factor (NGF), basic fibroblast growth factor (b-FGF), acidic fibroblast growth factor (a-FGF), RGD peptides, RGDS peptides, RGDC peptides, KQAGDV peptides, YIGSR peptides, WSPW peptides, aminocaproic acid, aprotinin, leupeptin, pepstatin or combinations thereof.

In one embodiment of the invention, a protease inhibitor can be added to the gel and cell solution mixture. Protease inhibitors include, for example, ε-aminocarproic acid or aprotinin. The protease inhibitor can be added at about 0.1, 0.5, 1.0, 2.5, 5, 7, 10 or more mg/mL.

In the 3D muscle cell powered bio-bot at least one of the cell types are skeletal muscle cells, cardiac muscle cells, myoblasts or muscle progenitor cells. Other cell types can include, for example, all the cells listed above for the hydrogel strip and base (cantilever) bio-bot. In one embodiment of the invention, the one or more cell types comprise neurons and muscle cells, wherein the muscle cells form one or more muscle fibers and wherein the neurons and muscle fibers comprise one or more neuromuscular junctions.

In one embodiment of the invention, endothelial cells and/or fibroblast cells can be present along with cardiac muscle cells, skeletal muscle cells or other muscle cells. The endothelial and/or fibroblast cells can form vascular networks for muscle tissue. The endothelial and/or fibroblast cells can be present within the gel along with the muscle cells. Microchannels can be present in the hydrogel beam or the gel. See, Jeong et al., *Advanced Materials* 24:1 (2012). The microchannels can be about 100 μm to about 2.5 mm in diameter and have on-center spacing between the microchannels that is about 100 μm to about 2.5 mm. The endothelial and/or fibroblast cells can secrete one or more proangiogenic factors, growth factors, or antiangiogenic factors. The microchannels and endothelial cells and/or fibroblast cells can provide a microvasculature for the muscle cells.

In one embodiment of the invention, the one or more cell types include muscle cells and the gel comprising the one or more types of cells is polymerized and condensed around the pillars to form a solid muscle strip.

The cells can be present in the gel at a cell concentration of about $1\times10^2$, $1\times10^3$, $1\times10^4$, $2.5\times10^4$, $5\times10^4$, $1\times10^5$, $2.5\times10^5$, $5\times10^5$, $1\times10^6$, $2.5\times10^6$, $5\times10^6$, $1\times10^7$, $2.5\times10^7$, $5\times10^7$, $1\times10^8$, $2.5\times10^8$, $5\times10^8$ or more cells ml$^{-1}$.

Locomotion

In one embodiment of the invention, a bio-bot is capable of actuation, directional locomotion, controlled directional locomotion, or combinations thereof. Actuation is defined as the conversion of some form of energy into a mechanical output. Locomotion is a subset of actuation.

In one embodiment the bio-bots exhibit directional locomotion due to muscle cell contraction coupled with asymmetry present within the structure of the hydrogel strip and base, e.g., the offset nature of the base from the lateral axis of the hydrogel strip to which it is coupled. The hydrogel base of the bio-bot can be placed on a substrate providing friction between the substrate and the hydrogel base. For the 3D muscle powered bio-bots asymmetry resulting from different heights of one or more pillars or different thicknesses of one or more caps can result in locomotion. Friction between the base and the substrate upon which the bio-bot sits is important for locomotion. Friction can adjusted by, for example, changing the thickness of the caps, the heights of the pillars, the weight of the bio-bot, the viscosity of the medium present under or around the bio-bot, or the surface of the substrate. A bio-bot can locomote when the force produced by the muscle strips or cells of the bio-bot can overcome the friction force between the base, pillars or caps and the substrate. Friction force is not affected by contact area on the macro-scale, but instead on the micro-scale. Friction on the macro-scale is a function of the normal force (or weight of the bio-bot device—which can be modified) and by the coefficient of friction (which is a function of the two interacting materials—which in this case is the hydrogel bio-bot and the substrate, e.g., a plastic dish lubricated with medium).

Additionally, locomotive behavior of bio-bots can be regulated by, for example, illumination with light of specific wavelengths, by application of an electric current, by a chemical compound, or combinations thereof. Controlled bidirectional locomotion can be achieved in any X-Y direction on a substrate, including rotation around the Z-axis. Additionally, starting, stopping and altering the speed of the locomotion is possible. Modulation of the frequency or intensity of optical pulses, frequency or amplitude of electrical stimulation, or chemical gradient can alter speed of bio-bot locomotion.

Optical methods have been developed to depolarize or hyperpolarize neurons using specific wavelengths of light. Boyden et al., *Nat. Neurosci.* 8, 1263-1268 (2005); Arenkiel et al., *Neuron* 54, 205-218 (2007); Wang et al. *Proc. Natl. Acad. Sci. USA* 104, 8143-8148 (2007). This method, known as 'optogenetics', combines the temporal and spatial precision of light pulses with cellular specificity of genetic targeting. The general strategy of optogenetics involves introducing a light-sensitive protein, such as channelrhodopsin-2 (ChR2, from e.g., green algae) to a specific cell type, illuminating the cells with defined spatiotemporal parameters, and obtaining reliable readout of the cellular behavior. Deisseroth, *Nat. Methods* 8, 26-29 (2011). This method can be used in cardiac (Bruegmann et al. *Nat. Methods* 7, 897-900 (2010); Arrenberg et al., *Science* 330, 971-974 (2010)) and skeletal (Asano et al., *Biotechnol. Bioeng.* 109, 199-204 (2012); Sakar et al. *Lab Chip* 12, 4976-4985 (2012)) muscle cells to rhythmically control their contractions. It can also be used to locally innervate specific regions of muscle tissue to generate movement in multiple degrees of freedom (multi-DOF). Optogenetics is its fast, precise, and provides local stimulation of cells and tissues, relative to electrical stimulation. Moreover, it does not require complex heterotypic cell-cell interactions that are needed for neuromuscular (neuron-to-muscle) junctions. Umbach et al., *PLoS One* 7, e36049 (2012); Kubo et al. *Plast. Reconstr. Surg.* 123, 139S-148S (2009).

Therefore, in some embodiments of the invention, polynucleotides that express one or more light-sensitive proteins are introduced into one or more specific cell types (e.g., cardiac or skeletal muscle cells, neurons, endothelial cells, fibroblasts) by methods not limited to transfection, electroporation, or microinjection. Cells comprising light-sensitive proteins are subsequently integrated into a bio-bot as described herein. Non-limiting examples of light-sensitive proteins include channelrhodopsin, e.g., channelrhodopsin-1 (ChR1), channelrhodopsin-2 (ChR2), melanopsin, photopsin, rhodopsin, UV-B resistance 8 (UVR8), cryptochrome, phototropin, phytochrome, chlamyopsin, volvoxopsin, and bacteriophytochrome. The entire bio-bot construct can be stimulated by illumination with defined spatiotemporal parameters, or illumination can be targeted to a specific portion of the bio-bot construct. Stimulation of bio-bots can occur upon illumination with visible light or ultraviolet light. In some embodiments, bio-bots fabricated with cells comprising ChR2 are illuminated with blue light (approximate wavelength of 450-495 nm).

Bio-bots can be also stimulated with a bipolar electrical pulse train. Electrical field pulses can be up to 50 volts per cm (e.g., about 50, 40, 30, 20, 10, 5, 3, 2, or less volts per cm) and of pulse widths of a few seconds or less (e.g. about 5, 4, 3, 2, 1, 0.5, 0.1, 0.01 seconds or less). Stimulation frequencies can be up to 10 Hz or frequencies up to when tetanus can result (e.g. about 20, 15, 10, 9, 8, 7, 6, 5, 4, 3, 2, 1 or less Hz). Stimulation frequencies should be kept below the frequency that causes tetanus.

In some embodiments, an electric current is applied perpendicularly to the long axis of the bio-bot. The entire bio-bot can be stimulated by electric current, or the electric current can be targeted to a specific portion of the bio-bot. A localized electrical field can be applied to control the path of a symmetrical or asymmetrical bio-bot.

Bio-bots can be driven by a chemical energy source. In some embodiments, bio-bots convert glucose into mechanical energy. For bio-bots comprising neuronal and muscle cells, the genetic machinery of the neurons can be reprogrammed to regulate chemical secretions, which can be used to stimulate muscle cells to propel the bio-bot.

Bio-bots can be fabricated to move toward or away from a chemical gradient, chemoattractant, or chemorepellent. Bio-bots can be fabricated with one or more chemoreceptors for a specific chemoattractant or chemorepellent. Bio-bots may be fabricated with cells comprising specific chemoreceptors, or bio-bots may be fabricated with chemoreceptor protein preparations. Non-limiting examples of receptors for include G protein-coupled receptors (GPCRs) and histidine kinase-coupled receptors (HKCRs). For example, a bio-bot comprising a receptor for a specific toxin can be stimulated to move toward the toxin. The bio-bot can subsequently release one or more chemicals to neutralize the toxin. One of more type of cells present on or within the bio-bots can be used as "factories" to generate and secrete certain chemicals or proteins. It is possible to stimulate cells to release certain factors, both biological and non-natural or recombinant.

In one embodiment of the invention, the addition of isoproterenol (β-agonist) or carbamylcholine chloride (cholinergic agonist) will increase or decrease contraction frequency of muscle cell sheets, respectively. Heptanol is a gap junction blocker that will reversibly stop synchronous contraction. Pulsatile electrical stimulation can also be used to induce and pace the muscle cells.

The invention provides methods of controlling the directional locomotion of the bio-bots comprising exposing the entire bio-bot or a selected portion of the bio-bot to light, an electrical pulse, or a chemical. A selected portion can be, for example, a distinct location of the hydrogel strip, part of the hydrogel strip, one or more pillars, one or muscle strips, or one or more portions of a muscle strip. The reaction of the cells in the bio-bot will control the directional locomotion of the bio-bot. Controlling directional locomotion of the bio-bot includes starting locomotion, stopping locomotion, slowing locomotion, accelerating locomotion, changing the direction of locomotion, or combinations thereof.

Method of Making Locomotive Biological Machines

A locomotive biological machine can be made by any methods known in the art. In one embodiment of the invention, the hydrogel structures of locomotive biological machines can be made using, for example, an SLA. A stereo-lithographic apparatus (SLA) is a rapid prototyping tool used to produce 3D models, prototypes, and patterns by repetitive deposition and processing of individual layers. It uses an ultraviolet laser (at, for example, 325 nm) to directly write on and polymerize photosensitive liquid materials based on a computer-aided design (CAD)-based digital blueprint, sliced into a collection of 2D cross-sectional layers, and processed into a real 3D part using layer-by-layer polymerization. The thickness of each layer can be about 25, 50, 75, 100, 125, 150, 175, 200 or more μm (or any range between about 25 and 200 μm) or about 200, 175, 150, 125, 100, 75, 50, 25 or less μm (or any range between about 100 and 20 μm). The automated, high-throughput process can be particularly useful for the development of cellular systems due to its multi-material capability, which has been used with photopolymerizable hydrogels to pattern cells or proteins at precise locations on the structure. Because of their excellent spatial control, it is possible to create 3D structures with multi-cellular components that are required for complex tissue function.

A hydrogel solution, such as a photopolymerizable hydrogel and a photoinitiator can be added to a culture dish at specific volumes and at specific positions. Photoinitiators can be, for example, 1-[4-(2-hydroxyethoxy)-phenyl]-2-hydroxy-2-methyl-1-propane-1-one (Irgacure 2959), 1-hydroxy-cyclohexyl-phenyl-ketone (Irgacure 184), 2-hydroxy-2-methyl-1-phenyl-1-propanone (Darocur 1173), methybenzoylformate (Darocur MBF), oxy-phenyl-acetic acid 2-[2 oxo-2 phenyl-acetoxy-ethoxy]-ethyl ester and oxyphenyl-acetic 2-[2-hydroxy-ethoxy]-ethyl ester (Irgacure 754), alpha, alpha-dimethoxy-alpha-phenylacetopheone (Irgacure 651), 2-benzyl-2-(dimethylamino)-1-[4-(4-morpholinyl)-1-propanone (Irgacure 369), 2-Methyl-1-[4-(methylthio)phenyl]-2-Methyl-1-[4-(methylthio)phenyl] (Irgacure 907), Phosphine oxide, phenyl bis (2,4,6)-trimethyl benzoyl) (Irgacure 819), Bis (eta 5-2,4-cyclopentadien-1-yl) (Irgacure 784), Idonium (Irgacure 250), acetophenone, anisoin, anthraquinone, anthraquinone-2-sulfonic acid, (benzene) tricarbonylchromium, benzyl, benzoin, benzoin ethyl ether, benzoin isobutyl ether, benzoin methyl ether, benzophenone, 3,3',4,4'-benzophenonetetracarboxylic dianhydride, 4-benzolbiphenyl, 2-benzyl-2-(dimethylamino)-4'-morpholinobutyrophenone, 4,4'-bis(diethylamino)benzophenone, 4,4'-bis(methylamino)benzophenone, camphorquinone, 2-chlorothioxanthen-9-one (cumene) cyclopentadienyliron (ii) hexafluorophosphate, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone, 3,4-dimethylbenzophenone, diphenyl(2,4,6-trimethylbenzoyl)phosphine oxide, 4'-ethoxyacetophenone, 2-ethylantraquinone, ferrocene, 3'-hydroxyacetophenone, 4'-hydroxyacetophenone, 3-hydroxyacetophenone, 4-hydroxyacetophenone, 1-hydroxy-2-methylpropiophenone, 2-methylbenzophenone, 3-methylbenzophenone, 2-methyl-4'-(methylthio)-2-morpholinopropiophenone, phenanthrenequinone, 4'-phenoxyacetophenone, thioxanthen-9-one, triarylsulfonium hexafluoroantimonate, triarylsulfonium hexafluorophosphate or combinations thereof.

One or more types of cells, one or more cell-binding proteins, one or more additional proteins (as all described above) or combinations thereof can be added to the prepolymerization solution of any of the hydrogel structures of the instant invention.

An ultraviolet laser beam can be used to selectively cross-link the hydrogel strip and hydrogel base structures or pillar and beam structures at specified energy doses. The energy doses of the laser can be varied by controlling the scan speed. Laser exposure energies can be about 50, 100, 150, 200, 250, 300, 350, 400, 450, 500, 550, 600, 650, 700, 750, 800, 850, 950, 1,000 mJ $cm^{-1}$ or more (or any range between about 50 and about 1,000) or about 1,000, 950, 900, 850, 800, 750, 700, 650, 600, 550, 500, 450, 400, 350, 300, 250, 200, 150, 100, 50 mJ $cm^{-1}$ or less (or any range between about 1,000 and about 50). Other cross-linkers include, for example, N-Sulfosuccinimidyl-6-(4'-azido-2'-nitrophenylamino) hexanoate (Sulfo-SANPAH), N-5-

Azido-2-nitrobenzoyloxysuccinimide, NHS-Diazirine (SDA), dimethyl adipimidate (DMA), dimethyl pimelimidate (DMP), dimethyl suberimidate (DMS), dithiobispropionimidate (DTBP), Bis[sulfosuccinimidyl] suberate (BS3), Bis[2-(succinimidooxycarbonyloxy)ethyl]sulfone (BSOCOES), Disuccinimidyl glutarate (DSG), Dithiobis[succinimidyl propionate] (DSP), Disuccinimidyl suberate (DSS), Disuccinimidyl tartarate (DST), 3,3'-Dithiobis[sulfosuccinimidylpropionate] (DTSSP), Ethylene glycol bis[succinimidylsuccinate] (EGS), Ethylene glycol bis[sulfosuccinimidylsuccinate] (Sulpho-EGS), Tris-succinimidyl aminotriacetate (TSAT), 1-Ethyl-3-[3-dimethylaminopropyl]carbodiimide hydrochloride (EDC), N-hydroxysuccinimide (NHS), (N-hydroxysulfosuccinimide) (Sulfo-NHS), dicyclohexylcarbodiimide (DCC), Sulfosuccinimidyl (4-iodoacetyl)aminobenzoate (Sulfo-SIAB), Succinimidyl (4-iodoacetyl)aminobenzoate (SIAB), Succinimidyl 3-(bromoacetamido)propionate (SBAP), Succinimidyl iodoacetate (SIA), Sulfosuccinimidyl 4-(N-maleimidomethyl)cyclohexane-1-carboxylate (Sulfo-SMCC), Succinimidyl 4-(N-maleimidomethyl)cyclohexane-1-carboxylate (SMCC), Succinimidyl 4-(N-maleimidomethyl)cyclohexane-1-carboxy-(6-amidocaproate) (LC-SMCC), N-epsilon-Maleimidocaproyl-oxysulfosuccinimide ester (Sulfo-EMCS), N-epsilon-Malemidocaproyl-oxysuccinimide ester (EMCS), N-gamma-Maleimidobutyryl-oxysulfosuccinimide ester (Sulfo-GMBS), N-gamma-Maleimidobutyryl-oxysuccinimide ester (GMBS), N-kappa-Maleimidoundecanoyl-oxysulfosuccinimide ester (Sulfo-KMUS), m-Maleimidobenzoyl-N-hydroxysulfosuccinimide ester (Sulfo-MBS), m-Maleimidobenzoyl-N-hydroxysuccinimide ester (MBS), Succinimidyl 4-(p-maleimidophenyl)butyrate (SMPB), Sulfo-SMPB, N-alpha-Maleimidoacet-oxysuccinimide ester (AMAS), N-beta-Maleimidopropyl-oxysuccinimide ester (BMPS), Succinimidyl 6-[(beta-maleimidopropionamido) hexanoate] (SMPH), Succinimidyl-3-(2-pyridyldithio)propionate (SPDP), Sulfosuccinimidyl 6-[3'-(2-pyridyldithio) propionamido]hexanoate (Sulfo-LC-SPDP), 4-Succinimidyloxycarbonyl-alpha-methyl-alpha(2-pyridyldithio)toluene (SMPT), N-beta-Maleimidopropionic acid hydrazide (BMPH), N-epsilon-Maleimidocaproic acid hydrazide (EMCH), N-kappa-Maleimidoundecanoic acid hydrazide (KMUH), 4-(4-N-Maleimidophenyl)butyric acid hydrazide (MPBH), 3-(2-Pyridyldithio)propionyl hydrazide (PDPH), p-Maleimidophenyl isocyanate (PMPI), 1,4-Bismaleimidobutane (BMB), Bismaleimidohexane (BMH), Bismaleimidoethane (BMOE), Dithiobismaleimidoethane (DTME), Tris(2-maleimidoethyl)amine (TMEA) or combination thereof.

The elevator on the 3D printer can be used to cross-link the hydrogel in all directions. For the hydrogel strip and base bio-bots (cantilever bio-bots) the hydrogel strip can be fabricated first and then the base can be fabricated onto the hydrogel strip. The fabricated hydrogel strip and base can then be flipped over so that the hydrogel base is supporting the hydrogel strip. One or more types or molecular weights of hydrogels can be used in one hydrogel strip, hydrogel base or bio-bot by removing uncross-linked hydrogel solution and adding different hydrogel solution to the structure as it is constructed. When the hydrogel structure is completed the structure can be rinsed to remove all uncross-linked pre-polymer solution.

With the hydrogel base up and the hydrogel strip resting on a surface (as fabricated) the lower surface of the hydrogel strip (which is facing up as fabricated) can be functionalized with one or more cell-binding proteins or other proteins or chemical moieties.

Similar to the methods of making the bio-bots described above, an SLA apparatus can also be used to make 3D muscle powered bio-bots. A pre-polymer solution of a polymer and photoinitiator can be pipetted onto a substrate. See, e.g., FIG. 4. A laser beam can be used to selectively cross-link the structures into the hydrogel pillar and beam structures described above as described for the hydrogel strip and beam (cantilever) bio-bots. One or more types of cells are mixed with a gel solution comprising one or more extracellular matrix proteins and growth medium and added to the pillar and beam assembly. One of the types of cells are cardiac muscle cells, skeletal muscle cells, myoblasts, or other muscle progenitor cells. The gel and cell solution is allowed to gel. Cell growth medium can be added after gelation. In one embodiment of the invention, the cells are myoblasts and after allowing for cell growth in the gel, the myoblasts can be induced to differentiate. Insulin-like growth factor-1 (e.g., about 20, 30, 40, 50, 60, 70, 80, 90, 100 or more ng/ml$^{-1}$ and/or protease inhibitors (e.g., about 0.1, 0.5, 1.0, 2.5, 5, 7, 10 or more mg/mL can also be added to the gel within the hydrogel structures. Other types of cells can also be induced to differentiate within the gel.

Bio-bot constructs can also be fabricated by micromolding. Molds, such as polydimethylsiloxane (PDMS) for bio-bots can be fabricated on a silicon master with SU-8 negative photoresist, as described by Chen et al., 1998, *Biotechnol. Prog.* 14: 356-363; Kane et al., 1999, *Biomaterials*, 20:2363-76. Master molds can be silanized with (tridecafluoro-1,1,2,2-tetrahydrooctyl)-1-trichlorosilane in vacuum. In some embodiments, molds are generated by pouring 1:10 curing agent to polymer onto the silicon wafer. Upon curing, a negative of the pattern from the silicon master is imprinted on the surface of the PDMS to make a bio-bot mold. Pre-polymer solution (e.g. PEGDA) comprising a photoinitiator is then applied to the PDMS molds. A coverslip can be placed over the pre-polymer solution prior to polymerization. The pre-polymer solution is then cross-linked by exposure to UV irradiation. Thereafter, the bio-bots are removed from the molds and hydrated.

Bio-bots of varying structures can be fabricated by micromolding. FIG. 6 shows exemplary molds for (a) a symmetrical bio-bot with a beam and a pillar, (b) an asymmetrical bio-bot with a beam and a pillar, (c) a symmetrical bio-bot with a beam and two pillars, and (d) an asymmetrical bio-bot with a beam and two pillars. The PDMS molds are depicted in black, and the bio-bots are depicted in gray.

Cells (e.g. cardiac or skeletal muscle cells, neurons, endothelial cells, fibroblasts) or proteins (as described above) can be suspended in pre-polymer solution prior to polymerization in PDMS molds. Conversely, cells or proteins can be seeded onto the bio-bots following polymerization. In some embodiments, a suspension of cells and one or more ECM proteins (e.g., collagen or fibrin) are added around the pillars of a bio-bot fabricated by micromolding and polymerized via gelation of the one or more ECM proteins.

Drug Assays

The effect of a test agent on overall cell or tissue function may be missed by screening for effects on stationary, 2D cell culture. In one embodiment of the invention the bio-bots of the invention can be used to monitor the effect of drugs or test regents on the one or more cell types or the bio-bots themselves. The invention provides a method of detecting the response of the one or more types of cells or the bio-bot as a whole to one or more test agents comprising contacting a bio-bot of the invention with the one or more test agents and detecting or monitoring one or more of the following parameters: cell death, cell viability, number of cells, apoptosis, cell proliferation, contractile responses of the cells, angiogenesis, movement of the bio-bot, directional locomotion of the bio-bot.

These parameters can be compared to known values for other test reagents (e.g. test regents that are known to affect the cells or bio-bots parameters) or to control assays (e.g., similar cells or bio-bots that are not treated with the test reagent).

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1: Preparation and Characterization of Hydrogels for Stereolithography Poly(ethylene glycol) diacrylates (PEGDAs) of $M_w$ 700 Da (Sigma Aldrich, St Louis, Mo., USA), 3,400, 5,000, and 10,000 Da (Laysan Bio, Arab, Ala., USA) were dissolved in DMEM without phenol red (Gibco, Carlsbad, Calif., USA) to form a 40% (w/v), or 2×, pre-polymer solution. The photoinitiator, 1-[4-(2-hydroxyethoxy)-phenyl]-2-hydroxy-2-methyl-1-propane-1-one (Irgacure 2959, Ciba, Tarrytown, N.Y., USA), was dissolved in dimethyl sulfoxide (DMSO, Fisher Scientific, Springfield, N.J., USA) at 50% (w/v) stock solution and added to the 2× pre-polymer solution to form 1.0% (w/v) of photoinitiator. Medium (with or without cells) and 20% fetal bovine serum (FBS, Sigma Aldrich, St Louis, Mo., USA) were added to the pre-polymer solution in a 1:1 volumetric ratio prior to each SLA run. The final pre-polymer solution consisted of 20% (w/v) PEGDA, 0.5% (w/v) photoinitiator, and 10% FBS in DMEM without phenol red.

Figure 7A:
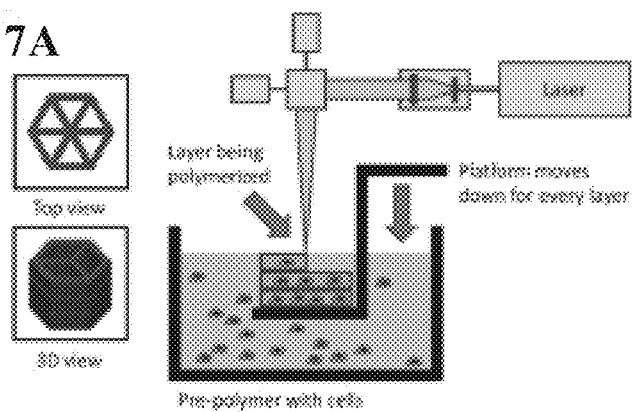
FIG. 7 is a schematic of the (A) "top-down" and (B) "bottom-up" approaches for hydrogel polymerization. In the top-down approach, the layout consists of a platform immersed just below the surface of a large tank of pre-polymer solution. After the layer is photopolymerized, the platform is lowered a specified distance to recoat the part with a new layer.
FIG. 7B: In the bottoms-up approach, the pre-polymer solution is pipetted into the container one layer at a time from the bottom to the top. This setup was modified especially for cell encapsulation applications, which required: (1) reduction in total volume of photopolymer in use, and (2) removal of photopolymer from static conditions that cause cells to settle.
Figure 7B:
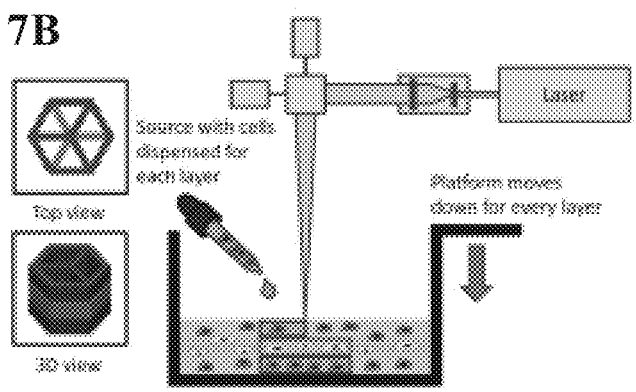

A stereolithography apparatus (SLA, Model 250/50, 3D Systems, Rock Hill, S.C., USA) was used for all experiments. Two fabrication methods were tested: a "top-down" approach and a "bottom-up" approach. For the "top-down" approach, the standard vat and platform were removed to allow for low volume material, including those containing cells. A smaller custom-made mini-platform was fabricated and screwed into an aluminum shaft that was clamped to the elevator of the SLA. The platform of the SLA was immersed just below the surface of a container of pre-polymer solution (FIG. 7A). In the "bottom-up" approach, the vat was removed and replaced with a 35 mm diameter culture dish. The dish was placed at the center of the platform with an 18 mm$^2$ cover glass bonded to the bottom to allow the cured hydrogel to temporarily attach to it during processing. The pre-polymer solution was pipetted into the container one layer at a time beginning at the bottom (FIG. 7B). After each layer was photopolymerized by either method, the platform was lowered a specified distance, and a new layer was subsequently photopolymerized. The laser (325 nm) was used to selectively cross-link the pre-polymer solution at a precisely calculated energy dose.

The energy dose of the laser was varied to obtain a series of gels with different thicknesses. The thickness of each gel was measured by taking advantage of the transparent property of hydrogels and embedding fluorescent microbeads within each sample. 0.1% (w/v) fluorescent Nile Red microparticles (0.7-0.9 µm, Spherotech, Lake Forest, Ill., USA) were incorporated into the pre-polymer solution at a 1:1000 dilution. The solution was then pipetted into a custom-made container with a thin cover glass on top in contact with the solution. Samples were cured in the SLA by writing a cross-hatched pattern using a range of laser energy doses ($E_{avg}$). The energy doses were controlled by varying the laser beam writing speed in the SLA software. After polymerization, the cover glass was lifted off with the polymerized gel layer attached. The thickness of the cured gel ($C_d$) was then measured using an inverted fluorescent microscope (IX81, Olympus, Center Valley, Pa., USA) and IPLab software (BD Biosciences, Rockville, Md., USA). The measured thicknesses were plotted on a semilogarithmic graph as a function of energy dose. Using the working curve equation, $$C_d = D_p \ln\left(\frac{E_{avg}}{E_c}\right)$$

where $D_p$ is the penetration depth and $E_c$ is the critical exposure energy, $D_p$ and $E_c$ were calculated with linear regression analysis software (OriginPro 8.1, OriginLab, Northampton, Mass., USA) to determine the energy dose ($E_{avg}$) required to cure a layer of desired thickness ($C_d$) of the hydrogel. If the layer was not cured deeply enough, it would not attach to the layer below it, resulting in delamination. If the layer was cured too greatly, it would distort and reduce part accuracy.

The working curves for 20% (w/v) PEGDA with $M_w$ 700, 3,400, and 5,000 Da are shown in FIG. 8A. The measurements fit the linear regression model extremely well. The average standard deviation of all the layer thickness measurements was ±11.9 µm. The $D_p$ and $E_c$ values, shown in Table 1, indicated a decreasing $D_p$ and $E_c$ trend with increasing $M_w$. To test the accuracy of these values, the values were inputted into the SLA software along with user-specified $C_d$ to make a new series of gels. As an example, the measured thicknesses for $M_w$ 700 Da were comparable to their specified thicknesses (FIG. 8B), showing very little deviation. Complex 3D structures prepared from these PEGDA hydrogels were successfully fabricated with the "bottom-up" approach following the characterization process (FIGS. 8C and 8D).

TABLE 1

Calculated $D_p$, $E_c$, and average pore size of PEGDA hydrogels as a function of $M_w$.

| PEG $M_w$ (Da) | $D_p$ | $E_c$ | Pore Size |
|---|---|---|---|
| 700 | 0.346 | 40.89 | 3.105 |
| 3,400 | 0.258 | 11.10 | 8.280 |
| 5,000 | 0.231 | 7.17 | 10.973 |
| 10,000 | | | 20.340 |

For all multi-layer experiments utilizing the bottom-up approach, a second characterization step was performed to determine the amount of volume required to cure a layer of specified thickness. To achieve an average thickness (100 µm, for example), the volume was calibrated precisely for each layer due to surface tension between the walls of the container and the pre-polymer solution. 1×2 mm blocks were built in the SLA with embedded fluorescent microbeads. Each block had up to 20 layers. The thickness of each layer was measured by tipping the block on its side and visualizing in fluorescence microscopy. ImageJ analysis software was used to determine the thickness. The volume was then adjusted until the average of all layers reached the desired average thickness, such as 100 µm.

Figure 9:
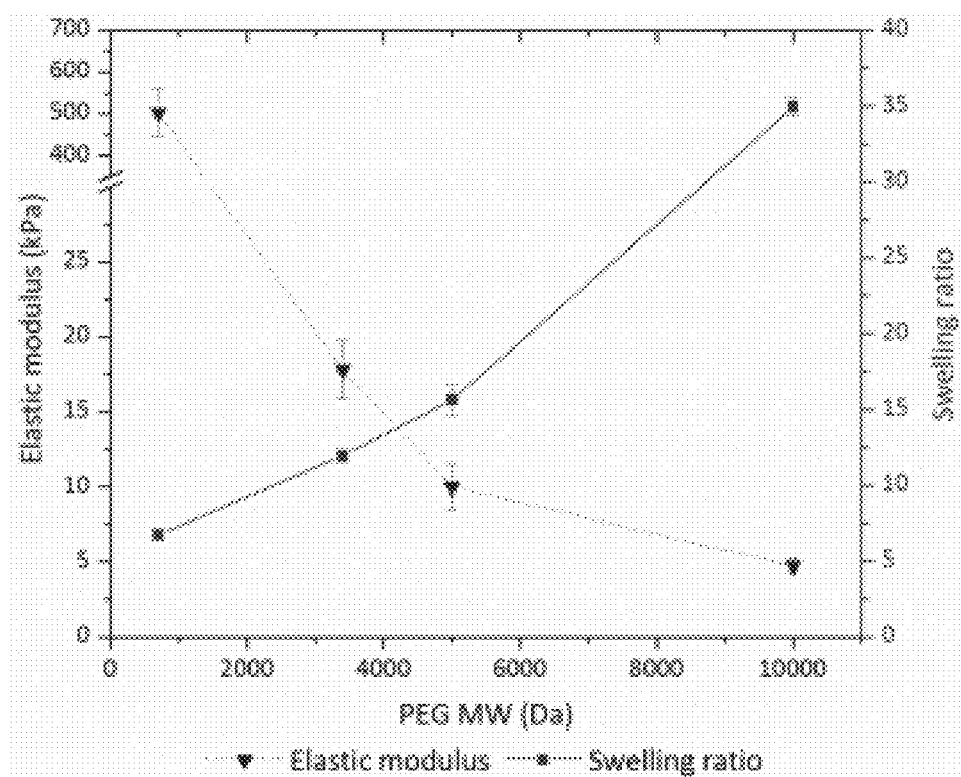
FIG. 9 shows the elastic moduli and swelling ratios for PEGDA hydrogels. The elastic moduli (E, left axis) and swelling ratios (Q, right axis) were measured and calculated for 20% PEGDA hydrogels as a function of $M_w$ (700, 3,400, 5,000, and 10,000 Da). All experiments used 0.5% photoinitiator concentration.
Figure 10A:
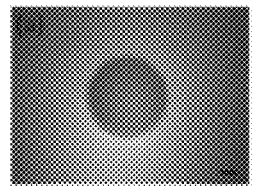
FIG. 10 shows that the diameters of hydrogel disks fabricated with 20% PEGDA $M_w$ 700 Da (A), 3,400 Da (B), 5,000 Da (C), and 10,000 Da (D) to be a specified size increase as a function of increasing $M_w$. 20% PEGDA hydrogels with the desired $M_w$ were used to make disks with a diameter of 5 mm in the SLA. The gel disks were incubated in culture medium for 24 hours at 37° C. before imaging in the stereomicroscope. Scale bars are 1 mm.
Figure 10B:
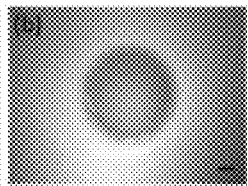
Figure 10C:
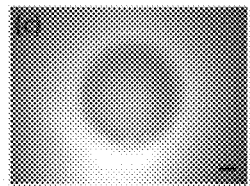
Figure 10D:
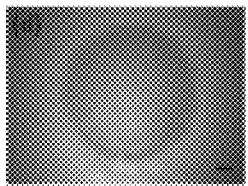

The degree of swelling and the mechanical properties of laser-polymerized PEGDA hydrogels were also investigated as a function of $M_w$. The laser power of the SLA was approximately 15 mW, and the average energy dose used to photopolymerize the gel disks was 1600 mJ cm$^{-2}$. The swelling ratios (Q) and elastic moduli (E) for 20% (w/v) PEGDA hydrogels with $M_w$ 700, 3,400, 5,000, and 10,000 Da were measured and calculated from these gel disks (FIG. 9). Gel disks were subjected to compression using a mechanical testing system (Insight, MTS Systems, Eden Prairie, Minn., USA). The elastic modulus (E) of the gel was measured by compressing at a constant deformation rate of 1.0 mm/s at 25° C. From the strain limit to the first 10%, the elastic modulus was calculated using the slope of the stress (σ) versus strain (λ) curve. Assuming that the gels followed an affined network model, the shear modulus (S) was calculated from the slope of the $\sigma_{vs.}-(\lambda-\lambda-2)$ curve, where λ is the ratio of the deformed length to the undeformed length of the hydrogel (Raeber et al., 2005, Biophys. J. 89:1374-88; Chu et al., 2009, Polymer 50:5288-92). The swelling ratios of the gels at equilibrium were determined by measuring the weight of the swollen gels after 24 h in pH 7.4 buffer solutions at 37° C. and the weight of the dried gels. The degree of swelling (Q), defined as the reciprocal of the volume fraction of a polymer in a hydrogel ($v_2$), was calculated from the following equation, $$Q = v_2^{-1} = \rho_P\left(\frac{Q_m}{\rho_S} + \frac{1}{\rho_P}\right)$$

where $\rho_S$ was the density of water, $\rho_P$ was the density of polymer, and $Q_m$ was the swelling ratio, the mass ratio of swelled gel to dried gel.

As expected, the Q increased and the E decreased with increasing PEGDA $M_w$ (FIG. 9). The elastic moduli obtained ranged from 4.73±0.46 kPa for $M_w$ 10,000 Da to 503±57 kPa for $M_w$ 700 Da, which covers an array of native tissues having similar moduli (Nguyen et al., 1992, Proc. 1st Eur. Conf. Rapid Prototyping, 133-61). Stereomicroscopic images of PEG hydrogels after 24 h incubation in cell culture medium showed an increase in swelling capacity with increasing $M_w$ (FIG. 10).

The swelling ratios were also used to calculate the average pore size of the gel disks as a function of $M_w$ (Table 1). The average pore size (ξ) was calculated from the polymer volume fraction ($v_{2,s}$) and the unperturbed mean-square end-to-end distance of the monomer unit ($r_0^{-2}$) using the following equations:

$$\xi = (v_{2,s}^{-1/3})(r_o^{-2})^{1/2}$$

$$(r_o^{-2}) = l\left(2\frac{\overline{M_c}}{\overline{M_r}}\right)^{1/2} C^{1/2} = l(2n)^{1/2}C^{1/2}$$

where l is the average value of the bond length between C—C and C—O bonds in the repeatable unit of PEG [—O—CH$_2$—CH$_2$—], which is taken as 1.46 Å; $M_c$ is the average molecular mass between cross-links in the network; $M_r$ is the molecular mass of the PEG repeating unit (44 g mol$^{-1}$); C is the characteristic ratio for PEG, which was taken here as 4.

Example 2: Cell Encapsulation by "Top-Down" and "Bottom-Up" Fabrication

Figure 11A:
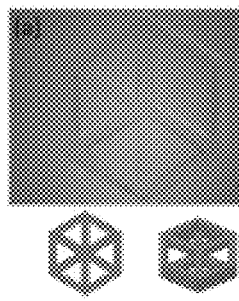
FIG. 11A-D encapsulation of NIH/3T3 cells in hydrogels. (A) Fabrication of a 2 mm thick complex 3D structure composed of 20 layers (with CAD images). Two approaches were used to encapsulate $10 \times 10^6$ cells/mL: (B) top-down and (C) bottoms-up SLA modifications. Cells were immediately stained with MTT (over 4 hours) for visualization. In the top-down approach, cells settled to the bottom of the container and did not encapsulate well. In the bottoms-up approach, cells and pre-polymer were added before polymerization of each layer, which led to homogeneous and high cell densities. (D) Intensity measurements of an MTT stain quantitatively showed homogeneity throughout the structure immediately after encapsulation. Scale bars are 1 mm.
Figure 11B:
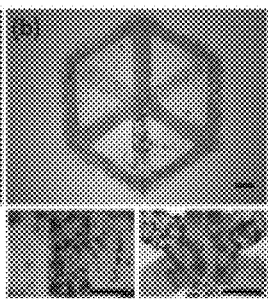

Cell encapsulation was initially accomplished by using the "top-down" fabrication process, which held all the pre-polymer solution in a stationary container. A 2 mm thick complex 3D structure, which was composed of 20 layers (100 µm per layer), was fabricated using this approach (FIG. 11A). The distribution of cells embedded within these structures was examined using MTT stain and stereomicroscopy (FIG. 11B). The purple formazan crystals produced by the viable cells appeared to have an inhomogeneous distribution with more cells being embedded at the bottom of the structure than at the top of it. This was caused by cells that settled toward the bottom of the container due to gravity.

Figure 11C:
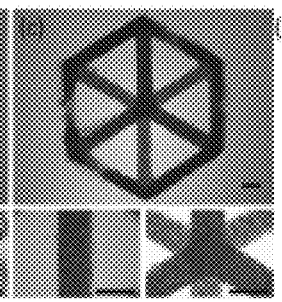
Figure 11D:
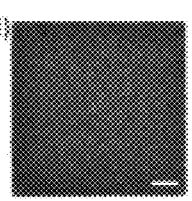

To prevent this, the "top-down" approach was altered, and the same complex 3D structure was fabricated using the "bottom-up" fabrication process. In this approach, the pre-polymer solution containing cells was pipetted into the container one layer at a time. The cells did not have time to settle to the bottom before the layer was cured. As a result, a uniform distribution of cells was achieved throughout the hydrogel, which was evident by the homogeneous distribution of purple formazan crystals (FIG. 11C). To quantitatively evaluate this, an intensity profile at different regions of the hydrogel was examined and confirmed to be uniform (FIG. 11D).

Example 3: Determination of Cell Viability in 3D Hydrogels

Two methods were used to evaluate long-term cell viability in the SLA: (1) encapsulation in single-layer 3D hydrogels (1 total layer, 1 mm thick per layer), and (2) encapsulation in multi-layer 3D hydrogels (10 total layers, 100 µm thick per layer). Cell viability was quantitatively measured using MTS (3-(4,5-dimethylthiazol-2-yl)-5-(3-carboxymethoxyphenyl)-2-(4-sulfophenyl)-2H-tetrazolium, Promega, Madison, Wis., USA), a tetrazolium compound which, in the presence of phenazine methosulfate (PMS, Sigma Aldrich, St Louis, Mo., USA), is reduced by living cells to yield a water-soluble formazan product. MTS (333 μg mL$^{-1}$) and PMS (25 μM) were added to the cell-laden hydrogels in DMEM without phenol red in an incubator at 37° C. and 5% $CO_2$. After incubating for 4 h, 20% SDS (Fisher Scientific, Springfield, N.J., USA) in sterilized $H_2O^{dd}$ was added to stop the reaction. The hydrogels were incubated at 37° C. for 15 h to allow diffusion of formazan into the medium. The absorbance was measured at 490 nm using a Synergy HT microplate reader (BioTek, Winooski, Vt., USA). Viability was qualitatively evaluated in stereo-microscopy using an MTT assay (3-(4,5-dimethylthiazol-2-yl)-2,5-diphenyltetrazolium bromide, Sigma Aldrich, St Louis, Mo., USA) by incubating the cell-laden hydrogels in a 10% solution of DMEM without phenol red at 37° C. and 5% $CO_2$ for 4 h. Fluorescence microscopy using calcein AM and ethidium homodimer stains was also used for qualitative evaluation (Molecular Probes, Eugene, Oreg., USA).

Figure 12:
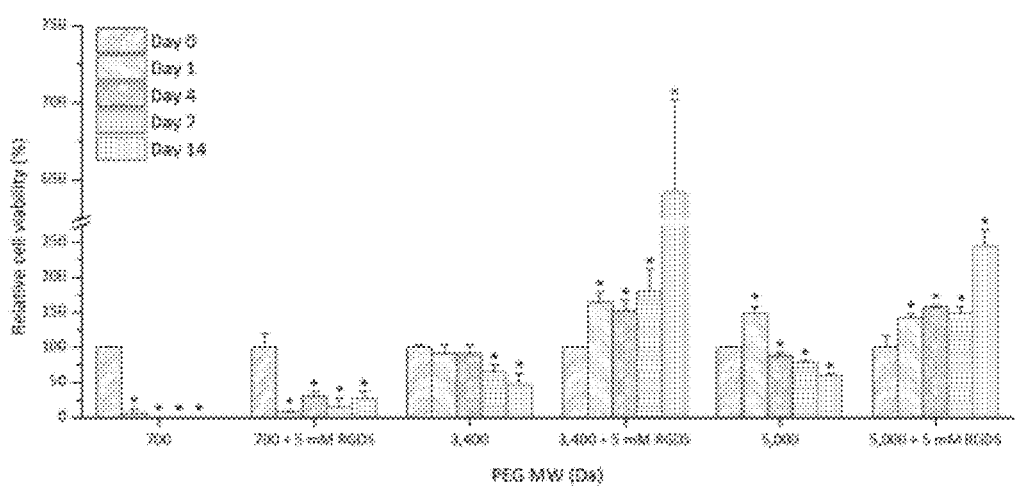
FIG. 12 shows viability of NIH/3T3 cells encapsulated in single-layer hydrogels of varying PEGDA $M_w$ and without or without RGDS peptides over 14 days in single-layer approach. The $M_w$ of PEGDA hydrogels were varied using 700, 3,400, and 5,000± RGDS groups. OD (490 nm) values quantified by MTS assays were normalized to 0 day. All values are mean±standard deviation of n=3. (*) denotes statistical difference compared to 0 day of same $M_w$.

In the first study, NIH/3T3 cells at a density of $2.0 \times 10^6$ cells/mL were encapsulated in 20% PEGDA hydrogels patterned in single-layer disks with dimensions of 1 mm thickness and 5 mm diameter. These disks were cultured over a period of 14 days. To achieve 1 mm thickness, the average energy dose of the laser during polymerization was 1,000 mJ/cm. The optical density (OD) measurements obtained from MTS assays on day 1, 4, 7, and 14 were converted to relative cell viability (%) by normalizing to 0 day (FIG. 12).

Figure 13:
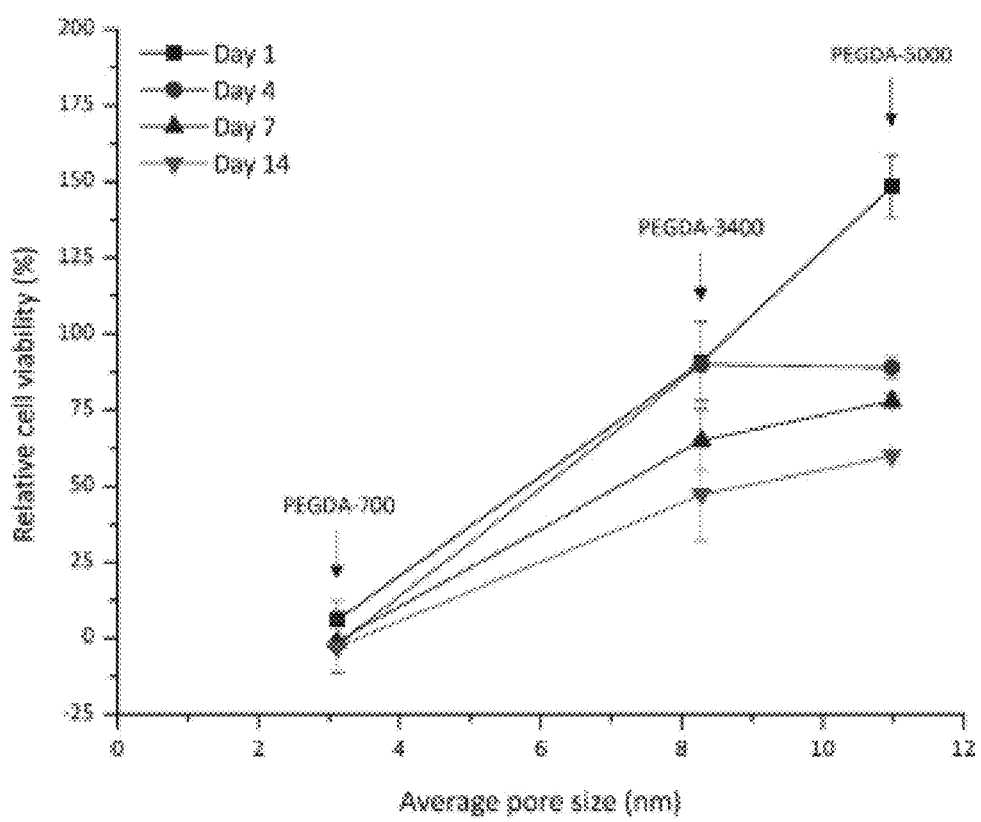
FIG. 13 shows that cell viability increases with increasing average hydrogel pore size. It is well-known that larger pore sizes increase the diffusion of oxygen, nutrients, and waste into and out of the cell-embedded gels. Larger pore sizes also remove the photoinitiator compounds and its free radical by-products out of the gel quicker, thereby increasing initial cell viability. Additionally, cell spreading and protein synthesis/secretion is improved in higher chain length gels, even in the absence of adhesion peptides.
Figure 15A:
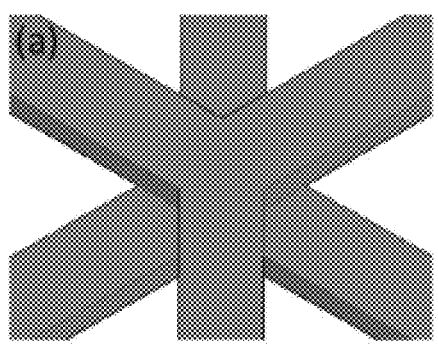
FIG. 15A shows a CAD rendering of a cross-hatch pattern used for layer-by-layer patterning. Each layer set was 1 mm thick (10 total layers, 100 μm each).
Figure 15B:
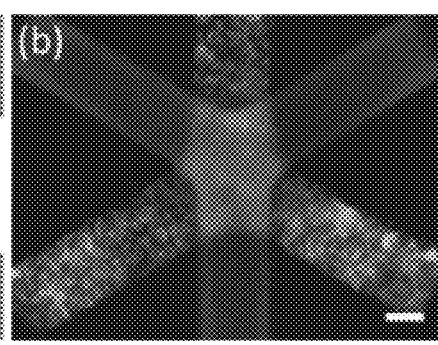
FIGS. 15B and 15C show fluorescent images of NIH/3T3 cells encapsulated in different layers stained with either CellTracker™ CMFDA dye or CMTMR dye.
Figure 15D:
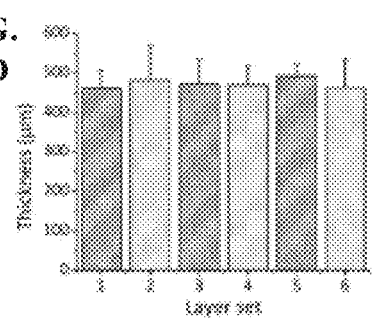
FIG. 15D shows that the thicknesses of layers stained with CMFDA (layers 2, 4, 6) were relatively equal to those stained with CMTMR (layers 1, 3, 5). Scale bars are 1 mm.
Figure 15C:
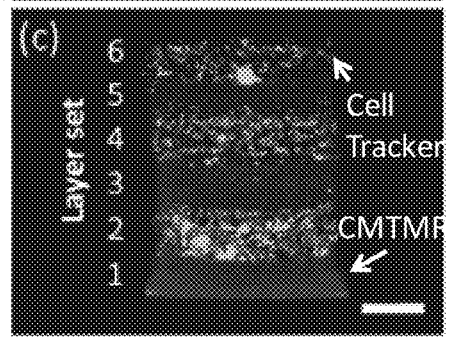

Cells encapsulated in PEGDA hydrogels with $M_w$ 700 Da survived the initial processing conditions of the SLA but died within 24 h of culturing. The result was observed with or without 5 mM RGDS (Arg-Gly-Asp-Ser, Sigma Aldrich, St Louis, Mo., USA) functionalization. Poor viability in PEGDA with $M_w$ 700 Da was most likely due to low degrees of swelling caused by small pore sizes. This restricted the diffusion of oxygen and nutrients into the inner core of the hydrogels. By increasing the $M_w$ to 3,400 Da, cells survived both the processing and culturing conditions. Viability remained statistically constant through 4 days. Subsequently, there was a decrease in viability to 65.10±9.81% after 7 days and to 47.46±15.39% after 14 days. Adhesive RGDS peptide sequences at 5 mM concentration were chemically linked to PEGDA hydrogels with $M_w$ 3,400 Da to test for any improvement in cell viability and proliferation. This resulted in a 1.6-fold increase in cell numbers after 24 h, which was maintained over 7 days. The effect of an even greater $M_w$ on cell viability was also evaluated. Cells encapsulated in PEGDA hydrogels with $M_w$ 5,000 Da followed the same trend as that of $M_w$ 3,400 Da. Except for an unsustained rise in metabolic activity after 24 h, the cell viability was relatively steady through 7 days, followed by a decrease in viability to 60.00±0.2% viability after 14 days. This was an improvement over the 14 day viability of PEGDA hydrogels with $M_w$ 3,400 Da (47.46±15.39%). When 5 mM RGDS was chemically linked to PEGDA hydrogels with $M_w$ 5,000 Da, there was a 1.4-fold increase in cell numbers after 24 h, which was maintained over 7 days. A significant increase in viability was seen after 14 days for $M_w$ 3,400 and 5,000 Da with RGDS peptide sequences due to high cell spreading, proliferation, and network formation on the exterior of the gels. Cell viability was also related to average pore size in FIG. 13. The relative cell viability and proliferation generally increased with increasing average pore size.

Since cell viability in single-layer disks may not be truly representative of viability in complex 3D structures, the second study evaluated cells encapsulated in multi-layer 3D hydrogels over 14 days. RGDS peptide sequences at 5 mM concentration were chemically linked to PEGDA with $M_w$ 5,000 Da. As shown in FIG. 14A, the cell numbers were increased 1.7-fold after 24 h, which was maintained through 7 days. By the end of 14 days, 46.44±19.56% of the cells were viable. Distribution of cells in single-layer and multi-layer PEGDA $M_w$ 5,000 Da hydrogels can be seen from stereomicroscopic images of hydrogels subjected to MTT staining (FIGS. 14B and 14C). Although there was a decrease in cell numbers after 14 days compared to 7 days, the distribution of the cells was homogeneous at both time points.

Qualitative LIVE/DEAD cell viability stain was performed during the same time points as the MTS assays. There was an increase in the dead cells over later time points, which supported the results of the more quantitative MTS assays. Nevertheless, in all cases except PEGDA $M_w$ 700 Da, the number of live cells was significantly more abundant than the number of dead ones.

Example 4: Cell Spreading and Attachment in Multi-Layer Hydrogels

NIH/3T3 cells encapsulated within multi-layer PEGDA hydrogels with $M_w$ 5,000 Da were examined for cell spreading and attachment. Spreading, which involves the active processes of actin polymerization and myosin contraction (Marklein & Burdick, 2010, *Soft Matter* 6:136-43) is a sign of cell viability and function. In order to visualize spreading, cell-laden hydrogels were examined every day by bright-field microscopy. After 14 days, cells were fixed using 4% formaldehyde solution (Fisher Scientific, Springfield, N.J., USA) overnight at room temperature. After washing several times in PBS, the gels were incubated in Triton X-100 (Sigma Aldrich, St Louis, Mo., USA) for 20 min and stained with rhodamine phalloidin (Molecular Probes, Eugene, Oreg., USA) and 4',6-diamindino-2-phenylindole (DAPI, Sigma Aldrich, St Louis, Mo., USA) for 30 min at 37° C. The cells were imaged using an inverted fluorescent microscope (IX81, Olympus, Center Valley, Pa., USA).

Viable cells did not spread in hydrogels without adhesive RGDS peptide sequences. Cells in multi-layer PEGDA hydrogels with RGDS-linked groups (5 mM) were examined in bright-field microscopy and fluorescence microscopy after rhodamine phalloidin (cytoskeleton) and DAPI (nuclei) staining. Cell spreading was clearly seen within hours of incubation and continued through 14 days. Some of these cells formed 3D connections with other cells in different layers, suggesting network formation.

Incorporation of multiple cell types within hydrogels in a spatially predetermined manner was demonstrated by using NIH/3T3 cells. These cells were separated into two suspensions: one labeled with CellTracker® CMFDA fluorescent dye, and the other labeled with CellTracker® CMTMR fluorescent dye. FIG. 15 illustrates top- and side-view images of a complex 3D structure with overhangs comprising two differently labeled cell suspensions. The thickness of each set of layers was uniform and showed minimal mixing. Quantitative results confirmed the distribution of these cells in uniformly distinct layers.

Example 5: Cantilever Fabrication and Characterization

Figure 16A:
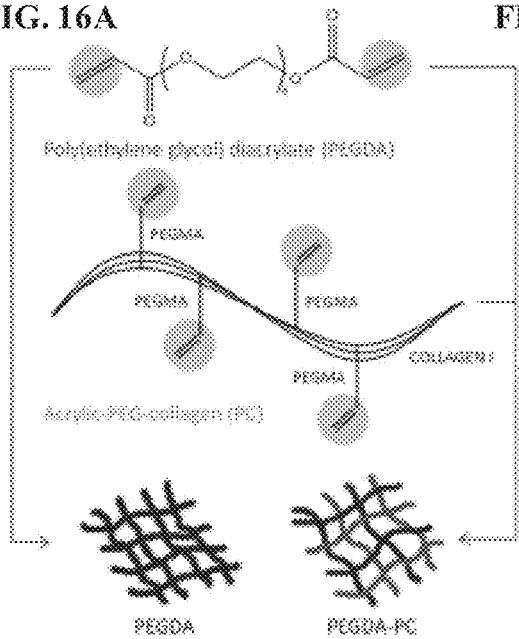
FIG. 16A-C shows biohybrid materials. (A) A mixture consisting of poly(ethylene glycol) diacrylate (PEGDA) and acrylic-PEG-collagen (PC) was formulated as photopolymerizable material for fabricating cantilever beams. Collagen I, extracted from rat tail, was modified on their lysine groups with acrylic groups to UV cross-link to the PEG backbone in the presence of a photoinitiator. (B and C) The mechanical properties of PEGDA-PC hydrogels were measured using a compression test at increasing molecular weight, demonstrating that the cantilever beams can be tuned to a wide range of elastic moduli and swelling ratios. These values did not change from that of PEGDA-only hydrogels, which suggests that the incorporation of acrylic collagen did not affect bulk mechanical properties. For n=3 and SD.
Figure 16B:
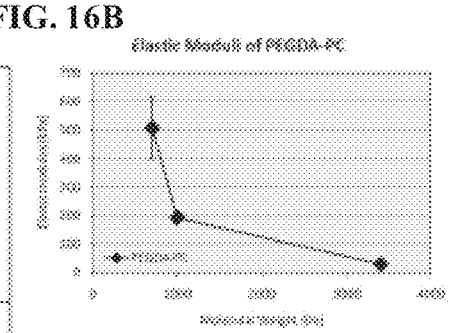
Figure 16C:
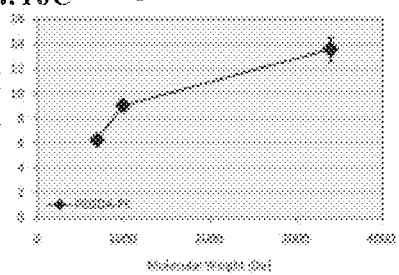

Acrylic-PEG-collagen was incorporated into photopolymerizable PEGDA hydrogels (PEGDA-PC) to create cantilevers with different stiffnesses in the SLA that can be used to measure contractile forces. Collagen was chemically linked to the PEGDA backbone by acrylating its lysines, making them photocross-linkable. Because PEGDA is normally inert, the collagen served to promote cell adhesion to the cantilever beams. Acrylic-PEG-collagen was prepared by mixing a working solution of acrylic-PEG-NHS (50 mg/mL in ice cold HBSS) with collagen I (3.68 mg/mL, rat tail; BD Biosciences) at a 1:1 acryl-to-lysine molar ratio for 30 min at 4° C. A 50% (v/v) acrylic-PEG-collagen solution was mixed with 20% poly(ethylene glycol) diacrylate (PEGDA) and 0.5% Irgacure 2959 photoinitiator in ice cold HBSS to form the pre-polymer solution (FIG. 16). PEGDA of $M_w$ 700 Da was used to fabricate the base of the cantilevers, and PEGDA of $M_w$ 700 Da (Sigma-Aldrich) or 3,400 Da (Laysan Bio) PEGDA was used to fabricate the beam of the cantilevers. A working solution of Irgacure 2959 photoinitiator (Ciba, Basel, Switzerland), which was only partially water-soluble, was prepared at 50% (w/v) by dissolution in DMSO.

Energy dose characterizations of the pre-polymer solutions were performed as described in Example 1. The pre-polymer solutions were pipetted into small containers capped on top by thin cover glasses. The SLA laser was used to draw circles that were 1 cm in diameter through the cover glass. The energy dose was varied by changing the scan speeds of the laser, which produced cylindrical gels of different thicknesses attached to the cover glasses. The thicknesses of these gels were measured, and a working curve was plotted to determine the penetration depth ($D_p$) and critical exposure energy ($E_c$) of the pre-polymer solution necessary to produce cantilever beams with precise thicknesses. The addition of collagen to the PEGDA backbone did not noticeably affect the mechanical properties of the hydrogel. Both the elastic modulus and swelling ratio were conserved for PEGDA-PC 700 and 3,400 (FIG. 16, Table 2). However, it was also observed that a change in the energy dose affected the elastic modulus of the gels. As a result, a constant energy dose (150 mJ/cm) was used to polymerize both the PEGDA-PC 700 and 3,400 cantilever beams so that only the $M_w$ of the hydrogels would affect the elastic modulus. From a biological perspective, mechanical properties of these hydrogels were closer to the in vivo environment of cells than either silicon or PDMS. They are also optically transparent, and therefore force measurements and immunofluorescence imaging of specific biological markers can be made simultaneously under light microscopes (Rajagopalan & Saif et al., 2011, *J. Micromech. Microeng.* 21: 1-11; Addae-Mensah & Wikswo, 2008, *Exp. Biol. Med.* 233:792-809).

TABLE 2

Mechanical properties of PEGDA-PC hydrogels.

| Hydrogel | Elastic Modulus | Swelling Ratio |
| --- | --- | --- |
| 20% PEGDA-PC 700 | 507 ± 110 kPa | 6.25 ± 0.06 |
| 20% PEGDA-PC 3,400 | 29.8 ± 17 kPa | 13.6 ± 0.95 |

Eight cantilevers were built for every fabrication run, with two sharing a common base. The fabrication setup (FIG. 17A) consisted of a 35 mm diameter Petri dish and an 18×18 mm cover glass that was bonded to the dish with double-sided tape. The dish was positioned at the center of the SLA platform, and a precisely-determined volume of pre-polymer solution was added into it. The beam of the cantilever was fabricated first by selective laser cross-linking of the pre-polymer solution to ensure that the precise thickness was not affected by the energy dose. The un-polymerized solution was then evacuated using a pipette and an equal volume of the pre-polymer solution for the cantilever base was added. The SLA then polymerized the first layer of the base (300 μm thick) according to the characterized energy dose for PEGDA-PC 700. The pre-polymer solution was added, and the elevator controlled by the SLA was lowered to a specified distance. After photopolymerization, the part was recoated, and the process was repeated until completion.

Figure 18A:
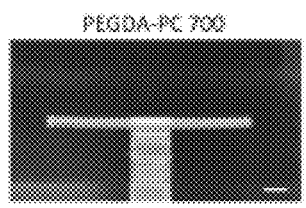
FIG. 18A-C shows intrinsic stress calculations. After the fabrication process, (A) PEGDA-PC 700 and (B) PEGDA-PC 3400 cantilevers were washed in HBSS to remove uncrosslinked pre-polymer solution. Due to an intrinsic stress, PEGDA-PC 3400 cantilevers would bend upward to relieve stress in the beams. (C) The peak stress was calculated by using finite element analysis to simulate the deflection of the cantilever beam (Inset). Scale bars are 1 mm. Statistics by one-way ANOVA, Tukey's test, *p<0.05 for n=8 and SD.
Figure 18B:
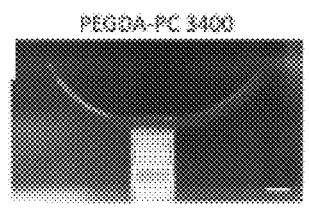

Example 6: Determination of Cantilever Beam Intrinsic Stress and Bending Due to Non-Uniform Stress Gradient Following fabrication, the cantilevers were transferred to a 0.02 N acetic acid solution to be washed to prevent the high collagen concentration in the unpolymerized pre-polymer solution from gelling around the cantilever. Washing was done for less than 1 min, as acetic acid affected cardiomyocyte adhesion on the polymerized collagen from the cantilever beams. The cantilevers were moved to a physiological pH buffer solution to swell overnight. The original dimensions (length×width×thickness) for the cantilevers were specified in CAD-based software, with the bases being 2×2×4 mm and the cantilever beams being 2×4×0.45 mm (FIG. 17B). To account for swelling, the cantilever thickness had to be adjusted. The actual dimensions of PEGDA-PC 700 and 3,400 cantilevers after 24 h of equilibrium swelling were 4.1×2.1×0.45 mm and 4.3×2.3×0.45 mm, respectively. The resulting PEGDA-PC 700 (FIG. 18A) and PEGDA-PC 3,400 (FIG. 18B) cantilevers had comparable dimensions after equilibrium swelling in HBSS.

Figure 19A:
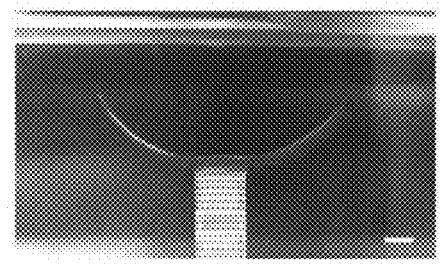
FIG. 19 A-B shows intrinsic stress changes as the cantilever thickness varies. The thickness for PEGDA-PC 3400 cantilevers was decreased from (A) 450 μm to (B) 300 μm. Consequently, the beam curved upward sharply, decreasing its radius of curvature and increasing its intrinsic stress. This implied that stiffness has a role in determining the intrinsic stress of the beam.
Figure 19B:
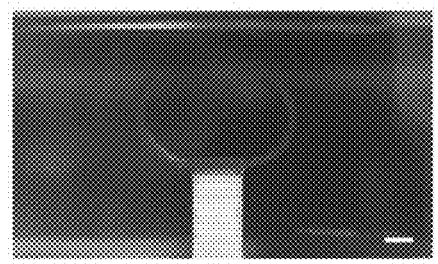

The cantilever beams were initially bent downward due to the weight of the unpolymerized pre-polymer solution and would begin to swell as water diffused into them. Over time, the cantilevers reached an equilibrium swelling state and bending resolved to a final angle. These angles were measured using ImageJ analysis software and converted to displacement values. As the average molecular weight of the PEG-based cantilevers increased, the bending angle increased upward in the clockwise direction. Similarly, the bending angle of the cantilevers increased as the thickness of the cantilever decreased (FIG. 19). PEGDA-PC 3,400 had a bending angle of 67.1±7.9° (3,420±560 μm deflection), whereas PEGDA-PC 700 did not bend (0° angle and 0 μm deflection). Thus, stiffness had a role in determining the intrinsic stress of the beam.

Figure 18C:
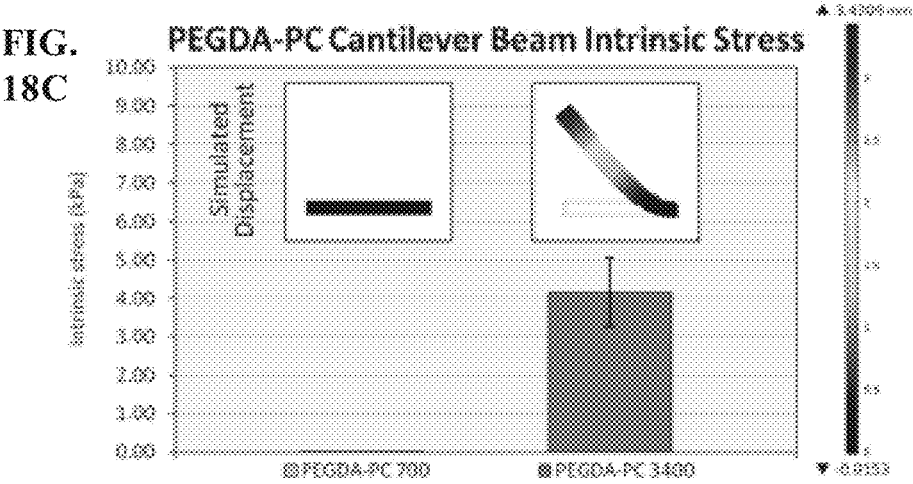

Finite element analysis (COMSOL simulations) was used with the displacement values to calculate the intrinsic stress of the cantilever beams (FIG. 18C). The intrinsic stress calculations were validated using the following equation (Sentura, 2000, *Microsystem Design* Springer, New York):

$$\sigma_{beam} = \frac{2E_b \delta t_b}{L^2}$$

where $\sigma_{beam}$ is the intrinsic stress (Pa), $E_b$ is the elastic modulus of the beam, δ is the deflection of the beam (m), $t_b$ is the thickness of the beam (m), and L is the length of the beam (m). The insets in FIG. 18C show the simulated displacement values, which were used to calculate the intrinsic stress for PEGDA-PC 700 and 3,400. The intrinsic stresses obtained were 0±0 Pa and 4160±910 Pa, respectively.

Cantilever bending due to non-uniform residual stress could be linked to differences in energy of the laser throughout the pre-polymer solution during polymerization. As the laser penetrated into the solution, it was absorbed by the photoinitiator and monomers. By the time it reached a penetration depth of 450 µm at the other end of the beam, the energy was decreased, which reduces the overall cross-linking density. The Beer-Lambert law was used to calculate the absorbance of the SLA laser ($\Delta$=325 nm) through the pre-polymer solution:

$$A = \varepsilon l c$$

where A is the absorbance, $\varepsilon$ is the molar extinction coefficient (L mol$^{-1}$ cm$^{-1}$), l is the path length (cm), and c is the concentration of the solution (mol/L). The molar extinction coefficient, $\varepsilon$, at the laser wavelength of 325 nm was obtained experimentally for the photoinitiator, Irgacure 2959: 676.7 L mol$^{-1}$ cm$^{-1}$, which was similar to results in the literature (Fairbanks et al., 2009, *Biomaterials* 30:6702-7).

Next, the absorbance at the bottom of the pre-polymer solution (the back face of the cantilever hydrogel) was calculated through the pre-polymer solution using $\varepsilon$=676.7 L mol$^{-1}$ cm$^{-1}$, l=450 µm (cantilever thickness), and c=0.0223 mol/L (Irgacure 2959 concentration). The resulting absorbance, A, was 0.679 was converted to percent transmittance, % T, and measured to be 20.9% using the following equation:

$$A = 2 - \log 10\% \, T$$

Since there was 100% transmittance at the surface of the pre-polymer solution (the incident face of the cantilever hydrogel), there was a difference of 79.1%, due to the absorbance of the laser by the photoinitiator. Therefore, there was a significant difference in the UV exposure dose at the incident face and back face of the cantilever hydrogel, indicating that a gradient in the swelling due to water absorption and stiffness contributed to cantilever bending due to non-uniform residual stress.

Example 7: Adhesion and Spreading of Cardiomyocytes on Cantilevers

To fabricate cantilevers to measure contractile force of cardiomyocytes, cardiomyocytes were first obtained from 2 day old neonatal Sprague-Dawley rats (Harlan Laboratories) using an approved protocol by the Institutional Animal Care and Use Committee (IACUC; Protocol #08190). Briefly, whole hearts were excised from the rats as described in the literature and placed in an ice-cold HBSS buffer (Maass & Buvoli, 2007, *Methods Mol. Biol.*, 366:321-30). Using small scissors, the left and right atria were removed and the remaining ventricles were minced into 1 mm$^3$ pieces. The minced ventricles were digested in 0.1% (w/v) purified trypsin (Worthington Biochemicals) while gently rocking at 4° C. overnight. After 18 h, warm growth medium was added for 5 min at 37° C. to inhibit trypsin digestion. The supernatant was discarded, and 0.1% (w/v) purified type II collagenase (Worthington Biochemicals) was added for 45 min while gently rocking at 37° C. The digested tissue was triturated to mechanically loosen the cells, and the suspension was filtered through a 75 µm cell strainer to remove undigested connective tissue. The suspension was removed after centrifugation at 150×g for 5 min. The remaining cell pellet was re-suspended in warm growth medium and pre-plated for 1 h to enrich the suspension for cardiomyocytes. Cardiomyocytes extracted from neonatal rat ventricular myocytes were seeded onto PEGDA, PEGDA-RGD, and PEGDA-collagen (PEGDA-PC) cantilevers. RGD sequences, which are found in numerous extracellular matrix proteins, were used in an attempt to improve cardiomyocyte function by chemically attaching collagen molecules to PEGDA hydrogels. This chemistry was performed by the reaction of lysine amines on collagen to acrylate-PEG-NHS. The acrylate-PEG-collagen was then combined in solution with PEGDA to form a PEG-based hydrogel linked with bioactive collagen for cell adhesion.

As a result of the intrinsic stress, the curvature of the cantilevers made it difficult to seed cells uniformly and at high densities on the beams. Thus, the cantilevers were inverted and placed in a 24-well plate, and the residual liquid was removed. This created a surface tension that mechanically flattened the curved cantilever beams onto the bottom of the plate. Neonatal rat ventricular myocytes were seeded on the flattened cantilever beams with 2 million cells per well (1×10$^6$ cells/cm). This backside seeding also prevented the cell sheets on the two cantilevers from linking together so that they could be examined as two independent measurements. The cantilevers with seeded cells were centrifuged to distribute cells evenly on the cantilevers. After 12 h, the cantilevers were transferred to a new dish with fresh medium and cultured overnight.

48 h after seeding, cells were qualitatively evaluated for cell adhesion and spreading. Cardiomyocytes spread substantially better on PEGDA-PC hydrogels than PEGDA and PEGDA-RGD. The cells on PEGDA and PEGDA-RGD appeared to remain balled up in spheres and preferentially attached to each other rather than on the substrate. Many of the cells had washed off after a change of media indicating poor cell attachment. Conversely, cardiomyocytes on PEGDA-PC spread greatly, formed gap junctions, and began to contract in synchrony. Consequently, PEGDA-PC hydrogels were preferentially used for cantilever fabrication.

Example 8: Determination of Cantilever Bending Due to Cell Traction Forces 24 h post-seeding, the cantilevers had already begun to bend downward due to cell traction forces as the cardiomyocytes began to spread and reorganize themselves. Cell traction forces are generated by actomyosin interactions and actin polymerization and regulated by intracellular proteins such as α-smooth muscle actin and soluble factors such as TGF-β. Once transmitted to the extracellular matrix through stress fibers via focal adhesions, which are assemblies of ECM proteins, transmembrane receptors, and cytoplasmic structural and signaling proteins, cell traction forces direct many cellular functions, including cell migration, ECM organization, and mechanical signal generation.

Figure 20:
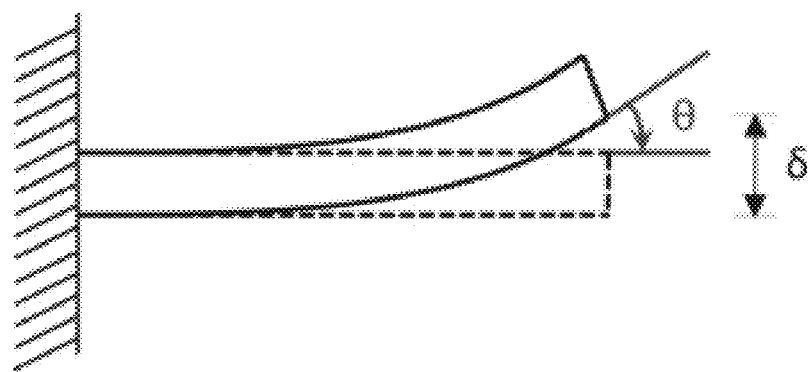
FIG. 20 is a schematic for measuring bending angles and deflection values of a cantilever. For bending angles, θ, a line was fitted along the slope of the free end of the deformed cantilever. A second line was drawn along the horizontal axis of the undeformed cantilever, which created a protractor for measuring the angle. For deflection values, δ, the vertical distance of the cantilever from the undeformed base to its deformed base was also measured to determine the deflection value.

Vertical motion and bending angles of the cantilevers were captured using a camcorder (HandyCam, Sony USA, New York, N.Y. USA) with an advanced HAD CCD imager at 720×480 pixel video capture resolution. The camcorder recorded at 60 fps with a 60× optical zoom. It was fixed on a multi-axis stage (Thorlabs) and placed in a temperature- and CO$_2$-controlled culture chamber due to cardiomyocyte sensitivity to changes in the outside environment. The temperature and CO$_2$ were set to 37° C. and 5%, respectively. The bending angles, $\theta$, and deflection values, $\delta$, were measured using the Measure Tool in Adobe Photoshop software (FIG. 20). Still images were taken by the camcorder, and a line was fitted along the slope of the free end of the deformed cantilever. A second line was drawn along the horizontal axis of the undeformed cantilever, which created a protractor for measuring the angle. The vertical distance of the cantilever from the undeformed base to its deformed base was also measured to determine the deflection value. The smallest resolution that could be measured with this software platform was 0.1°.

The stress induced by the cell sheet was clearly seen by the change in displacement over time on the cantilever beams (FIG. 21A). The cell sheet continued to apply traction forces on the cantilevers over 72 h before it stabilized. The bending angle of the curved beams was measured and recorded every day for 4 days (FIG. 21B). Because of the cell traction forces, the bending angle for PEGDA-PC 3,400 cantilevers was decreased from its intrinsic value of 67.1±7.9° to 44.2±6.0° by the third day of culture. PEGDA-PC 700 cantilevers, having a high elastic modulus, did not bend at all during culture.

The displacement values were also measured and used in FEM simulations to calculate the stress on the cantilever beams by the cell sheet. Cells seeded on the cantilevers formed sheets that were considered thin films, and the cantilevers were modeled as composite, two-component systems. The model was validated by simulating cantilevers with beam dimensions and comparing the stress calculations to Atkinson's approximation, a variant of Stoney's equation (Engler et al., 2008, *J. Cell Sci.*, 121:3794-802):

$$\sigma_{film} \approx \frac{\delta E_b t_b^3}{4 t_f (1 - v_b)(t_f + t_b) L}$$

where $\sigma_{film}$ is the cell sheet stress (Pa), $t_f$ is the thickness of the cell sheet (m), and $v_b$ is Poisson's ratio of the beam. The simulations were performed with measured elastic moduli of 503 kPa for PEGDA-PC 700 and 17.82 kPa for PEGDA-PC 3,400. Poisson's ratio of PEGDA-PC was assumed to be 0.499. Based on the literature, the elastic modulus of a sheet of cardiomyocytes was assumed to be 10 kPa with a thickness of 10 μm (Shi et al., 2011, *Phys. Chem. Chem. Phys.* 13:7540-5; Berry et al., 2006, *Am. J. Physiol.*, H2196-203.) The density of cardiomyocytes and the PEGDA-PC material was assumed to be 1.06 kg m$^{-3}$ and 1.12 kg m$^{-3}$, respectively.

The simulated displacements and stresses for PEGDA-PC 700 and 3,400 are shown in FIG. 21C. For PEGDA-PC 3,400, the highest level of stress was seen at the fixed end of the beam. The maximum stress values were calculated every day (FIG. 21D), and the change in stress was plotted every 24 h. The cell sheet reached a maximum stress of 2,040 Pa before it leveled off. The change in stress was highest after the first day and continually decreased before there was virtually no change between 72 and 96 h.

Example 9: Characterization of Actuation and Beating Frequency of Cardiomyocytes on PEGDA-PC Cantilevers Although cardiomyocytes began to contract individually as early as 24 h after seeding, the cells did not beat synchronously as a whole sheet until at least 48 h. During this period, cardiomyocytes formed electrical connections between each other through gap junctions. Membrane proteins known as connexins formed six-membered rings (connexons) on the sarcolemma of cardiomyocytes. When gap junctions are open, they provide direct communication between the sarcoplasmic spaces of adjoining cells, creating a functional synctium or network of synchronized cells (Severs et al., 2008, *Cardiovasc. Res.* 80:9-19; Noorman et al., 2009, *J. Mol. Cell. Cardiol.* 47:23-31). After 76 h, when the majority of these connections were formed, cells were stained for sarcomeric α-actinin to qualitatively elucidate the morphology of cardiomyocytes on PEGDA-PC 700 and 3,400 cantilevers. In both cases, cardiomyocytes exhibited the expression of sarcomeric α-actinin, an actin-binding protein that plays a key role in the formation and maintenance of Z-lines, throughout the cytoskeleton. The localization of sarcomeric α-actinin in both PEGDA-PC 700 and 3,400 demonstrated a typical periodicity in the Z-lines of cardiomyocytes.

Cardiomyocyte cell sheets on PEGDA-PC 3,400 cantilevers had all started to actuate after 48 h, whereas only a quarter of the cardiomyocyte cell sheets on PEGDA-PC 700 cantilevers started to actuate during the same time period (Table 3). This percentage increased after 72 h, but the development of functional synctium was substantially slower. Furthermore, the beating frequency of the cardiomyocyte cell sheet was greater for PEGDA-PC 3,400 than for PEGDA-PC 700 (Table 3). These results seem to be in agreement with previous reports that claim that the substrate elasticity of the developing myocardial microenvironment are optimal for transmitting contractile work to the matrix and for promoting actomyosin striations (Discher et al., 2005, *Science* 310:1139-43). In addition to the substrate elasticity, it is possible the hydrogels with higher molecular weight have more cell adhesive sites exposed on the surface of the cantilever than hydrogels with lower molecular weight.

TABLE 3

Actuation and beating frequency of cardiomyocytes on PEGDA-PC 700 and 3,400 substrates.

|  | Actuation (48 h) (%) | Beating Frequency (48 h) (Hz) | Actuation (72 h) (%) | Beating Frequency (72 h) (Hz) | Actuation Amplitude (72 h) (μm) | Stiffness Values (N/m) | Total Forces (μN) |
|---|---|---|---|---|---|---|---|
| PEGDA-PC 700 | 25 | 0.39 ± 0.05 | 100 | 0.44 ± 0.06 | 2 ± 8 | 0.36 | 0.89 ± 2.89 |
| PEGDA-PC 3,400 | 83 | 1.12 ± 0.14 | 100 | 1.40 ± 0.16 | 390 ± 40 | 0.013 | 5.09 ± 0.48 |

The actuation amplitudes of the cantilevers were also measured over 96 h. Similar to the beating frequency, the amplitudes reached a maximum on the third day post-seeding (Table 3). The actuation amplitudes did not reach a maximum suddenly; rather, they increased linearly over time as more cardiomyocytes joined the synctium of cells. Using these amplitudes, the contractile forces of cardiomyocyte cell sheets on PEGDA-PC 700 and 3,400 cantilevers were calculated using the following equations:

$$F = k_c \delta$$

$$k_c = \frac{w}{4(E_f t_f + E_b t_b)L^3}(E_f^2 t_f^4 + E_b^2 t_b^4 + 4E_b t_b E_f t_f^3 + 6E_b t_b^2 E_f t_f^2 + 4E_b t_b^3 E_f t_f)$$

where F is the contractile force, $k_c$ is the stiffness of the cantilever, w is the width of the beam, and $E_f$ is the elastic modulus of the film. Stiffness, $k_c$, was derived for a composite, two-component system (Table 3) (Shih et al., 2001, *J. Appl. Phys.* 89:1497-505). Using these values, and the peak deflection of actuated cantilevers (from its relaxation state to its contraction state), total forces for PEGDA-PC and PEGDA-PC 3,400 are shown in Table 3.

Example 10: Patterning Acryl-Fibronectin Hydrogels

Figure 22:
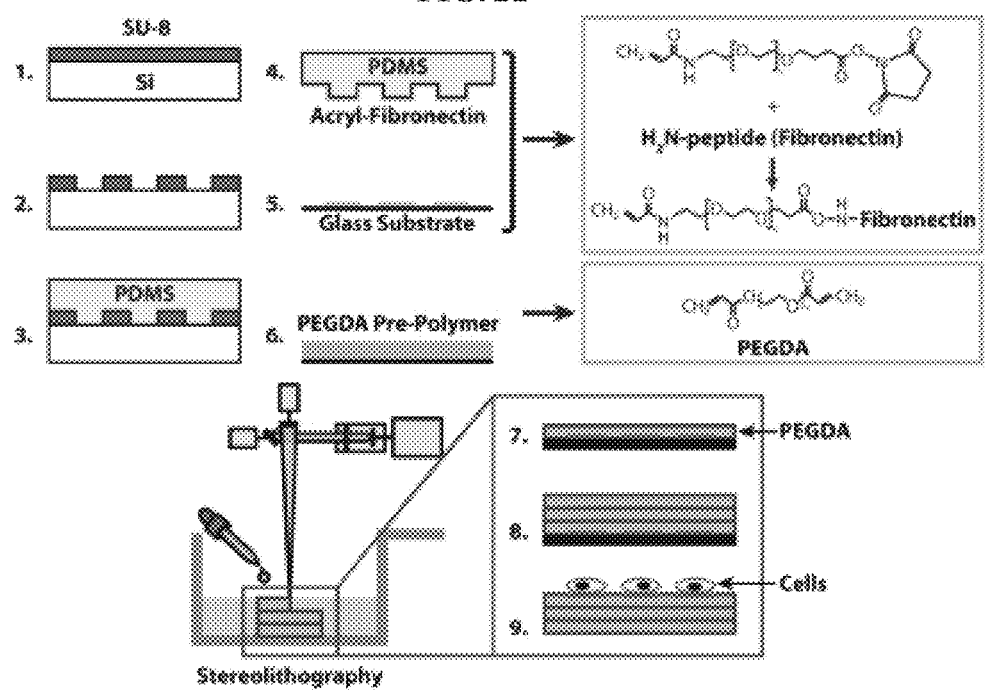
FIG. 22 shows patterning acryl-fibronectin hydrogels. (1) Silicon wafers were coated with 5 μm of SU-8 photoresist. (2) Line patterns were formed after exposure of photoresist and silicon with UV light through a chrome mask. (3) PDMS was poured over the silicon master and polymerized by baking. A negative of the pattern from the silicon master was imprinted on the surface of the PDMS making a stamp. (4) An ink solution containing acryl-fibronectin was pipetted onto the PDMS stamp. Acrylic fibronectin was made by mixing acryl-PEG-NHS and fibronectin in PBS and allowing the PEGDA cross-linker to attach to free lysine groups in fibronectin. (5) After stamps were incubated with ink, line patterns were transferred to glass slides by stamping. (6) Pre-polymer solution of PEGDA ($M_w$ 3,400) and a photo-activator is poured into a dish over patterned glass slides. (7) The dish containing pre-polymer and patterned glass is put into the stereolithography apparatus (SLA) and polymerized to form a hydrogel. (8) 3D structures were built layer-by-layer adding additional pre-polymer before crosslinking. (9) Hydrogels were inverted and seeded with cells. During building of the first layer, acryl-fibronectin was transferred to the surface of the hydrogel allowing for cell attachment.

The method for patterning hydrogels is shown in FIG. 22. To create patterns of proteins on 3D hydrogel constructs, polydimethylsiloxane (PDMS) stamps were first prepared. Master molds for the PDMS stamps were fabricated on a silicon wafer with SU-8 negative photoresist following a standard procedure (Chen et al., 1998, *Biotechnol. Prog.* 14: 356-363; Kane et al., 1999, *Biomaterials*, 20:2363-76). The master molds contained patterns of 10, 50, and 100 µm wide lines with equal spacing. The height of each pattern was 5 µm. The patterned master molds were silanized with (tridecafluoro-1,1,2,2-tetrahydrooctyl)-1-trichlorosilane in vacuum for 1 h. PDMS (Dow Corning Sylgard 184 Silicone Elastomer Kit) was weighed out at a 10:1 ratio of polymer-to-curing agent (heat activated). The materials were thoroughly mixed for 3 min to ensure even distribution of the curing agent and poured onto the patterned master molds. Samples were placed in a desiccator, pulled under vacuum, and baked at 80° C. overnight. A negative of the pattern from the silicon master was imprinted on the surface of the PDMS, making a stamp.

Fibronectin from bovine plasma solution (Sigma Aldrich, St. Louis, Mo., USA) was diluted in PBS to a concentration of 50 µg/mL. For acryl-fibronectin ink, monoacrylated poly (ethylene glycol)-N-hydroxysuccinimide (acryl-PEG-NHS, $M_w$ 3,500 Da, JenKem Technology, Allen, Tex., USA) was dissolved in PBS at a concentration of 30 mg/mL. A working solution of acryl-fibronectin ink was prepared by mixing acryl-PEG-NHS with fibronectin at a 2:1 molar ratio of acrylate-to-lysine. The reaction was allowed to proceed for 30 min at 4° C. Fibronectin and acryl-fibronectin ink (50 µg/mL) were pipetted onto PDMS stamps for 1 h at 37° C. After incubation, excess ink was aspirated and dried under a stream of $N_2$. Stamps were placed pattern-side down onto 18 mm² glass coverslips. Pressure was applied for 30 s to allow adsorption of ink to the glass, and the coverslips were incubated for 45 min. Stamps were removed, and the coverslips were used within 1 h.

A pre-polymer solution of PEGDA ($M_w$ 3,400 Da) and photoinitiator was poured into a dish over patterned glass slides. A hydrogel was fabricated through polymerization by SLA, and 3D structures were built layer-by-layer adding additional pre-polymer solution before cross-linking. The hydrogels were rinsed in PBS and allowed to swell overnight before cell seeding.

Transfer of acryl-fibronectin from glass coverslips to hydrogels was confirmed by quantitative analysis of immunofluorescence imaging. Monoclonal anti-fibronectin produced in mouse (Sigma-Aldrich, St. Louis, Mo. USA) was diluted at 1:300 in PBS and added to the samples overnight at 4° C. The solution was then aspirated and rinsed 3× with PBS. Alexa Fluor 488 goat anti-mouse IgG (Life Technologies, Grand Island, N.Y. USA) was diluted 1:1000 in PBS and added for 2 h at 37° C. After rinsing 3× with PBS, the samples were imaged with an inverted fluorescence microscope (IX81, Olympus, Center Valley, Pa. USA). ImageJ software was used to calculate pixel intensity values; a line profile was drawn across the fluorescent images and grey values were extracted at each point on the line. Comparison of hydrogels built on glass coverslips with fibronectin and acryl-fibronectin showed that acryl-fibronectin successfully transferred from the glass coverslip to PEGDA ($M_w$ 3,400 Da) hydrogels. The average pixel intensity of acryl-fibronectin on hydrogels was measured at 129±10.9, while fibronectin on hydrogels had an average pixel intensity of 2.6±0.5.

Patterned line widths of 10, 50, and 100 µm on glass coverslips and hydrogels were measured to verify pattern integrity after acryl-fibronectin transfer. The line profile tool was used to draw horizontal lines perpendicular to patterned lines on 40× images, and the measured line widths were recorded. Measured line widths after PDMS stamping on glass and after acryl-fibronectin transfer to the 3D hydrogel constructs are shown in Table 4. Fibronectin transfer did not occur without acrylate groups. Swelling after polymerization caused the measured line widths on the hydrogels to be greater than those on the glass coverslip. However, the average pixel intensity of fluorescently-labeled acryl-fibronectin patterns on hydrogels did not appear to decrease significantly to the extent that it would affect cell alignment.

TABLE 4

Actual widths of patterned lines on glass coverslips and hydrogels.

| Patterned Line Widths (µm) | Line Widths After PDMS Stamping on Glass Coverslips (µm) | Line Widths After Acryl-Fibronectin Transfer (µm) |
|---|---|---|
| 10 | 11.5 ± 0.4 | 13.4 ± 0.5 |
| 50 | 49.1 ± 1.8 | 57.3 ± 0.6 |
| 100 | 98.7 ± 0.6 | 110.5 ± 5.8 |

Figure 23A:
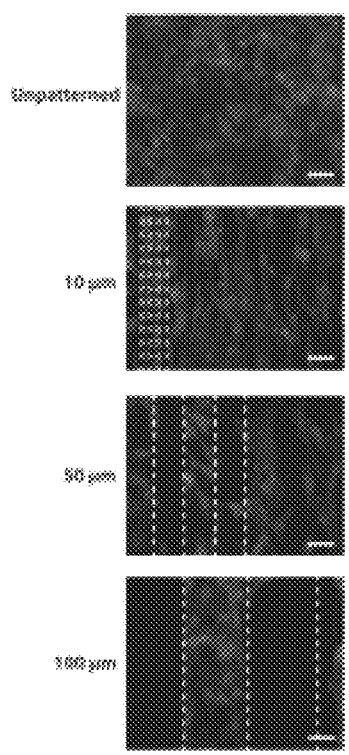
FIG. 23-A-C shows aligning fibroblasts on unpatterned and patterned hydrogels. (A) Fibroblasts with fluorescent nuclear (DAPI) and actin (rhodamine-phalloidin) stains were cultured on hydrogels with unpatterned and patterned acryl-fibronectin with lines 10, 50, and 100 μm wide. (B) Power spectrum generated by radially summating frequencies from fast Fourier (FFT) converted images. Peaks at 90° and 180° correspond to vertical alignment in images and can be seen for fibroblasts patterned on lines. (C) Analysis of fibroblasts at the cellular level shows a significant decrease in circularity for cells grown on 10 and 50 μm lines. A small but insignificant shift can be seen on 100 μm lines. A decrease in circularity can be attributed to a constriction of cellular growth area. Scale bars represent 50 μm wide.

Example 11: Characterization of Fibroblast Growth, Alignment, and Morphology on Hydrogels Hydrogels were positioned in 12-well plates with fibronectin and acryl-fibronectin patterns facing up. NIH/3T3 mouse embryonic fibroblasts were seeded at 90,000 cells/cm and cultured on 3D hydrogel constructs with acryl-fibronectin patterns of unpatterned, 10, 50, and 100 µm wide lines to demonstrate feasibility of cell alignment. The cells rapidly adhered to and began to spread on the line patterns after 1 h in culture. Within 24 h, the cells were activated to proliferate along the line patterns. FIG. 23A shows that the cells recognized the acryl-fibronectin patterns and aligned parallel to the lines. As the line spacing decreased from 100 to 10 µm, number of cells that bridged patterned lines increased. Regardless of cell bridging, the cells continued to align parallel to the lines.

To visualize the morphology of fibroblasts on hydrogel constructs, the cells were fixed and labeled at different time points. For fixation, samples were rinsed with PBS and incubated in 4% paraformaldehyde (PFA, Sigma-Aldrich, St. Louis, Mo. USA) for 30 minutes. After rinsing three times with PBS, a solution of 3,3'-dihexyloxacarbocyanine iodide (DiOC$_6$, Life Technologies) was added at 1:1000 dilution in PBS to stain for a cell's endoplasmic reticulum, vesicle membranes, and mitochondria. Samples were then permeabilized with 0.1% Triton X-100 (Sigma Aldrich) for 10 minutes and blocked with 2.5% bovine serum albumin (BSA) in PBS to prevent non-specific binding. Cell nuclei were stained with a 1:1,000 dilution of 2-(4-amidinophenyl)-1H-indole-6-carboxamidine (DAPI, Life Technologies), and actin was stained with a 1:1,000 dilution of rhodamine phalloidin (BD Biosciences). Fluorescent images were taken with the inverted fluorescence microscope. Fluorescent images showed that as the line patterns decreased from 100 to 10 µm, alignment of individual cells increased. At 100 µm line patterns, the cells were generally not spatially-confined, and they could spread in any direction that was not restricted by a neighboring cell.

Figure 23B:
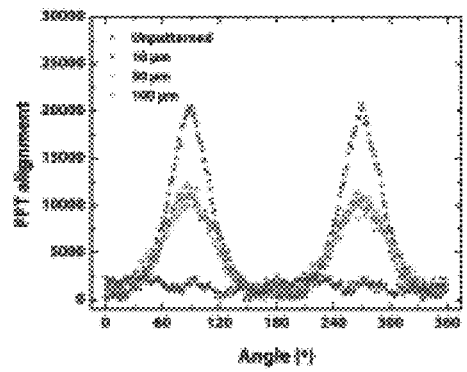

This result was confirmed quantitatively with fast Fourier transform analysis (FIG. 23B). ImageJ software was used to enhance image contrast, subtract the background, and filter noise from the image. Images were converted to the frequency domain by FFT transformation and rotated 90° to account for the inherent rotation that occurs during transformation. A circle was drawn over the FFT image, and the oval profile plugin was used to radially sum pixel intensities around the circle. A power spectrum was generated based on radially summated values, with 0° correlating to frequencies at the 3 o'clock position, 90° at the 12 o'clock position, 180° at the 9 o'clock position, and 270° at 6 o'clock position. Conversion of images to the frequency domain revealed directed fibroblast growth and linear pattern formation. Distinct peaks were seen in the power spectrum of fibroblasts grown on patterned lines of all widths at 0° and 180°. Fibroblasts grown on unpatterned hydrogels lacked these peaks and had more uniformly-scattered spectrums. Furthermore, as the line widths increased, the peaks also decreased, and the spectrums were more scattered.

Cell morphometrics were used to examine the individual shape of cells on patterned and unpatterned 3D hydrogel constructs. Post-image processing, a threshold was applied to make a binary image and individual cells were identified. Image J software object tools were used to measure and compare the cell circularity and nuclear orientation. Ten circularity bins of 0.1 intervals were set up, and circularity values between 0 and 1 were placed in each bin (0 being a line and 1 being a circle). Significance was verified with a Student's t-test statistical analysis. Nuclear orientation was measured by using the 'analyze particles' tool to fit an ellipse to threshold images of DAPI-stained nuclei and measuring the angle of the ellipse. Direction and length of cell elongation was determined by measuring the angle and distance from the nucleus to the furthest edge of the actin stained cell.

Figure 23C:
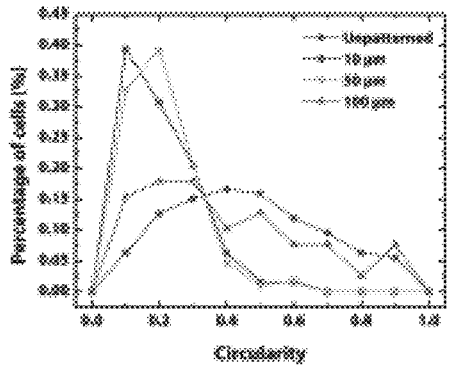

Growth of cells along the patterned lines altered their shape, making them more linear. FIG. 23C and Table 5 show the decreasing shift of cell circularity measurements between patterned and unpatterned cells. Average circularity was significantly different between unpatterned fibroblasts and fibroblasts restricted to growth on 10 µm and 50 µm lines (Table 5). Cell shape was altered on 100 µm lines but was not statistically significant. Fibroblast elongation, which was measured from the furthest edge of stained actin on each side of the cell to the nucleus, was parallel to line direction. Average angles for unpatterned and patterned fibroblasts were significantly different (Table 5). Clustering of cell elongation near 90° was observed for fibroblasts grown on 10 and 50 µm lines. Length of elongation caused by patterning showed a significantly greater difference. Nuclear alignment was measured by fitting an ellipse to images of cell nuclei labeled with DAPI and proved to be insignificant on patterned and unpatterned lines (Table 5). However, there was a trend observed of nuclei aligned parallel to patterns.

TABLE 5

Fibroblast morphology on patterned and unpatterned hydrogels.

| Hydrogel | Cell Circularity | p-value | Fibroblast Elongation (°) | p-value | Length of Elongation (µm) | p-value | Nuclear alignment (°) | p-value |
|---|---|---|---|---|---|---|---|---|
| 10 µm lines | 0.15 ± 0.10 | $1.97E^{-25}$ | 90.86 | $4.6E^{-2}$ | 78.8 | $9.16E^{-18}$ | 89.98 | 0.42 |
| 50 µm lines | 0.15 ± 0.11 | $4.83E^{-25}$ | 88.85 | $4.9E^{-3}$ | 54.9 | $6.78E^{-08}$ | 93.43 | 0.90 |
| 100 µm lines | | | 89.92 | $8.6E^{-4}$ | 40.6 | $2.05E^{-4}$ | 93.13 | 0.52 |
| Unpatterned | 0.41 ± 0.22 | | 95.35 | | 44.33 | | 79.97 | |

Example 12: Bio-Bot Fabrication

A "bio-bot" was fabricated to demonstrate the basic mechanical principles for simple locomotion (FIG. 1). Each bio-bot consisted of 'biological bimorph' cantilever structures and a base structure as its main components. The cantilevers were fabricated first; a pattern of the cantilevers was traced onto the surface of a thin layer of PEGDA ($M_w$ 3,400 Da) hydrogel precursor solution with an ultraviolet (UV, 325 nm) laser beam. The part was then recoated with a thin layer of PEGDA ($M_w$ 700 Da) hydrogel precursor solution, and the laser traced a pattern of the bases. This layer-by-layer process was repeated until the base structures were complete (FIG. 1B). The cantilever material was chosen to mimic the elasticity of the rat heart muscle (22-50 kPa), while the base material was chosen to be rigid (~500 kPa) and to retain its shape (Wang & Lin, 2007, *Biomechan. Model Mechanobiol.* 6:361-71). A top down image of an array of bio-bots with cantilevers (7×2 mm) attached to their corresponding bases (2×2 mm) is shown in FIG. 1C. Since PEG is relatively inert, it required surface modification with extracellular matrix proteins to enable subsequent cell attachment. Type I collagen was used to coat the surface of the cantilever through addition reactions of light-activated Sulfo-SANPAH. Each construct was transferred using a small spatula onto individual 12 mm circular glass coverslips (Fisher Scientific) with cantilevers down (as fabricated). Sufosuccinimidyl-6-(4'-azido-2'-nitrophenylamino)-hexanoate (Sulfo-SANPAH; Pierce Biotechnology) was prepared at 0.5 mg/mL in sterilized 50 mM HEPES, pH 8.5 immediately before use. Approximately 100 μL Sulfo-SANPAH solution was added to cover the bio-bot cantilever structures. The solution was exposed to a 302 nm ultraviolet lamp (UVP Blak-Ray) at a distance of 3 inches for 5 min. The solution was aspirated out and the bio-bots were rinsed with HEPES buffer. Collagen was prepared at a concentration of 0.10 mg/mL in 0.1 N acetic acid, added to cover the bio-bot cantilever structures, and incubated overnight at 37° C. The solution was then aspirated and the bio-bots were rinsed with sterilized water and PBS, pH 7.4.

Figure 1D:
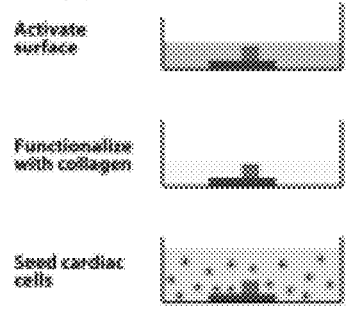

Cardiomyocytes derived from neonatal rat hearts were extracted as described in Example 7 and seeded onto the cantilevers at 1,800 cells/mm (FIG. 1D). The cell-laden bio-bots were incubated overnight at 37° C. and 5% $CO_2$ before changing the medium. The cardiomyocytes attached to the cantilevers, increased in size, and exhibited spontaneous contractile activity. Over several days, the cells became confluent and formed a cardiac cell sheet that contracted in synchrony.

Example 13: Optimization of Bio-Bot Symmetry and Shape for Locomotion

Symmetrical bio-bots (base positioned at the center of the cantilever (also referred to herein as a hydrogel strip) and asymmetrical bio-bots (base not positioned at the center of the cantilever) were fabricated. Actuation was a result of the contractile forces of a cardiac cell sheet to retract a cantilever structure (a power stroke). The symmetrical and asymmetrical bio-bots were tested to maximize the use of a power stroke for net forward movement. Side-view images and movies of the bio-bots were taken with a Sony Handycam DCR-SR68 camcorder at 30 frames per second (fps). The camcorder was fixed on a custom-made multi-axis stage (Thorlabs). Top-view images and movies of the bio-bots were taken with digital microscope cameras (Flex and RT3, SPOT) and software on either an inverted microscope (IX81, Olympus) or stereomicroscope (MZ FL III, Leica). Movies were recorded at approximately 11 fps. Net displacement of bio-bot forward motion was measured using the Measure Tool in Photoshop software (CS5.1, Adobe) by superimposing consecutive frames. Frames (3 ms) were extracted in Movie Maker (Windows) software. Contact area of the bio-bot legs to the substrate was also measured with side-view movies in Movie Maker and Photoshop, with the assumption that the contact was uniform into the frame.

While the symmetrical bio-bot actuated with each power stroke, it did not generate any net forward movement. Consequently, the base was re-positioned away from the center of the cantilever to establish an asymmetric structure. To accomplish this, the length of the cantilever was shortened on one side of the base. Cross-sectional images showing several iterations of the bio-bot were taken after rotating it onto its base (FIG. 1E). The bottom iteration was used as the final bio-bot design, as illustrated by a schematic image with attached cardiac cell sheet (FIG. 1F).

Next, the shape of the bio-bot, which was determined by the curvature of the cantilever, was optimized in order to regulate the friction between bio-bot "legs" and substrate, which is necessary to generate propulsive forces for locomotion. The residual surface stress generated during photopolymerization was employed to introduce a well-controlled curvature on the hydrogel cantilever following hydrogel swelling. The final curvature of the cantilever was a combined effect of the residual surface stress in the hydrogel fabrication process and a cell-induced surface stress originated from the cardiac cell sheet. By varying the thickness of the cantilever, the initial and final curvatures of the cantilever were controlled, as were the locomotive mechanism of the bio-bots. The thickness of the cantilever was regulated by adjusting the volume of PEGDA ($M_w$ 3,400 Da) hydrogel precursor solution that was added during fabrication (as described in Example 1).

Figure 24A:
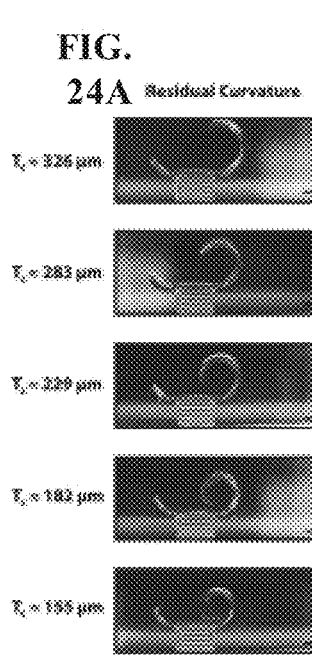
FIG. 24A-D shows design of bio-bots through residual and cell-induced surface stresses. (A) Representative cross-sectional images of bio-bots with varying cantilever thicknesses. After overnight swelling, the residual stresses cause the cantilevers to curl upward, depending on the thickness of the cantilever. (B) Representative cross-sectional images of bio-bots three days after cardiac cell seeding on the cantilever side facing the base. Cytoskeletal tension from the cells causes the cantilever to curl downward to a final bio-bot shape. (C) Plot of inverse radius of curvature vs. cantilever thickness for residual (pre-seeded) and residual+ cell-induced curvature (post-seeded). (D) Plot of surface stress vs. cantilever thickness for residual and residual+cell-induced curvature. All scale bars are 1 mm.
Figure 24B:
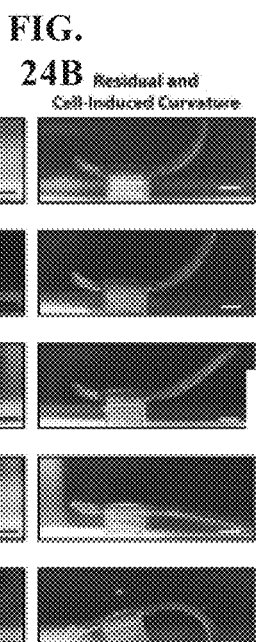

For quantitative analysis of the bending mechanism of the cantilever, bio-bots with five different cantilever thicknesses were fabricated and imaged before seeding the cardiomyocytes (FIG. 24A) and after formation of the cardiac cell sheet (FIG. 24B). The cantilevers before cell seeding were bent upward by the residual surface stress on the top side of the cantilever and the curvature of the cantilever increased with decreasing cantilever thickness. After the formation of the cardiac cell sheet, the cell-induced surface stress on the bottom side of the cantilever decreased the curvature of the cantilever or even bent the cantilever downward.

Figure 24C:
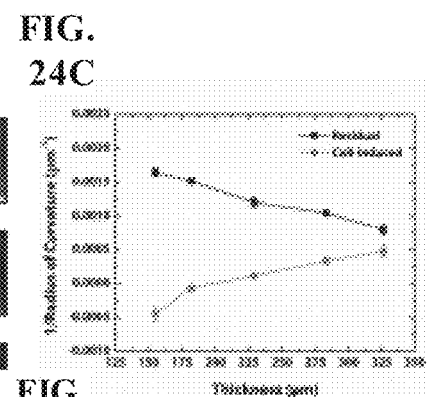

The radii of curvature (ROC) of the cantilevers were measured from the cross-sectional images and presented as the inverse of the measured ROC (FIG. 24C). To minimize manual error in measuring the radius of curvature (ROC), the average of the three ROCs obtained by three independent methods was used. First, the ThreePointCircularROI plugin in ImageJ software (NIH) was used, which automatically calculates the center of circle and the radius of curvature from the three manually-specified points on the cantilever image. Secondly, the arc angle of the bent cantilever, θ, was used to calculate ROC. The center of the circle calculated with previous method was used to measure the arc angle. Since the length of the cantilever, $L_c$ was fixed to be 4 mm, the ROC was obtained with the equation: $L_c=\theta*ROC$. Lastly, the fitting circle was manually superimposed on the cantilever images, and the radius of the circle was used.

Figure 24D:
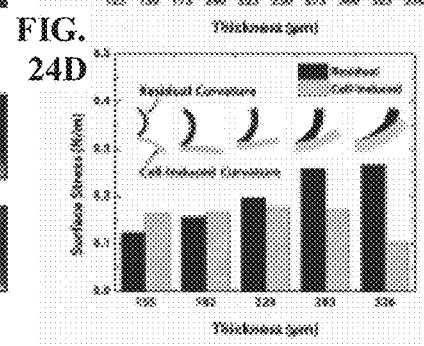
Figure 25A:
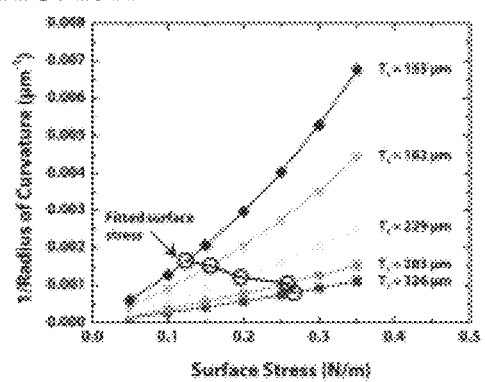
FIG. 25 A-B shows extraction of residual and cell-induced surface stresses. (A) Plot of inverse radius of curvature vs. surface stress for residual curvature (pre-seed). (B) Plot of inverse radius of curvature vs. surface stress for residual+cell-induced curvature (post-seed). The measured radius of curvature was used to interpolate residual and cell-induced surface stresses from these plots.
Figure 25B:
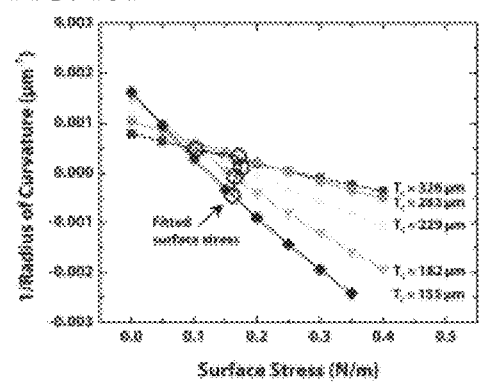

From the measured ROC of the cantilevers, the intrinsic residual surface stress and the cell-induced surface stress were extracted using finite element analysis (FIGS. 24D and 25). The radius of curvature (ROC) of the cantilever with varying surface stress (0~0.5 N/m) on its bottom side was simulated, and the residual surface stress was interpolated from the simulation results with the measured ROC from the experimental images. The cell-induced surface stress was obtained in similar manner. The ROC of the cantilever with the previously obtained residual surface stress on the bottom side and varying surface stress (0~0.5 N/m) on the top side was simulated, and the cell-induced stress was interpolated with the experimentally measured ROC. The intrinsic residual surface stress was 200±62 mN/m and decreased with decreasing cantilever thickness, and the cell-induced surface stress was found to be 155±30 mN/m.

Example 14: Determination of Locomotion Mechanisms of Bio-Bots

By varying the thickness and the curvature of the cantilever, three distinctive bio-bots were fabricated (Table 6), and their locomotion was analyzed.

TABLE 6

| Characterization of bio-bots analyzed for locomotion. | | |
|---|---|---|
| Bio-bot | Thickness (μm) | Orientation |
| 1 | 326 ± 17 | Upward facing base; actuating leg in contact with substrate |

TABLE 6-continued

Characterization of bio-bots analyzed for locomotion.

| Bio-bot | Thickness (μm) | Orientation |
|---|---|---|
| 2 | 182 ± 31 | Downward facing base; actuating leg in contact with substrate during power stroke; actuating leg not in contact with substrate when relaxed |
| 3 | 155 ± 9 | Downward facing base; actuating leg in contact with substrate at all times |

Spontaneous contraction of the cell sheet of the bio-bot caused the cantilever (actuating leg) to actuate and produce a power stroke. The power stroke of the actuating leg needed to exceed all opposing forces, which were dominant at these length scales, including drag force and friction in an aqueous medium, and friction between the actuating leg and substrate needed to be present. If the friction were too low, the actuating leg would slide; if the friction were too high, the bio-bot would be prevented from moving forward. Friction between the supporting leg and substrate also needed to balance the relaxation force of the actuating leg; otherwise, the bio-bot would slide back to its original position. Therefore, friction between the legs and substrate needed to be adjusted to maximize the power stroke for net forward movement.

Friction (F) is proportional to the actual area of contact (A):

$$F = \mu N = \mu N \quad \text{(A)}$$

where $\mu$ is the coefficient of friction and N is the normal force. The applied force needed to overcome static friction of a stationary bio-bot is greater than that to keep it sliding, or kinetic friction. The angle of repose method was used to determine the coefficients of static ($\mu_s$) and kinetic ($\mu_k$) friction by raising and lowering the incline plane until the bio-bot started and stopped sliding, respectively. The measured angles, $\theta_s=39.7°$ for static friction and $\theta_k=18.9°$ for kinetic friction, were used to calculate their coefficients of friction: $\mu_x = \tan \theta_x$, which were $\mu_s=0.83$ and $\mu_k=0.34$. Relative friction forces were generated for each of the legs against the substrate by multiplying the area of contact by the normalized ratio of $\mu_s/\mu_k$ depending on the motion state, as assessed through video capture using a digital camcorder at 30 frames per second (fps). FIG. 2 shows changes in friction forces of the actuating ($F_a$) and supporting ($F_s$) legs and friction force over time for a single power stroke for each of the bio-bots.

Net displacement of the bio-bots was observed and is summarized in Table 7. Table 7 also indicates the average velocity of the bio-bots as well as the average beating frequency of the cardiac cells of the bio-bots.

TABLE 7

Characterization of bio-bot locomotion mechanisms.

| Bio-bot | Power stroke length (ms) | Net displacement over 30 seconds (mm) | Average velocity over 30 seconds (μm/s) | Net displacement over 10 power strokes (μm) | Average beating frequencies of the cardiac cell sheets (Hz) |
|---|---|---|---|---|---|
| 1 | 39 | 0 | 0 | 0 | 1.14 |
| 2 | 27 | 7.15 | 236 | 337 | 1.50 |
| 3 | 30 | 1.95 | 71 | 182 | 0.39 |

Figure 2A:
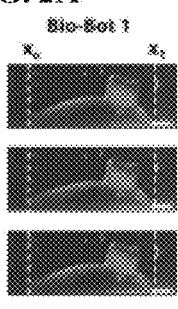
FIG. 2 shows (A) representative cross-sectional images of a bio-bot 1 power stroke, (B) a schematic diagram of a bio-bot 1 power stroke depicting no change between the friction forces of the actuating ($F_a$) and supporting legs ($F_s$), (C) a plot of friction force versus time for a single power stroke of bio-bot 1 showing the change between the coefficients of static friction ($\mu_s$, open fill) and kinetic friction ($\mu_k$, solid fill), (D) representative cross-sectional images of a bio-bot 2 power stroke, (E) a schematic diagram of bio-bot 2 power stroke, (F) a plot of friction force versus time for a single power stroke of bio-bot 2, (G) representative cross-sectional images of a bio-bot 3 power stroke, (H) a schematic diagram of bio-bot 3 power stroke, and (I) a plot of friction force versus time for a single power stroke of bio-bot 3.
Figure 2B:
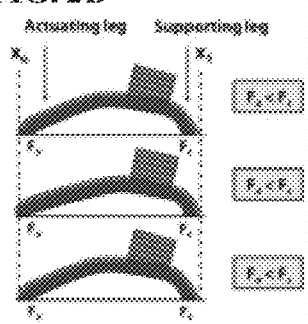
Figure 2C:
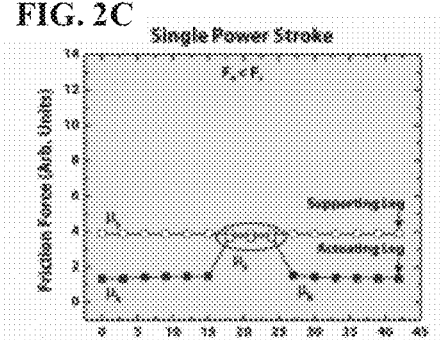

Generally, there was no net forward movement from bio-bot 1. The actuating leg slid back and forth between power strokes and subsequent relaxation periods (FIGS. 2A and B). This indicated that there was not enough friction between the actuating leg and substrate to generate enough propulsion force to overcome the friction between the supporting legs and substrate (FIG. 2C). Without displacement of the supporting leg, the actuating leg returned to its original position. As it relates to friction, similar surface areas of contact between both legs and the substrate seem to support this argument. Without a dominant power stroke, bio-bot 1 would not able to overcome the opposing friction of the supporting leg to produce net forward movement. However, there was the rare case that bio-bot 1 moved very slowly (27 μm/s).

Figure 2D:
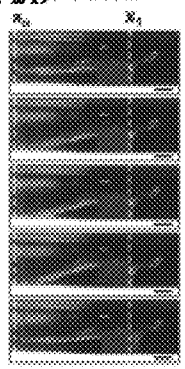
Figure 2E:
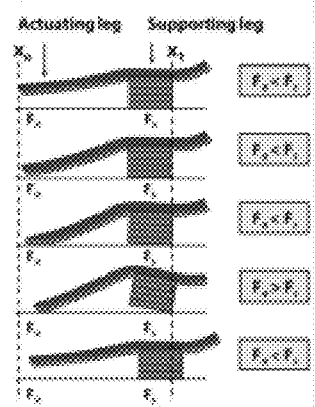
Figure 2F:
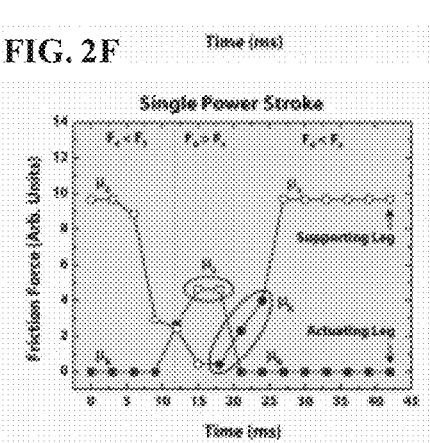

The mechanism of locomotion for bio-bot 2 was the most efficient and produced the largest net displacement. During the power stroke, the actuating leg bent against the substrate, which caused a conformational change in its shape (FIG. 2D, E). As a result, there was an increase in contact area of the actuating leg. The supporting leg tilted upward, causing a decrease in its area of contact. During relaxation, the bio-bot reverted back to its original conformation. Because the friction of the actuating leg was greater than the friction of the supporting leg, it resulted in net forward motion (FIG. 2F). After returning to its original conformation, the contact area (and thus, the friction) of the supporting leg increased, which prevented the bio-bot from moving backwards.

The mechanism of movement for bio-bot 3 worked similarly to bio-bot 2 but less efficiently. The actuating leg was already in contact with the substrate. During the power stroke, it retracted, causing a similar forward tilt of the supporting leg (FIG. 2G, H). However, the friction of the actuating leg was less and relatively constant. The supporting leg friction decreased as a result of the tilt, causing net forward movement during relaxation. However, during relaxation, the friction of the supporting leg was not high enough to withstand the momentum from relaxation of the actuating leg, which caused the bio-bot to slide back slightly. Therefore, the net displacement of bio-bot 3 was less than that of bio-bot 2 (FIG. 2I).

Example 15: Fabrication and Characterization of 3D Muscle Strip Bio-Bots

Figure 26A:
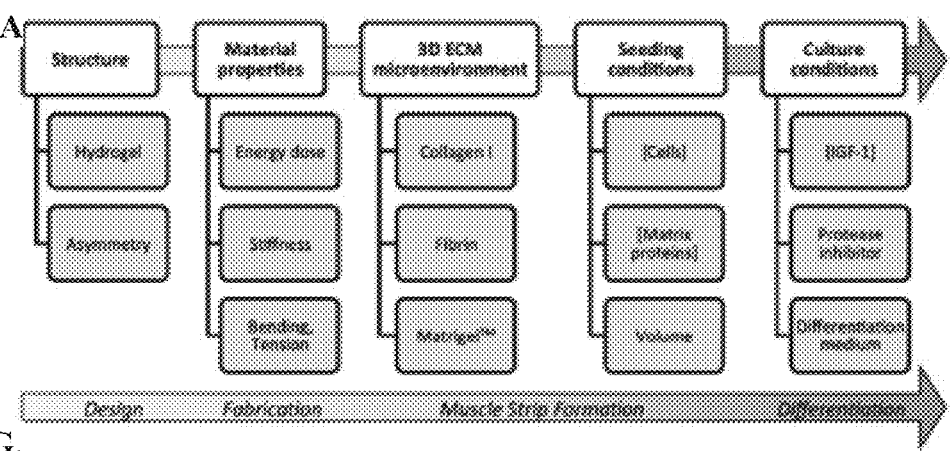
FIG. 26A is a schematic diagram of a design and optimization of 3D muscle powered bio-bots.
Figure 26B:
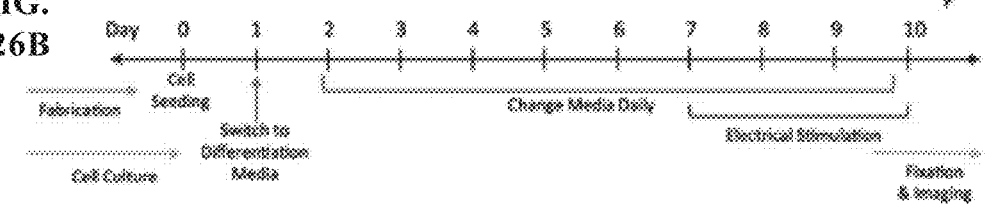
FIG. 26B is a representative timeline of the development of a functional 3D muscle strip bio-bot.

Modified cantilevers comprising a beam and two capped pillars (also referred to as posts or legs) were fabricated with PEGDA ($M_w$ 700 Da) (FIGS. 4 and 26). The PEGDA backbone was not chemically-linked with cell attachment proteins because the proteins were found to hinder compaction of the muscle strips. A linear elastic simulation was used to determine optimal beam and pillar dimensions that would combine high deflection with a robust mechanical structure. The deflection was simulated using finite-element simulations in response to a constant passive tension force of 992.7 μN (corresponding to a beam of modulus 319.4 kPa). Dimensions of the PEGDA hydrogel structures (FIG. 3B) evaluated are shown in Table 7. After fabrication, the structures were sterilized in 100% ethanol overnight and rinsed in PBS before interaction with cells and growth medium.

TABLE 7

Tested and optimal beam and pillar dimensions determined by linear elastic simulations.

| Dimension | Beam (Tested, mm) | Beam (Optimal, mm) | Pillar (Tested, mm) | Pillar (Optimal, mm) |
| --- | --- | --- | --- | --- |
| Length | 4.0-6.5 | 6.0 | | |
| Height | | | 0.8-1.4 | 1.2 |
| Width | 1.5-4.0 | 2.0 | 1.5-4.0 | 2.0 |
| Thickness | 0.5-0.75 | 0.55 | 0.75-2.0 | 1.0 |

C2C12 myoblasts were transfected with pAAV-Cag-Chr2-GFP-2A-Puro with Lipofectamine 2000 (Invitrogen, Carlsbad, Calif.) and grown under puromycin (2.5 µg/mL) selection for 2 weeks. Before cell seeding, bio-bots were positioned beam-down in polymerized holders in a 35-mm cell culture dish and aspirated of excess liquid. A liquid suspension of C2C12 skeletal muscle myoblasts and ECM proteins was added around the pillars of the bio-bot and polymerized via gelation of the matrix proteins. Embedded cells exerted traction forces on the fibrous proteins via integrin attachments to compact the matrix into a muscle strip over time, and the capped pillars acted as a physical anchor for the muscle strip to mimic the in vivo musculoskeletal arrangement in which force transmission occurs from a contracting muscle to bone through a connecting tendon. The ECM was a mixture of i) type I collagen or fibrin and ii) Matrigel™, a composition of laminin, entactin, and type IV collagen. Collagen and fibrin were chosen because naturally-derived hydrogels undergo macro-scale compaction when mixed with cells, leading to a substantially higher cell density and unidirectional cell alignment between the posts. For collagen strips, a cooled suspension of liquid type I collagen from rat tail (0.8, 1.4, or 2.0 mg/mL, BD Biosciences) was mixed with equal parts ice-cold growth medium and neutralized with 0.01 N NaOH. Pelleted cells ($1.0-10.0\times10^6$ cells/mL) were resuspended in ice-cold growth medium and mixed with Matrigel™ (30% v/v, BD Biosciences). Liquid neutralized type I collagen was mixed thoroughly with cells (C2C12 myoblasts (ATCC)) and Matrigel™, and the mixtures were added to each holder. For fibrin muscle strips, an ice-cold cell-matrix solution of Matrigel™ (30% of total cell-matrix volume), fibrinogen (4 mg/mL, Sigma-Aldrich), thrombin from bovine plasma (0.5 U/mg fibrinogen, Sigma-Aldrich), and C2C12s suspended in GM at a concentration of $5\times10^6$ cells/mL were added to each holder. The post/beam assemblies were then incubated at 37° C. to induce collagen/fibrin polymerization, and growth medium was added to each assembly upon gelation. Time-lapsed compaction was captured with a stereomicroscope (MZ FL III, Leica).

After 7 days, the myoblasts were induced to differentiate by switching to high-glucose DMEM supplemented with 10% horse serum (Lonza) and 50 ng/mL insulin-like growth factor-1 (IGF-1, Sigma). A protease inhibitor, aminocaproic acid (1 mg/mL, Sigma) was added to the growth and differentiation medium to prevent degradation of the extracellular matrix proteins by the cells. Differentiated, multinucleated myotubes were distributed throughout muscle strips supplemented with IGF-1. Muscle strips cultured without IGF-1 contained populations of both undifferentiated myoblasts as well as multinucleated myotubes at later time points, signaling that although IGF-1 increased the rate of fusion and maturation, its absence did not hinder muscle strip development. With the addition of 50 ng/mL IGF-1, the portion of the fibrin-based muscle strip occupied by cells more than doubled. Average myotube density did not change significantly after day 7.

Hematoxylin and eosin (H&E) staining of histological sections of IGF-1 supplemented fibrin muscle strips revealed an increased peripheral cell density compared to the center of the muscle strip. Muscle strips were fixed for a minimum of 12 h in 70% ethanol, then dehydrated and fixed in an overnight tissue processor (ASP300, Leica). Samples were embedded in paraffin, cut into 5-15 µm sections with a microtome (Leica), mounted on glass slides, and stained with hematoxylin and eosin (H&E). After 24 h, they were imaged with a Digital Pathology System (Nanozoomer). Over 75% of cells were within 200 µm of the edge of the fibrin muscle strip.

An MTS assay was used to evaluate cell viability over time. Muscle strips comprising $5\times10^{-6}$ cells/mL and supplemented with IGF-1 and aminocaproic acid were incubated with MTS (Promega) and phenazine methosulfate (Sigma-Aldrich) in DMEM without phenol red for 4 h at 37° C. Absorbance of MTS formazan product formation was measured at 490 nm using a Synergy HT microplate reader (BioTek) for four different time points and normalized to day 0 (day of cell seeding). The relative absorbance of muscle strips indicated a viability of cells within the muscle strip of 85.76±10.74% and 79.71±14.78% after days 6 and 9, respectively. As compared to the control muscle strips on day 9, the IGF-1 supplemented muscle strips demonstrated enhanced cell proliferation.

Example 16: Optimization of Muscle Force Generation

The stiffness of the beam that connected the two pillars was modulated by the laser exposure energy rather than tuning the elastic modulus of the beam by changing PEGDA $M_w$. To measure the bulk elastic modulus of the beams, dumbbell-shaped hydrogels were fabricated with laser exposure energies varying from 100-550 mJ/cm. The dumbbells were fit to a tensile tester and stretched under uniaxial tension in liquid. A pair of 1.2 mm diameter bent stainless steel rods (McMaster Carr) was super-glued to the ends of the dumbbells. The rods were placed into a custom-made fixture fabricated from VeroWhite polymer with an Eden 350 3D printing system (Objet). The fixture was designed to fit within an Electroforce Biodynamic test frame (Bose). The Electroforce system was fitted with a 1000 g load cell and sealed sample chamber for submerged testing. Testing was conducted within a 37° C. incubator. Once the hydrogel construct was placed in the fixture, the distance between the rods was measured with calipers and the fluid chamber was filled with 37° C. phosphate buffered saline (Lonza). The test was conducted in displacement control using WinTest control software (Bose). The samples were stretched under uniaxial tension in a Bose Electroforce Biodynamic tester at 0.05 mm/s. A video extensometer was used to track the displacement of four dots placed on the sample with a permanent marker. Load, displacement, and strain data were collected at 10 Hz using the Wintest software. The cross-sectional area of each sample was measured with calipers following the test. The extracted elastic moduli are shown in Table 8, indicating that the elastic moduli increased logarithmically with laser energy doses due to a higher degree of cross-linking by higher energy doses. The wide range in values observed demonstrated the utility of laser exposure energy in tuning the elastic modulus of the beam without having to change materials, a unique advantage of the SLA that would be difficult with other UV sources. With compaction of the muscle strip, traction forces exerted by cells produced an inward force on the pillars, which gave rise to varying degrees of bending in the beam. The stiffer hydrogel structures offered a greater resistance to bending; thus, beams with higher elastic moduli exhibited a lower deflection in response to passive tension forces exerted by the muscle strips.

TABLE 8

Extracted elastic moduli associated with varying laser exposure energies.

| Laser Exposure Energies (mJ/cm) | Extracted Elastic Modulus (kPa) |
| --- | --- |
| 100 | 155 |
| 109 | 215 |
| 150 | 402 |
| 250 | 551 |
| 513 | 742 |
| 550 | 757 |

Using Euler-Bernoulli linear bending theory, a formula was derived relating the observed hydrogel beam deflection to the muscle-generated passive tension force. Assuming negligible rotation in the beam and a small angle approximation, equating the applied moment M to tension P times the moment arm I from the muscle strip to the beam reduced the second-order differential equation to $$\frac{d^2y}{dx^2} = \frac{M}{EI}$$

where I is the moment of inertia of the rectangular cross-section and y is the horizontal deflection of the beam. Boundary conditions were applied by assuming zero deflection at ends of the beam (L=0) and maximum deflection $\delta_{mas}$ at the center (L/2).

$$\delta_{max} = |y(L/2)| = \frac{ML^2}{8EI} = \frac{PlL^2}{8EI}$$

Beam dimensions, moment arm, and maximum deflection were averaged from 3 measurements of each device using the Measure Tool in ImageJ (NIH). Solving for P yielded the relation:

$$P = \frac{8EI\delta_{max}}{lL^2}$$

An increase in beam stiffness resulted in an increased tension in the muscle strip at rest. The passive tension of fibrin-based muscle strips cultured with IGF-1 for elastic moduli 214.6-489.3 kPa is shown in Table 9. Finite element analysis was then used to model and simulate global displacement of the beam and pillars in response to an applied force; the simulated deflection values differed 18-19% from actual measurements.

TABLE 9

Passive tension forces generated by fibrin muscle strip bio-bots.

| Elastic Moduli (kPa) | Passive Tension (µN) |
| --- | --- |
| 214.6 | 860.6 ± 47.2 |
| 319.4 | 992.7 ± 34.3 |
| 411.2 | 1103.6 ± 45.8 |
| 489.3 | 1146.0 ± 69.0 |

To determine an optimal matrix system for engineered muscle functionality, the passive tension forces generated by collagen- and fibrin-based cell-matrix systems were compared. In muscle strips comprising the same number of cells, a significant increase in passive tension in those containing fibrin (629.3±8.2 µN) compared to collagen (534.2±5.8 µN) was observed. Advantageously, fibrin polymerizes relatively quickly when compared to other ECM proteins, and it can undergo large deformations without breaking (Liu et al., 2006, Science 313(5787):634; Janmey et al., 2009, J R Soc Interface 6(30):1-10). The ability to sustain large strains while maintaining structural integrity during muscle contraction was a necessary characteristic for applications in bio-actuation. Passive tension can be about 500, 600, 700, 800, 900, 1,000, 1,100, 1,200, 1,300, 1,400, 1,500, or more µN (or any range between about 500 and 1,500 µN) or about 1,500, 1,400, 1,300, 1,200, 1,100, 1,000, 900, 800, 700, 600, 500 or less µN (or any range between about 1,500 and 500 µN).

Examining the effect of varying other biological environmental cues, fibrin-based muscle strips supplemented with IGF-1 demonstrated a 70.7% increase in passive tension force, from 581.4±20.6 to 992.7±34.3 µN (P<0.001, n=4), compared to the control without IGF-1. This significant increase in force production was likely due to a greater number of differentiated myotubes in muscle strips supplemented with IGF-1. A normalized stress in the muscle strips with IGF-1 was calculated by dividing the passive tension by the cross-sectional area of the tissue, which averaged 1.2±0.04 mm$^2$ (n=9). The passive stress in the muscle strips averaged 0.84±0.03 kPa.

Example 17: Optimization of Collagen-Based Muscle Bio-Bot Fabrication

To confirm that gel compaction was caused by traction forces from the cells, muscle strips were treated with 50 µg/mL blebbistatin (FIG. 27A). Blebbistatin blocks myosin II activity in the cells, which prevents inward translation of the traction forces. Dissipation of compressive strain and lack of compaction on the ECM proteins followed. The muscle strips treated with IGF-1 (50 ng/mL) compacted rapidly but snapped near the posts within 24 h (FIG. 27C). Thus, the formation of muscle strips was cell-induced through passive tension around the two posts. FIG. 28 shows degree of flexure is dependent on beam stiffness.

Several methods were used to adjust or control the passive tension exerted by the cells on the collagen-based muscle strip bio-bots. A high cell concentration, either initially or through proliferation during culture, produced higher traction forces that ultimately led to snapping of collagen muscle strips, normally at its weakest point near the posts. The cell concentration was varied at 1.0×10$^6$ (FIG. 29A), 2.5×10$^6$ (FIG. 29B), and 5×10$^6$ (FIG. 29C) cells/mL. All three conditions snapped before 120 h. The collagen concentration was also varied at 0.8 (FIG. 29A), 1.4 (FIG. 29D), and 2.0 (FIG. 29E) mg/mL, which increased the stiffness of the muscle strip due to higher cross-linking densities. Again, all the conditions snapped before the 120 h. However, upon addition of the protease inhibitor, aminocaproic acid (1 mg/mL), to the medium, the muscle strips remained intact (FIG. 29F). Muscle strips comprising the protease inhibitor remained stable even after 14 days. Table 10 summarizes optimized conditions for fabricating collagen-based muscle strip bio-bots.

TABLE 10

Parameters for collagen-based muscle strip bio-bot fabrication.

| Condition | Concentration/Parameter |
|---|---|
| [Cell] | $2.5 \times 10^6$-$5.0 \times 10^6$ cells/mL |
| [Matrix] | 1.4 mg/mL type 1 collagen<br>30% v/v Matrigel ™ |
| [aminocaproic acid] | 1 mg/mL |
| Beam Parameters | ~500 μm (thickness)<br>~400 kPa (elastic modulus) |

Similarly, the lifetime of fibrin muscle strip bio-bots (i.e. days until fracture of the muscle strip) was affected by the presence or absence of 50 ng/mL IGF-1 and/or 1 mg/mL aminocaproic acid. There was a significant increase in the fibrin muscle strip lifetime with the addition of 1 mg/mL aminocaproic acid (25±1.15 days) compared to the control of 10% HS (8.75±7.63). The addition of 50 ng/mL IGF-1 decreased the number of days until fracture compared to the control (51.43% decrease) and the 1 mg/mL ACA condition (22.0% decrease).

Example 18: Electrically Paced Actuation of Muscle Strip Bio-Bots

Collagen-based muscle strip bio-bots made with C2C12 cells expressing ChR2 were observed to twitch spontaneously. Each time the muscle strip twitched, the posts displaced inward and returned to their original position upon relaxation. Contractile myotubes in the muscle strips were stimulated with blue light using a fluorescent light (Xeon) that is passed through a FITC filter (460-490 nm) and focused through a 20× objective lens. The light was switched on and off at 5 s intervals using this setup. For pulsed light, a blue LED light was connected to a waveform generator (Agilent) and pulsed at different periods (250, 500, and 1000 ms) with a pulse width of 100 ms. Actuation of the bio-bot legs was imaged with an inverted microscope (IX81, Olympus). When the muscle strips comprising C2C12 cells expressing ChR2 were exposed to blue light, either continuously or pulsed at 500 ms intervals, there were several cases that the frequency of the twitching had increased.

Figure 30A:
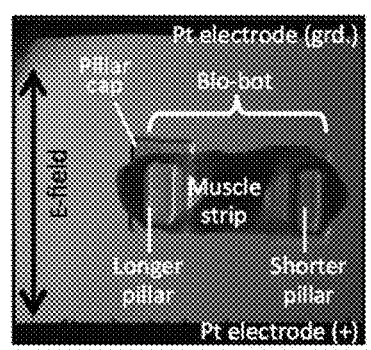
FIG. 30A shows the orientation of a 3D muscle powered bio-bot in relation to the electrodes and applied field for electrical stimulation. The muscle strip's longitudinal axis is parallel to the electrodes and perpendicular to the applied field.
Figure 30B:
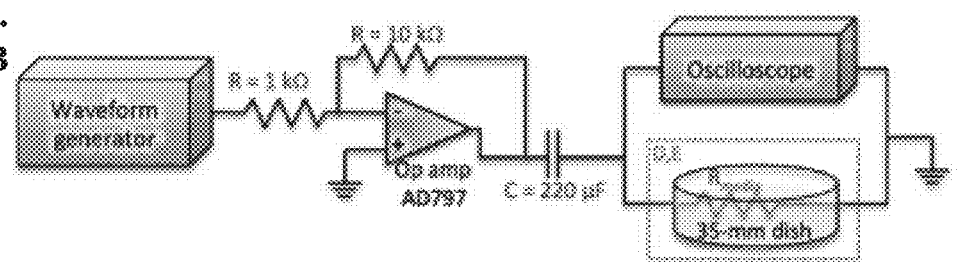
FIG. 30B is a schematic of an electrical stimulation setup.

To externally control muscle contraction and bio-bot locomotion, a custom-designed setup (Bajaj et al., 2011, *Integr Biol (Camb)* 3(9):897-909) was used to stimulate reproducible contraction of excitable cells within the muscle strip with a bipolar electrical pulse train (FIGS. 30A and 30B). The output from a waveform generator was amplified through an AD797 inverting amplifier. A capacitor C was added in series to minimize electrolysis of the media by converting the square pulse to a biphasic pulse; the system was then treated as an RC circuit (FIG. 30B). A 35-mm culture dish was modified to allow Pt electrodes of diameter 0.762 mm to pass through the lid of the dish. The average resistance of the electrical stimulation medium (DMEM without serum) was calculated by measuring the time constant τ from the oscilloscope and dividing by C for each volume at 23° C. and 37° C. The conductivity of the medium was measured using a pH/Conductivity meter (Orion 4-Star, Thermo Scientific), at 23° C. and 37° C. During stimulation, the bio-bot was placed in 4 mL of warm electrical stimulation medium between the positive and ground electrodes, and a current was applied perpendicular to the long axis, with stimulation frequencies up to 10 Hz and never exceeding more than half of the sampling frequency, per the Nyquist criterion. Bio-bots were stimulated with bipolar electrical pulses of 20 V amplitude (21.6 V/cm field strength) and 50 ms pulse width. Simultaneous imaging was achieved by positioning the dish on the stage of a stereoscope. Top-view movies were acquired with a stereomicroscope with a digital microscope camera at 9.2 fps. Side-view movies were acquired using a camcorder (Handycam DCR-SR65, Sony) at 30 fps. Electrodes were sterilized in 70% ethanol and rinsed with PBS between experiments.

Fibrin-based muscle strips supplemented with IGF-1 and stimulated at constant frequencies demonstrated a consistent output (Table 11). Twitch contractions were observed below 8-10 Hz and tetanus above this upper frequency limit. In contrast, non-IGF-1 supplemented muscle strips did not respond to stimulation during this time period, a result attributed to the fewer numbers of myotubes. As well, the range of active tension remained above 99.3% of the initial value during 8 min of electrical stimulation at hour 0 and above 98.8% of the initial value at hour 6, revealing a consistent force output from the engineered muscle strips both with a constant stimulation period and at later time points.

TABLE 11

Output of muscle strips supplemented with IGF-1.

| Stimulation (Hz) | Output (Contractions/s) |
|---|---|
| 1 | 1.01 ± 0.003 |
| 2 | 2.01 ± 0.01 |
| 4 | 3.95 ± 0.05 |

A Kelvin-Voigt viscoelasticity model that correlated the observed cyclic displacement to the contractile force was used to extract the active tension generated by IGF-1 supplemented muscle strips in response to electrical stimulation. The active stress generated by the muscle strip was computed as a function of the strain $\varepsilon(t)$ and strain rate $d\varepsilon(t)/dt$ observed in the hydrogel beam with viscosity $\eta$. The time-varying displacement data was converted into time-varying strain, and the following equation was used to compute the resulting active stress:

$$\sigma(t) = E\varepsilon(t) + \eta \frac{d\varepsilon(t)}{dt}$$

The range of active tension during contraction decreased with increasing stimulation frequency, from a dynamic fluctuation of 198.68 μN during 1 Hz stimulation to 109.48 μN during 4 Hz stimulation. The active tension data followed a positive force-frequency relationship in which the magnitude of the active tension exerted by the muscle increased, even while the range of pillar motion decreased. Furthermore, as a consequence of muscle relaxation times exceeding the period between electrical pulse stimulation at higher frequencies, a temporal summation of force was observed that resulted in a baseline tension increase over time. The muscle strips therefore displayed functional behavior characteristic to physiological skeletal muscle, in which force output increased with frequency before reaching tetanus.

Example 19: Demonstration of Controlled Directional Movement

Figure 31A:
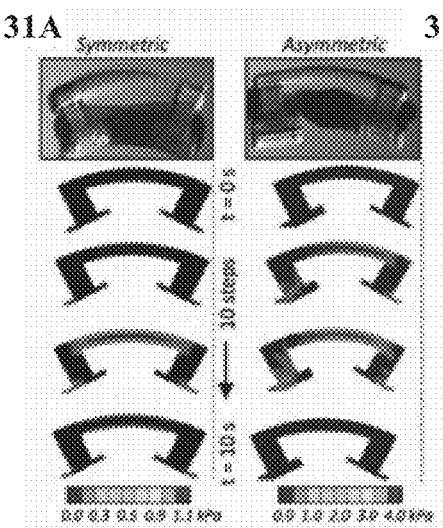
FIG. 31A shows finite-element simulations of symmetric and asymmetric muscle strip bio-bots supplemented with IGF-1 over a period of 10 s.

To create a biomimetic 'crawling' mechanism reminiscent of an inchworm's movement, finite element simulations were first used to explore a symmetric and an asymmetric design for the bio-bots (FIG. 31A). An automated Matlab script was designed to track the location of a user-specified feature with a normalized 2D cross-correlation and provided X-Y coordinates of a specific point on the bio-bot for each frame. This software tracked the distance between the pillar caps during stimulation from a top-view movie. To model deformation and stress in the active (contracting) state, pillar displacements (from the Matlab script) were imported into the simulation to recapitulate the walking motion captured from top-view movies of symmetric and asymmetric bio-bots. Bio-bots were placed on a frictionless support surface ("ground") and allowed to deform and move with respect to the ground in response to the displacement input. The simulation provided time-varying stresses in the bio-bot structure and time-varying reaction forces from the ground.

Figure 3A:
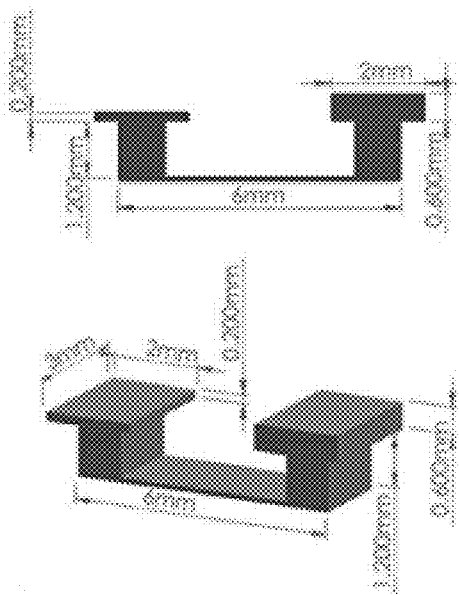
FIG. 3A shows an asymmetric design for a walking muscle strip bio-bot.
Figure 3B:
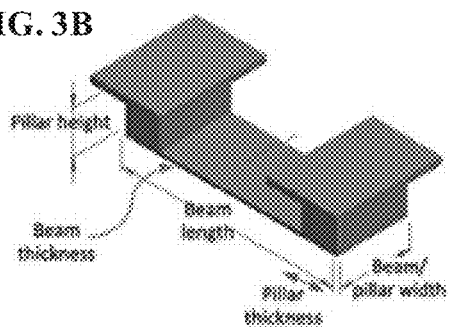
FIG. 3B indicates an example of the dimension parameters for a muscle strip bio-bot.

The symmetric structure did not demonstrate significant locomotion in the simulations. For the asymmetric design, the length of one pillar of the bio-bot hydrogel structure was extended, allowing for asymmetric bending of the flexible beam (FIGS. 3A and 3B). The asymmetric structure exhibited non-uniform distribution of stress in the hydrogel structure in response to muscle contraction, corresponding to asymmetric pillar displacements (FIG. 31A). Simulations revealed that asymmetric actuation and force generation of the muscle strips by geometric design of the bio-bot produced greater net displacement over a fixed time and create a more efficient and predictable locomotive mechanism as compared to the symmetric design.

Figure 31B:
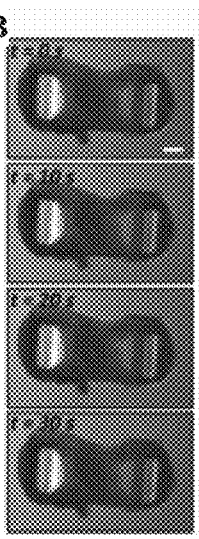
FIG. 31B shows top-view time-lapse images of a symmetric muscle strip bio-bot.

Consistent with the simulation results, for a symmetric hydrogel structure, electrical pacing of skeletal muscle strips attached to bio-bot structures either did not result in net locomotion of the bio-bot across a substrate, or in some cases, resulted in a very small locomotion (FIG. 31B). Since the hydrogel structure itself was symmetric, it was hypothesized that any observed small locomotion of the symmetric structure was attributed to asymmetry in muscle strip formation and force distribution. From a top-view video, bio-bot pillar displacements were tracked in response to muscle contractions over time. To find the time-averaged ratios of pillar movement, the difference in X and Y coordinates of the pillar caps for each point was converted to a total distance moved between individual frames (i.e., from n to n+1), then divided using the following equation:

$$\frac{\text{pillar}_1}{\text{pillar}_2} = \frac{\sqrt{(\Delta x_{p1})^2 + (\Delta y_{p1})^2}}{\sqrt{(\Delta x_{p2})^2 + (\Delta y_{p2})^2}} = \frac{\sqrt{(x_{p1(n+1)} - x_{p1(n)})^2 + (y_{p1(n+1)} - y_{p1(n)})^2}}{\sqrt{(x_{p2(n+1)} - x_{p2(n)})^2 + (y_{p2(n+1)} - y_{p2(n)})^2}}$$

Figure 31C:
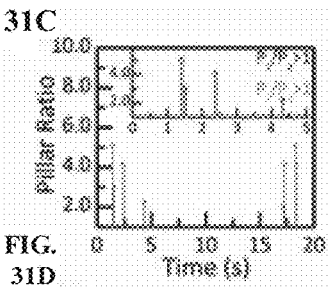
FIG. 31C shows relative ratios of pillar movement of a symmetric muscle strip bio-bot with 1 Hz stimulation.
Figure 31D:
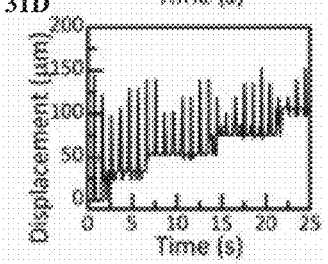
FIG. 31D shows maximum displacement of a symmetric muscle strip bio-bot with 1 Hz stimulation.

When both pillars displaced equally, the bio-bot did not move. Interestingly, for the minimally locomotive bio-bots, when one pillar displaced more than the other (FIG. 31C), the bio-bot always 'crawled' in the direction of the pillar that demonstrated greater displacement in response to muscle contraction. For the case of these symmetric devices, these small velocities were found to be less than 4.34 µm/s at electrical stimulation of 1 Hz frequency (FIG. 31D).

Figure 31E:
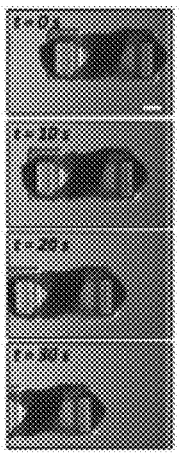
FIG. 31E shows top-view time-lapse images of an asymmetric muscle strip bio-bot.
Figure 31F:
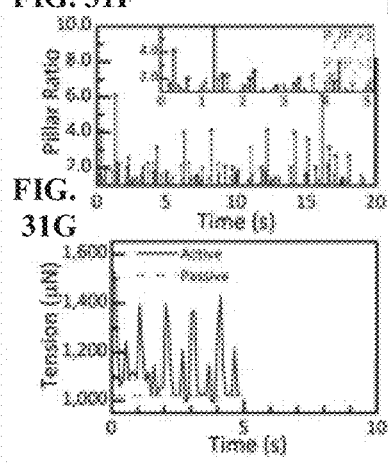
FIG. 31F shows relative ratios of pillar movement of an asymmetric muscle strip bio-bot with 1 Hz stimulation.
Figure 31G:
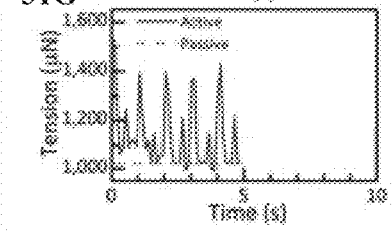
FIG. 31G shows active tension force of an asymmetric muscle strip bio-bot during locomotion.
Figure 31H:
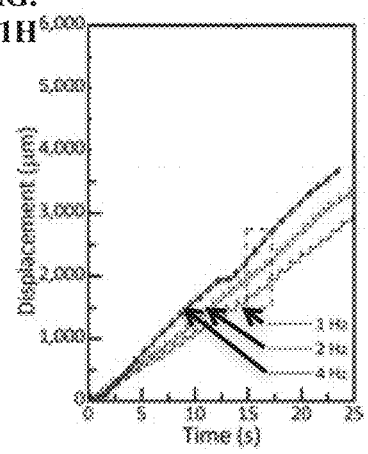
FIG. 31H shows displacement over time of asymmetric muscle strip bio-bots with varying stimulation. The increased number of contractions with increasing stimulation frequency within a given time period resulted in an increased velocity of the asymmetric bio-bot.

Muscle strips coupled to the asymmetric compliant hydrogel structure drove inchworm-like crawling locomotion with maximum velocity. Contraction of muscle strips on asymmetric bio-bots resulted in a maximum velocity of 117.8 µm/s in response to electrical stimulation of 1 Hz frequency, an increase in velocity of more than 25-fold increase compared to the symmetric design (FIGS. 31E-G). During electrically paced locomotion, the asymmetric bio-bot produced an active tension force of 290.5±27.0 µN, or 22.1% of the maximum force (FIG. 31G). Although bio-bot pillar displacement decreased with increasing stimulation frequency, the observed increase in force generation led to testing the effect of stimulation frequency on bio-bot locomotion. The increased number of contractions with increasing stimulation frequency within a given time period resulted in an increased average velocity of the asymmetric bio-bot, as shown in Table 12. At all frequencies, the asymmetric bio-bot moved in the direction of the pillar that demonstrated greater displacement.

TABLE 12

Average velocity of the asymmetric muscle strip bio-bot.

| Stimulation (Hz) | Velocity (µm/s) |
|---|---|
| 1 | 117.8 |
| 2 | 132.2 |
| 4 | 156.1 |

We claim:
1. A composition comprising:
   (a) two or more hydrogel pillars having top and bottom base end surfaces, wherein the two or more hydrogel pillars are coupled to a lower surface of a hydrogel beam, at their top base end surfaces, wherein the hydrogel beam extends between the two or more hydrogel pillars; and
   (b) a solid muscle tissue strip comprising (i) muscle cells or (ii) muscle cells and one or more types of cells, wherein the solid muscle tissue strip forms a solid muscle tissue strip between the two or more pillars, surrounds the two or more pillars, and is not in contact with the hydrogel beam.
2. The composition of claim 1, wherein the two or more hydrogel pillars have caps on their bottom base end surfaces.
3. The composition of claim 2, wherein the one or more of the caps have a different thickness than one or more of the other caps.
4. The composition of claim 1, wherein the one or more of the hydrogel pillars have a different height than one or more of the other hydrogel pillars.
5. The composition of claim 1, wherein the one or more cell types are neurons, cardiac muscle cells, skeletal muscle cells, progenitor muscle cells, endothelial cells, fibroblasts or combinations thereof.
6. The composition of claim 1, wherein the one or more cell types comprise neurons and muscle cells, wherein the muscle cells form one or more muscle fibers and wherein the neurons and muscle fibers comprise one or more neuromuscular junctions.
7. The composition of claim 1, wherein the muscle cells, the one or more cell types, or the muscle cells and the one or more cell types can be activated by light, an electric current, or a chemical compound.

8. The composition of claim 1, wherein the muscle tissue strip comprises one or more extracellular matrix proteins.

9. The composition of claim 1, wherein 3 or more hydrogel pillars are arranged in a row and are all coupled to a hydrogel beam at the top base end surfaces of the hydrogel pillars, wherein one or more of the hydrogel pillars are further connected via an additional hydrogel beam in one or both perpendicular directions from the row to an additional one or more pillars, wherein the additional hydrogel beam connects the top base end surfaces of the hydrogel pillars.

10. The composition of claim 1, wherein the hydrogel pillars are arranged in rows and columns within a grid-like array with one or more rows of hydrogel pillars and one or more columns of hydrogel pillars, wherein each row of hydrogel pillars is connected at the top base end surfaces of the hydrogel pillars by a hydrogel beam and wherein each column of hydrogel pillars is connected at the top base end surfaces of the hydrogel pillars by a hydrogel beam.

11. A composition comprising:
 (a) a multitude of hydrogel pillars having top and bottom base end surfaces arranged in rows and columns within a grid-like array with one or more rows of hydrogel pillars and one or more columns of hydrogel pillars, wherein each row of hydrogel pillars is connected at the top base end surfaces of the hydrogel pillars by a hydrogel base, wherein the hydrogel base connects all the hydrogel pillars;
 (b) a muscle tissue strip comprising (i) muscle cells or (ii) muscle cells and one or more types of cells, wherein the muscle tissue strip forms a solid muscle tissue strip between the two or more pillars, surrounds the two or more pillars, and is not in contact with the hydrogel base.

12. The composition of claim 11, wherein the multitude of hydrogel pillars have caps on their bottom base end surfaces.

13. The composition of claim 12, wherein the one or more of the caps have a different thickness than one or more of the other caps.

14. The composition of claim 11, wherein the one or more of the hydrogel pillars have a different height than one or more of the other hydrogel pillars.

15. The composition of claim 11, wherein the one or more cell types are neurons, cardiac muscle cells, skeletal muscle cells, progenitor muscle cells, endothelial cells, fibroblasts or combinations thereof.

16. The composition of claim 11, wherein the one or more cell types comprise neurons and muscle cells, wherein the muscle cells form one or more muscle fibers and wherein the neurons and muscle fibers comprise one or more neuromuscular junctions.

17. The composition of claim 11, wherein the one or more cell types can be activated by light, an electric current, or a chemical compound.

18. A method of controlling the directional locomotion of the composition of claim 1 comprising exposing the entire composition or a selected portion of the composition to light, an electrical pulse, or a chemical.

19. The method of claim 18, wherein controlling the directional locomotion of the composition includes starting locomotion, stopping locomotion, slowing locomotion, accelerating locomotion, changing the direction of locomotion.

20. A method of detecting the response of the composition of claim 1 to one or more test agents comprising: contacting the composition with the one or more test agents and monitoring one or more of the following parameters: cell death, cell viability, number of cells, apoptosis, cell proliferation, contractile responses of the cells, angiogenesis, movement of the composition, or directional locomotion of the composition, wherein the response of the composition to the test agents are detected.

* * * * *